US012808882B2

(12) United States Patent
Weins et al.

(10) Patent No.: US 12,808,882 B2
(45) Date of Patent: Nov. 24, 2026

(54) METHODS FOR IDENTIFYING AND TREATING ANTIBODY-MEDIATED ACQUIRED PRIMARY OR RECURRENT IDIOPATHIC NEPHROTIC SYNDROME

(71) Applicants: The Brigham and Women's Hospital, Inc., Boston, MA (US); Boston Medical Center Corporation, Boston, MA (US)

(72) Inventors: Astrid Weins, Winthrop, MA (US); Helmut G. Rennke, Jamaica Plain, MA (US); Joel M. Henderson, Brookline, MA (US); Andrew Watts, Lexington, MA (US); Keith Keller, Brookline, MA (US)

(73) Assignees: THE BRIGHAM AND WOMEN'S HOSPITAL, INC., Boston, MA (US); BOSTON MEDICAL CENTER CORPORATION, Boston, MA (US)

( * ) Notice: Subject to any disclaimer, the term of this patent is extended or adjusted under 35 U.S.C. 154(b) by 591 days.

(21) Appl. No.: 18/033,222

(22) PCT Filed: Oct. 22, 2021

(86) PCT No.: PCT/US2021/056157
§ 371 (c)(1),
(2) Date: Apr. 21, 2023

(87) PCT Pub. No.: WO2022/087341
PCT Pub. Date: Apr. 28, 2022

(65) Prior Publication Data
US 2023/0393147 A1 Dec. 7, 2023

Related U.S. Application Data
(60) Provisional application No. 63/104,306, filed on Oct. 22, 2020.

(51) Int. Cl.
*G01N 33/53* (2006.01)
*G01N 33/68* (2006.01)

(52) U.S. Cl.
CPC ..... *G01N 33/6893* (2013.01); *G01N 33/6854* (2013.01); *G01N 2333/705* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,545,566 | A * | 8/1996 | Growden | G01N 33/92 514/78 |
| 8,691,952 | B2 | 4/2014 | Super et al. | |
| 2003/0103976 | A1 | 6/2003 | Serizawa et al. | |
| 2011/0301103 | A1 | 12/2011 | Chugh | |
| 2016/0256478 | A1 | 9/2016 | Chugh | |
| 2016/0271218 | A1 | 9/2016 | Biro | |
| 2017/0176434 | A1 | 6/2017 | Sarwal | |
| 2023/0393147 | A1 | 12/2023 | Weins et al. | |

FOREIGN PATENT DOCUMENTS

| | | |
|---|---|---|
| JP | 2006-76958 A | 3/2006 |
| WO | WO 2000/077044 | 12/2000 |
| WO | WO 2014/207748 | 12/2014 |
| WO | WO 2015/154056 | 10/2015 |
| WO | WO 2019/136373 | 7/2019 |

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Supporting Evidence Document, Corticosteroid Protocol for MCD and FSGS, BC Renal Agency, Jan. 2019, pp. 1-4. (Year: 2019).*
Vivarelli et al., Minimal Change Disease, Clin J Am Soc Nephrol 12: 2017, pp. 322-345. (Year: 2017).*
Oleinika et al., Effector and regulatory B cells in Immune-mediated kidney disease, Nat Rev Nephrol, Jan. 2019, 15(1) ,pp. 1-35. (Year: 2019).*
Ruotsalainen et al., Nephrin is specifically located at the slit diaphragm of glomerular podocytes, Proc. Natl. Acad. Sci. USA, vol. 96, pp. 7962-7967, Jul. 1999. (Year: 1999).*
Aaltonen et al., Circulating antibodies to nephrin in patients with type 1 diabetes, Nephrol Dial Transplant, 2007, 22: pp. 146-153. (Year: 2007).*
Harlow, E. and Lane, D., Antibodies: A Laboratory Manual (1988) Cold Spring Harbor Laboratory Press, Cold Spring Harbor, NY, pp. 23-26 (Year: 1988).*
Lederman et al. "A single amino acid substitution in a common African allele of the CD4 molecule ablates binding of the monoclonal antibody, OKT4" Mol Immunol. Nov. 1991;28(11):1171-81 (Year: 1991).*
Colman et al. Research in Immunology, 1994; 145(1): 33-36 (Year: 1994).*
Brody et al., "High-content affinity-based proteomics: unlocking protein biomarker discovery", Expert Review of Molecular Diagnostics, vol. 10, No. 8, Jan. 9, 2014, pp. 1013-1022.
Hartung et al., "Atacicept: targeting B cells in multiple sclerosis", Therapeutic Advances in Neurological Disorders, vol. 3, No. 4, 2010, pp. 205-216.

(Continued)

*Primary Examiner* — Gary Counts
(74) *Attorney, Agent, or Firm* — Grüneberg Global IP, PLLC

(57) ABSTRACT

Described herein are methods and kits for diagnosing and treating minimal change disease, and for identifying subjects for eligibility or treatment before kidney transplant, based on the presence of circulating anti-nephrin autoantibodies.

17 Claims, 19 Drawing Sheets

Specification includes a Sequence Listing.

(56) References Cited

OTHER PUBLICATIONS

Kim et al., "Automated Heart-Type Fatty Acid-Binding Protein Assay for the Early Diagnosis of Acute Myocardial Infarction", Am. J. Clin. Pathol., vol. 134, 2010, pp. 157-162.
Naddafi et al., "Anti-CD19 Monoclonal Antibodies: a New Approach to Lymphoma Therapy", Int. J. Mol. Cell Med. Summer, vol. 4, No. 3, Jul. 21, 2015, pp. 143-151.
Pfaffe et al., "Diagnostic Potential of Saliva: Current State and Future Applications", Clinical Chemistry, vol. 57, No. 5, Jan. 21, 2011, pp. 675-687.
Phillips et al., "Rapid Point-of-Care Breath Test for Biomarkers of Breast Cancer and Abnormal Mammograms", PLOS ONE, vol. 9, Issue 3, e90226, Mar. 5, 2014, pp. 1-6.
Yasun et al., "Enrichment and Detection of Rare Proteins with Aptamer-conjugated Gold Nanorods", Anal Chem., vol. 84, No. 14, Jul. 17, 2012, pp. 1-15.
Basu, "Ofatumumab for rituximab-resistant nephrotic syndrome," New England Journal of Medicine, Mar. 2014, 370(13):1268-70.
Basu et al., Efficacy of rituximab vs tacrolimus in pediatric corticosteroid-dependent nephrotic syndrome: a randomized clinical trial. JAMA pediatrics. Aug. 1, 2018;172(8):757, 19 pages.
Beck et al., "M-type phospholipase A2 receptor as target antigen in idiopathic membranous nephropathy," New England Journal of Medicine, Jul. 2009, 361(1):11, 20 pages.
Chaudhuri et al., "Rituximab treatment for recurrence of nephrotic syndrome in a pediatric patient after renal transplantation for congenital nephrotic syndrome of Finnish type," Pediatric Transplantation, Aug. 2012, 16(5):E183-7.
Coward et al., "Nephrotic plasma alters slit diaphragm-dependent signaling and translocates nephrin, Podocin, and CD2 associated protein in cultured human podocytes," Journal of the American Society Nephrology, Mar. 2005, 16(3):629-37.
D'Agati, "Minimal Change Diseases," Atlas of Nontumor Pathology, Non-neoplastic Kidney Diseases, American Registry of Pathology, Jan. 2005, 4(109), 10 pages.
Delville et al., "A circulating antibody panel for pretransplant prediction of FSGS recurrence after kidney transplantation," Science Translational Medicine, Oct. 2014, 6(256):256ra136-.
Doublier et al., "Nephrin redistribution on podocytes is a potential mechanism for proteinuria in patients with primary acquired nephrotic syndrome," The American Journal of Pathology, May 2001, 158(5):1723-31.
Elie et al., "Physiopathology of idiopathic nephrotic syndrome: lessons from glucocorticoids and epigenetic perspectives," Pediatric Nephrology, Aug. 2012, 27:1249-56.
Fenoglio et al., "Rituximab as a front-line therapy for adult-onset minimal change disease with nephrotic syndrome," Oncotarget, Jun. 2018, 9(48):28799-804.
Gadegbeku et al., "Design of the Nephrotic Syndrome Study Network (NEPTUNE) to evaluate primary glomerular nephropathy by a multidisciplinary approach," Kidney International, Apr. 2013, 83(4):749, 17 pages.
Gillies et al., "An eQTL landscape of kidney tissue in human nephrotic syndrome," The American Journal of Human Genetics, Aug. 2018, 103(2):232-44.
Grahammer et al., "The podocyte slit diaphragm—from a thin grey line to a complex signalling hub," Nature Reviews Nephrology, Oct. 2013, 9(10):587-98.
Gustafsson, "Surpassing the lateral resolution limit by a factor of two using structured illumination microscopy," Journal of Microscopy, May 2000, 198(2):82-7.
Hammers et al., "Mechanisms of disease: pemphigus and bullous pemphigoid," Annual Review of Pathology: Mechanisms of Disease, May 2016, 11:175, 25 pages.
Hansrivijit et al., "Rituximab therapy for focal segmental glomerulosclerosis and minimal change disease in adults: a systematic review and meta-analysis," BMC Nephrology, Dec. 2020, 21:1, 12 pages.
Hiraoka et al., "Determination of three-dimensional imaging properties of a light microscope system. Partial confocal behavior in epifluorescence microscopy," Biophysical Journal, Feb. 1990, 57(2):325-33.
Holmberg et al., "Congenital nephrotic syndrome and recurrence of proteinuria after renal transplantation," Pediatric Nephrology, Dec. 2014, 29:2309-17.
Jun et al., "An efficient and scalable analysis framework for variant extraction and refinement from population-scale DNA sequence data," Genome Research, Jun. 2015, 25(6):918-25.
Kaplan, "Therapeutic plasma exchange: a technical and operational review," Journal of Clinical Apheresis, Feb. 2013, 28(1):3-10.
Kestilä et al., "Positionally cloned gene for a novel glomerular protein-nephrin-is mutated in congenital nephrotic syndrome," Molecular Cell, Mar. 1998, 1(4):575-82.
Khoshnoodi et al., "Nephrin promotes cell-cell adhesion through homophilic interactions," The American Journal of Pathology, Dec. 2003, 163(6):2337-46.
Kuusniemi et al., "Plasma exchange and retransplantation in recurrent nephrosis of patients with congenital nephrotic syndrome of the Finnish type (NPHS1)," Transplantation, May 2007, 83(10):1316-23.
Liu et al., Defective nephrin trafficking caused by missense mutations in the NPHS1 gene: insight into the mechanisms of congenital nephrotic syndrome: Human Molecular Genetics, Nov. 2001, 10(23):2637-44.
Madanchi et al., "Rituximab in minimal change disease: Mechanisms of action and hypotheses for future studies," Canadian Journal of Kidney Health and Disease, Mar. 2017, 4, 15 pages.
Mansur et al., "Minimal-Change Disease," Medscape, Jan. 2021, retrieved Oct. 8, 2021 from URL <emedicine.medscape.com/article/243348>, 13 pages.
Matsuda et al., "Accurate and fiducial-marker-free correction for three-dimensional chromatic shift in biological fluorescence microscopy," Scientific Reports, May 2018, 8(1):7583, 14 pages.
Nagahama et al., "Possible role of autoantibodies against nephrin in an experimental model of chronic graft-versus-host disease," Clinical & Experimental Immunology, Aug. 2005, 141(2):215-22.
Nguyen et al., "Pemphigus vulgaris IgG and methylprednisolone exhibit reciprocal effects on keratinocytes," Journal of Biological Chemistry, Jan. 2004, 279(3):2135-46.
Orikasa et al., "Massive proteinuria induced in rats by a single intravenous injection of a monoclonal antibody," Journal of Immunology (Baltimore, Md.: 1950), Aug. 1988, 141(3):807-14.
PCT International Preliminary Report on Patentability in International Appln. No. PCT/US2021/056157, mailed on Apr. 13, 2023, 8 pages.
PCT International Search Report and Written Opinion in International Appln. No. PCT/US2021/056157, mailed on Jan. 31, 2022, 10 pages.
Ravani et al., "Clinical trials in minimal change disease," Nephrology Dialysis Transplantation, Jan. 2017, 32(suppl 1):17-13.
Ravani et al., "Anti-CD20 antibodies for idiopathic nephrotic syndrome in children," Clinical Journal of the American Society of Nephrology: CJASN, Apr. 2016, 11(4):710.
Richards et al., "Standards and guidelines for the interpretation of sequence variants: a joint consensus recommendation of the American College of Medical Genetics and Genomics and the Association for Molecular Pathology," Genetics in Medicine, May 2015, 17(5):405, 38 pages.
Sampson et al., "Using population genetics to interrogate the monogenic nephrotic syndrome diagnosis in a case cohort," Journal of the American Society of Nephrology: JASN, Jul. 2016, 27(7):1970, 28 pages.
Takeuchi et al., "New anti-nephrin antibody mediated podocyte injury model using a C57BL/6 mouse strain," Nephron, Jan. 2018, 138(1):71-87.
Topham et al., "Nephritogenic mAb 5-1-6 is directed at the extracellular domain of rat nephrin," The Journal of Clinical Investigation, Dec. 1999, 104(11):1559-66.
Vivarelli et al., "Minimal change disease," Clinical Journal of the American Society of Nephrology: CJASN, Feb. 2017, 12(2):332, 25 pages.

(56) References Cited

OTHER PUBLICATIONS

Waritani et al., "An ELISA protocol to improve the accuracy and reliability of serological antibody assays," MethodsX. Jan. 2017, 4:153-65.
Wernerson et al., "Altered ultrastructural distribution of nephrin in minimal change nephrotic syndrome," Nephrology Dialysis Transplantation, Jan. 2003, 18(1):70-6.
Xing et al., "Direct effects of dexamethasone on human podocytes," Kidney International, Sep. 2006, 70(6):1038-45.
Aaltonen et al., "Circulating antibodies to nephrin in patients with type 1 diabetes," Nephrology Dialysis Transplantation, Jan. 2007, 22(1):146-53.
Butte et al., "Protein microarrays discover angiotensinogen and PRKRIP1 as novel targets for autoantibodies in chronic renal disease," Molecular & Cellular Proteomics, Mar. 2011, 10(3), 8 pages.
EP Extended European Search Report in European Appln. No. 21883944.7, mailed on Jul. 24, 2024, 15 pages.
Fujita et al., "Clinical Characteristics of Nephrin Autoantibody-Positive Minimal Change Disease in Older Adults," Kidney International Reports, May 2024, vol. 2024(9):2563-6.
Li et al., "Identifying compartment-specific non-HLA targets after renal transplantation by integrating transcriptome and "antibodyome" measures," Proceedings of the National Academy of Sciences, Mar. 2009, 106(11):4148-53.
Sigdel et al., "A Pivotal Circulating 1-15 Antibody Panel for Pre-Transplant Prediction of FSGS Recurrence after Kidney Transplantation, abstract No. 2022," American Journal of Transplantation, 13(Supp 5), May 2013, 1 page.
Wang et al., "Recurrence of nephrotic syndrome after transplantation in CNF is due to autoantibodies to nephrin," Experimental nephrology, Jul. 2001, 9(5):327-31.
Watts et al., "Autoantibodies against nephrin elucidate a novel autoimmune phenomenon in proteinuric kidney disease," medRxiv, Mar. 2021, vol. 2021, 25 pages.

* cited by examiner

| No. at risk | | | | | | | |
|---|---|---|---|---|---|---|---|
| Ab Positive | 18 | 7 | 4 | 3 | 2 | 2 | 0 |
| Ab Negative | 44 | 18 | 7 | 5 | 4 | 2 | 0 |

METHODS FOR IDENTIFYING AND TREATING ANTIBODY-MEDIATED ACQUIRED PRIMARY OR RECURRENT IDIOPATHIC NEPHROTIC SYNDROME

CLAIM OF PRIORITY

This application is the U.S. National Phase Application under 35 U.S.C. § 371 of International Patent Application No. PCT/US2021/056157, filed on Oct. 22, 2021, which claims the benefit of U.S. Provisional Application Ser. No. 63/104,306, filed on Oct. 22, 2020. The entire contents of the foregoing are incorporated herein by reference.

FEDERALLY SPONSORED RESEARCH OR DEVELOPMENT

This invention was made with Government support under Grant Nos. DK007053 awarded by the National Institutes of Health. The Government has certain rights in the invention.

SEQUENCE LISTING

This application contains a Sequence Listing that has been submitted electronically as an ASCII text file named '29618_0228US1_Sequence_Listing.txt'. The ASCII text file, created on Apr. 20, 2023, is 23,216 bytes in size. The material in the ASCII text file is hereby incorporated by reference in its entirety.

TECHNICAL FIELD

Described herein are methods and kits for diagnosing and treating minimal change disease, and for identifying subjects for eligibility or treatment before kidney transplant, based on the presence of circulating anti-nephrin autoantibodies.

BACKGROUND

Diffuse podocytopathy with minimal changes (Minimal Chance Disease (MCD)) is an important and common pathologic diagnosis in adults and children with nephrotic syndrome (NS). MCD is a podocytopathy of unknown etiology, affecting both adults and children, with evidence supporting a role for B-cells[10-13]. It is characterized by minimal changes by light microscopy, yet extensive injury to glomerular podocytes with diffuse foot process effacement (FPE) and loss of slit diaphragms (SD) by electron microscopy (EM) in the absence of electron dense deposits[1]. The consequence of these alterations is massive proteinuria secondary to failure of the glomerular filtration barrier (GFB), whose integrity is critically dependent on the specialized junctional SD protein complex linking the interdigitating podocyte foot processes.

SUMMARY

Provided herein are methods for diagnosing minimal change disease (MCD) in a subject. The methods include providing a sample from a subject who has, or who is suspected of having, MCD; determining a level of anti-nephrin antibodies in the sample; comparing the level of anti-nephrin antibodies in the sample to a reference level; and diagnosing a subject who has a level of anti-nephrin antibodies in the sample above a reference level as having or at risk of developing MCD.

In some embodiments, the methods include selecting a treatment for MCD to the subject.

Also provided herein are methods for treating minimal change disease (MCD) in a subject. The methods include providing a sample from a subject who has, or who is suspected of having, MCD; determining a level of anti-nephrin antibodies in the sample; comparing the level of anti-nephrin antibodies in the sample to a reference level; identifying a subject who has a level of anti-nephrin antibodies in the sample above a reference level as having or at risk of developing MCD; and administering a treatment for MCD to the subject.

In some embodiments, the treatment for MCD comprises administration of one or more of a glucocorticoid, a treatment that reduces levels of anti-nephrin antibodies, or a treatment that targets B cells, to the subject. In some embodiments, the glucocorticoid is prednisone, beclomethasone, betamethasone, budesonide, cortisone, dexamethasone, hydrocortisone, triamcinolone, prednisolone, or methylprednisolone. In some embodiments, the B-cell targeting therapy is a targeted therapy that depletes B cells or an inhibitor of B lymphocyte stimulation. In some embodiments, the targeted therapy that depletes B cells is an anti-CD20 antibody; anti-CD19 antibody; or an anti-BAFF antibody. In some embodiments, the inhibitor of B lymphocyte stimulation is belimumab, tabalumab, or atacicept. In some embodiments, the treatment that reduces levels of anti-nephrin antibodies is or includes plasmapheresis.

In some embodiments, the methods further include obtaining a subsequent sample from the subject; determining a subsequent level of anti-nephrin antibodies in the sample; comparing the subsequent level of anti-nephrin antibodies to a reference level; and (i) if the level of anti-nephrin antibodies in the subsequent sample is above a reference level, the methods can further include continuing to administer the treatment to the subject or administering a different treatment for MCD to the subject, or (ii) if the level of anti-nephrin antibodies in the subsequent sample is below the reference level, the methods can further include discontinuing the treatment.

Additionally, provided herein are methods that include providing a sample from a subject, optionally a subject who has, or who is suspected of having, MCD; and determining a level of anti-nephrin antibodies in the sample.

In some embodiments, the methods further include comparing the level of anti-nephrin antibodies in the sample to a reference level; and providing the level and the reference level to a healthcare provider and/or the subject, and optionally providing the reference range to the healthcare provider, and an indication of whether the subject is above or below the reference level.

Further, provided herein are methods for determining eligibility of a subject who has end stage renal disease (ESRD) for a kidney transplant. The methods include providing a sample from the subject; determining a level of anti-nephrin antibodies in the sample; comparing the level of anti-nephrin antibodies in the sample to a reference level; and identifying a subject who has a level of anti-nephrin antibodies in the sample above a reference level as ineligible for transplant. In some embodiments, the methods further include selecting and optionally administering a treatment that comprises administration of one or more of a glucocorticoid, a treatment that reduces levels of anti-nephrin antibodies, or a treatment that targets B cells, to the subject to the subject; obtaining a subsequent sample from the subject; determining a subsequent level of anti-nephrin antibodies in the sample; comparing the subsequent level of anti-nephrin antibodies to a reference level; and (i) if the level of anti-nephrin antibodies in the subsequent sample is above a reference level, the methods can further include continuing to administer the treatment to the subject or administering a different treatment to the subject, or (ii) if the level of anti-nephrin antibodies in the subsequent sample is below the reference level, the methods can further include identifying the subject as eligible for transplant.

In some embodiments of the methods described herein, the sample comprises renal biopsy tissue, whole blood, plasma, or serum from the subject.

In some embodiments, determining a level of anti-nephrin antibodies in the sample comprises performing Western blot; enzyme linked immunosorbent assay (ELISA); radio-immunoassay (RIA); immunohistochemistry (IHC); immune-precipitation assay; or fluorescent activated cell sorting (FACS).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
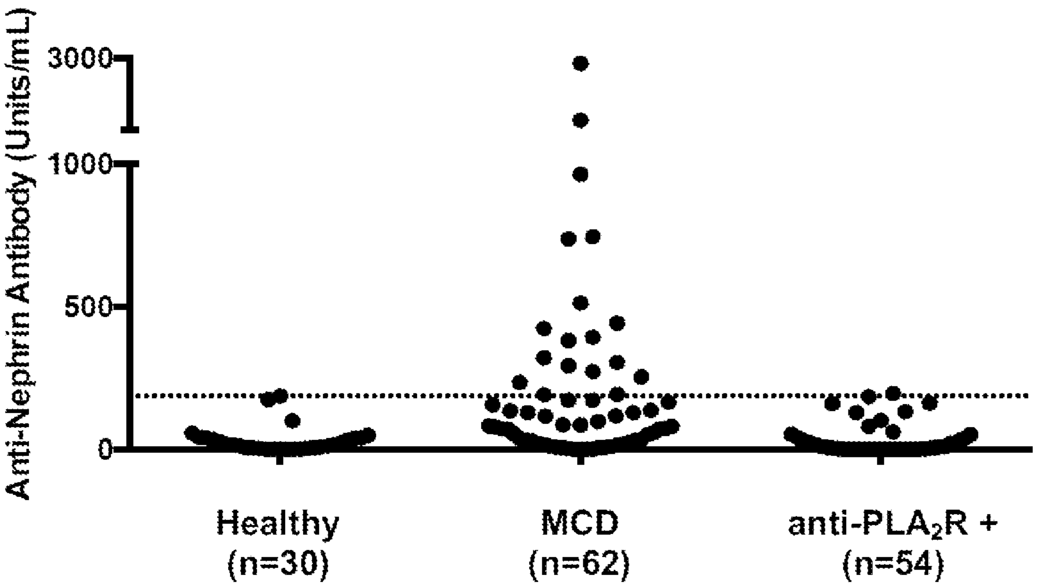
FIGS. 1A-E. Circulating autoantibodies against nephrin are present in a subset of MCD patients from the NEPTUNE study cohort and correlate with disease activity. (A) Antibodies against the extracellular domain of recombinant human nephrin (hNephrinG1059) were measured by indirect ELISA. Antigen specific binding was determined by subtracting the average OD450 nm of duplicate uncoated wells (nonspecific background) from the average OD450 nm of duplicate hNephrinG1059 coated wells for each individual patient sample. A relative antibody titer was then determined from a standard curve that was generated using a single positive patient sample with a 1:100 dilution defined as containing 1000 Units/ml. The threshold for anti-nephrin antibody positivity (187 Units/ml) was defined as the maximum antibody titer, as the cohort was not normally distributed, in a healthy control population (n=30) with no known kidney disease (dotted line) to maximize specificity. The earliest serum sample available during active disease (urine protein-creatinine ratio (UPCR)>3 g/g on the day of sample collection) was positive for anti-nephrin antibodies in 18 (29%) of 62 patients with biopsy proven MCD from the NEPTUNE cohort. 53 (98%) of 54 nephrotic control patients with anti-human phospholipase A2 receptor (hPLA2R+) antibodies, as determined by clinical ELISA and IIFT assays (Euroimmun), were negative for anti-nephrin antibodies. The intra and inter-assay coefficient of variances for the anti-nephrin antibody ELISA were 5.56% and 14.36% respectively. The antibody titer for the NEPTUNE patients and controls are given in Table 2. (B) 11 of the 18 NEPTUNE patients who were anti-nephrin antibody positive during active disease (blue bar) had a subsequent serum sample available during complete remission (UPCR<0.3 g/g on the day of sample collection) which tested anti-nephrin antibody negative (red bar) in all cases. Dotted line indicates threshold for positive antibody titer (187 Units/ml). Student t-test was used to compare differences between the active and remission samples p<0.01, *p<0.001. (C) The same serum samples evaluated by ELISA from the NEPTUNE cohort in (B) were evaluated for their ability to immunoprecipitate nephrin from HGE (derived from non-diseased human kidney). In keeping with the ELISA results, only serum obtained during active disease (indicated by an arrow with an A (blue colored) above it) immunoprecipitated nephrin, whereas serum obtained during remission (indicated by an arrow with an a' above it) did not. Total IgG was comparable between active and remission samples for each patient. (D, E) Kaplan-Meier estimates for complete remission (CR) and relapse-free period in the NEPTUNE cohort. (D) Time to complete remission from enrollment was similar between the anti-nephrin antibody (Ab) positive (median time 4.4 months) and negative groups (median time 5.4 months) by a log rank test (p=0.7288). (E) The relapse-free period following CR was shorter in the anti-nephrin antibody positive group (median time 6 months) compared to the antibody negative group (median time 21.57 months), although this finding did not reach statistical significance by a log rank test (p=0.0945). CR was defined as UPCR<0.3 g/g. Relapse when UPCR>3 g/g after reaching CR.
Figure 1B:
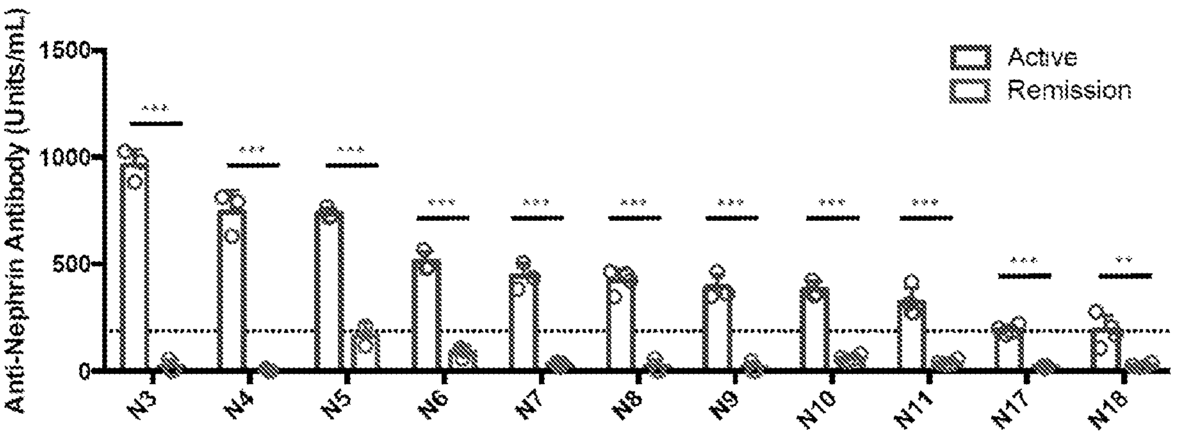

Nephrin is an essential structural component of the SD[2,3], as illustrated by genetic mutations in nephrin (NPHS1) that cause complete lack of nephrin cell surface localization, underlying Congenital Nephrotic Syndrome of the Finnish Type (CNF)[4,5]. In contrast to congenital NS with an established genetic basis, the cause of non-congenital NS in both children and adults remains largely unknown. There is strong evidence supporting immune dysregulation with a potential causative circulating factor, however its identity has remained elusive[6,7]. Glucocorticoids are effective at inducing remission, however relapse, steroid dependence and intolerance are common, often requiring alternative immunosuppressive agents[8]. In those patients with steroid dependent NS who progress to end stage kidney disease (ESKD) and require kidney transplantation, the disease can promptly recur in the allograft[1], a devastating and difficult-to-treat complication.

The recent discovery that anti-CD20 B-cell targeted therapies are effective in children with frequently relapsing or steroid-dependent NS[9-11] and in adults[12] suggests a potential autoantibody-mediated etiology. However, this possibility is hard to reconcile with the traditional view of MCD lacking IgG deposition on renal biopsy[13]. Whilst diffuse podocyte-associated IgG is described in MCD, it is minimal compared to that seen in membranous nephropathy (MN), and given the absence of electron-dense deposits by EM, it is generally attributed to non-specific protein resorption of little significance[14].

Antibodies targeting the essential SD component nephrin have been shown to cause massive proteinuria when administered in animal models[15-17] and when they arise as alloantibodies following kidney transplantation in children with CNF and complete nephrin deficiency[18]. In both animal models[15,16] and cultured podocytes[7,19], anti-nephrin antibodies cause a redistribution of nephrin that is identical to that observed in renal biopsies of patients with NS[20,21]. This redistribution of nephrin away from the SD along with separation of intercellular junctions between adjacent podocytes has long been proposed as a logical concept to explain the proteinuria in these patients; however, the cause of this redistribution remains unknown.

The present inventors hypothesized that autoantibodies against nephrin might underlie non-congenital MCD by interfering with the integrity of the SD complex.

The present invention is based, at least in part, on the discovery of circulating autoantibodies against the extracellular domain of nephrin, the essential constituent of the podocyte SD, in a subset of patients with non-congenital, childhood and adult-onset MCD. These nephrin autoantibodies were specifically present in MCD kidney biopsies, forming distinct clusters together with nephrin. These observations share striking parallels with the autoimmune blistering skin condition pemphigus, in which circulating autoantibodies target the desmosomal cell adhesion molecules desmogleins (dsg), the fundamental structural proteins of the desmosomal cell adhesion complex that links adjacent keratinocytes[22], analogous to nephrin in the specialized SD junctional complex between adjacent podocytes. In pemphigus, these dsg autoantibodies directly interfere with cell adhesion through redistribution, clustering and endocytosis of dsg that disrupts the integrity of the desmosome[22]. Previous reports of experimental anti-nephrin antibody mediated disruption of nephrin homophilic interactions further support this potential mechanism in MCD[3]. Furthermore, pemphigus exhibits a rapid response to glucocorticoid treatment (within days to weeks) that cannot be explained by reduced IgG synthesis alone and may be due to compensatory desmoglein synthesis in keratinocytesa. Similarly, most cases of MCD respond rapidly to glucocorticoids (within weeks) which have also been shown to upregulate nephrin cell surface expression in cultured human podocytes[26]. The present findings indicate that the IgG co-localizing with nephrin in MCD kidney biopsies may represent in situ binding of nephrin autoantibodies. Without wishing to be bound by theory, this targeted binding may be sufficient to disrupt nephrin homophilic interactions leading to early loss of SD integrity, and the redistribution of IgG along with its target nephrin may explain this subtle punctate staining pattern, in contrast to the much more intense staining seen with membranous nephropathy labeling large IgG immune complex aggregates that progressively accumulate along the base of the podocyte foot processes.

Fortunately, progression of MCD to ESKD is rare, however in those patients that do or in those with an initial diagnosis of primary FSGS that progresses more commonly, the disease can rapidly recur in the allograft. A role for nephrin autoantibodies in early post-transplant massive proteinuria is illustrated by a patient with steroid dependent MCD that eventually progressed to ESKD with subsequent biopsies showing FSGS. Early post-transplant massive proteinuria occurred in the presence of circulating nephrin autoantibodies identified both prior to transplantation and at the time of disease recurrence, which were successfully treated with plasmapheresis/rituximab, leading to sustained remission associated with their disappearance. These findings are in keeping with previous studies in CNF patients who develop alloantibodies to nephrin in association with disease recurrence in the allograft and respond to plasmapheresis/rituximab.[19,36] Importantly, the critical distinction is that in this patient, the nephrin autoantibodies were present both prior to the transplant and at the time of disease recurrence whereas in CNF they arise as a direct consequence of the transplant due to alloimmunization to nephrin.[19] FSGS and MCD share some important similarities, such as indistinguishable ultrastructural changes and response to B-cell therapies[37], and together with this illustrative case, we would speculate that our findings of nephrin autoantibodies may also extend to a subset of patients with a diagnosis of primary non-genetic FSGS.

Thus, the present results indicate that B-cell targeted therapy can be used in a subset of NS patients, and provide methods to molecularly identify those patients who stand to benefit most from the targeted therapeutic strategies for anti-nephrin antibody positive NS.

Subjects

The present methods can be used in subjects (e.g., mammals, preferably human or non-human veterinary subjects, including human adults and children) who have, or who are suspected to have, nephrotic syndrome (NS), e.g., who have diffuse podocytopathy with minimal changes (Minimal Change Nephrotic Syndrome, MCNS) or Minimal Change Disease (MCD, also known as lipoid nephrosis or nil disease). Methods for identifying subjects are known in the art; see, e.g., Vivarelli et al., Clin J Am Soc Nephrol. 2017; 12(2):332-345. In some embodiments, the subjects have a urine protein-creatinine ratio (UPCR)>3 g/g, profound proteinuria and oval fat bodies, hypovolemia, hypertension, thromboembolism, hypoalbuminemia (less than 2.5 g/dL in children), hyperlipidemia, and/or facial edema. A critical level for diagnosis in children is the presence of proteinuria of more than 40 $mg/h/m^2$, while a threshold of 3.5 g/d/1.73 $m^2$ is useful in adults. See, e.g., Mansur et al., "Minimal- Change Disease," Mescape, January 2021, available at emedicine.medscape.com/article/243348. The present methods can be used, e.g., in subjects who have not been formally diagnosed, e.g., to aid in diagnosis and/or selection of treatment, or in subjects who have been diagnosed, to aid in selection of treatment.

Recurrent acute nephrotic syndrome in the allograft, referred to as "recurrent focal segmental glomerulosclerosis" (rFSGS) in patients with a history of acute nephrotic syndrome in the native kidney, is morphologically indistinguishable from MCD. Therefore, a study was also included in a transplant patient with an initial diagnosis of MCD in the native kidney which then progressed to FSGS and eventually ESKD. This patient rapidly developed acute and high proteinuria post-transplant consistent with rFSGS, which was not confirmed by a biopsy; however, her pre-transplant serum showed high levels of anti-nephrin antibodies which decreased after aggressive and successful treatment with rituximab and plasmapheresis; this patient went into lasting remission and retained her transplant. Thus, analysis of anti-nephrin antibodies in this group of patients (with a history of acute nephrotic syndrome, who developed FSGS and then ESKD, and are then considered for a transplant) can be helpful in determining prognosis and identifying subjects who either need to be treated to reduce anti-nephrin antibodies (e.g., using rituximab and plasmapheresis) or who should be excluded from transplant eligibility.

Methods of Diagnosis

Included herein are methods for diagnosing subjects with MCD or antibody-mediated acquired idiopathic nephrotic syndrome (INS), and/or for identifying subjects who would benefit from (and in some embodiments should be treated with) certain therapies as described herein, e.g., subjects who have MCD or an acute acquired nephrotic syndrome or FSGS. The methods rely on detection of anti-nephrin antibodies. The methods include obtaining a sample from a subject, and evaluating the presence and/or level of anti-nephrin antibodies in the sample, and comparing the presence and/or level with one or more references, e.g., a control reference that represents a normal level of anti-nephrin antibodies, e.g., a level in an unaffected subject, and/or a disease reference that represents a level of anti-nephrin antibodies associated with MCD, e.g., a level in a subject having MCD. Suitable reference values can include those shown in, or determined as described in, Example 1.

As used herein the term "sample", when referring to the material to be tested for the presence of anti-nephrin antibodies using the methods described herein includes inter alia renal biopsy tissue, whole blood, plasma, or serum; in some embodiments, the methods include testing for the presence of circulating autoantibody in plasma/serum, and then testing in tissue to confirm binding in the biopsy tissue. The type of sample used may vary depending upon the clinical situation in which the method is used. Various methods are well known within the art for the identification of anti-nephrin antibodies in a sample.

The presence and/or level of anti-nephrin antibodies can be evaluated using methods known in the art, e.g., using standard electrophoretic and quantitative immunoassay methods, including but not limited to, Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Kim (2010) Am J Clin Pathol 134:157-162; Yasun (2012) Anal Chem 84(14):6008-6015; Brody (2010) Expert Rev Mol Diagn 10(8):1013-1022; Philips (2014) PLOS One 9(3): e90226; Pfaffe (2011) Clin Chem 57(5): 675-687). The methods typically include revealing labels such as fluorescent, chemiluminescent, radioactive, and enzymatic or dye molecules that provide a signal either directly or indirectly. As used herein, the term "label" refers to the coupling (i.e. physically linkage) of a detectable substance, such as a radioactive agent or fluorophore (e.g. phycoerythrin (PE) or indocyanine (Cy5), to a probe (e.g., a nephrin protein), as well as indirect labeling of the probe (e.g. horseradish peroxidase, HRP) by reactivity with a detectable substance.

In some embodiments, an ELISA method may be used, wherein a surface such as the wells of a mictrotiter plate are coated with nephrin protein antigen. The sample containing or suspected of containing the anti-nephrin antibodies is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

In some embodiments, an IHC method may be used. IHC provides a method of detecting a biological marker in situ. The presence and exact cellular location of the biological marker can be detected. Typically a sample is fixed with formalin or paraformaldehyde, embedded in paraffin, and cut into sections for staining and subsequent inspection by confocal microscopy. Current methods of IHC use either direct or indirect labelling. The sample may also be inspected by fluorescent microscopy when immunofluorescence (IF) is performed, as a variation to IHC.

In some embodiments, the presence and/or level of anti-nephrin antibodies is comparable to the presence and/or level of the protein(s) in the disease reference, and the subject has one or more symptoms associated with MCD, then the subject is diagnosed with MCD. In some embodiments, the subject has no overt signs or symptoms of MCD, but the presence and/or level of one or more of the proteins evaluated is comparable to the presence and/or level of the protein(s) in the disease reference, then the subject has an increased risk of developing MCD. In some embodiments, once it has been determined that a person has MCD, or has an increased risk of developing MCD, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of anti-nephrin antibodies, e.g., a control reference level that represents a normal level of anti-nephrin antibodies, e.g., a level in an unaffected subject or a subject who is not at risk of developing a disease described herein (or a cohort of such subjects), and/or a disease reference that represents a level of anti-nephrin antibodies associated with MCD.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

The predetermined value can depend upon the particular population of subjects (e.g., human subjects) selected. For example, an apparently healthy population will have a different 'normal' range of levels of anti-nephrin antibodies than will a population of subjects which have, are likely to have, or are at greater risk to have, a disorder described herein (e.g., MCD). Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

Methods of Treatment

The methods described herein include methods for the treatment of subjects identified using a method described herein as having a level of anti-nephrin antibodies above a reference level, e.g., having a disorder associated with the presence of anti-nephrin antibodies. In some embodiments, the disorder is MCD. Generally, the methods include administering a therapeutically effective amount of a treatment as described herein, to a subject who has been determined to be in need of such treatment by a method described herein.

As used in this context, to "treat" means to ameliorate at least one symptom of the disorder associated with anti-nephrin antibodies, e.g., MCD. Often, MCD results in elevated urine protein-creatinine ratio (UPCR) (e.g., over >3 g/g), profound proteinuria and oval fat bodies, hypovolemia, hypertension, thromboembolism, hypoalbuminemia (less than 2.5 g/dL in children), hyperlipidemia, and/or facial edema; thus, a treatment can result in a reduction in any of the above and a return or approach to normal urine protein-creatinine ratio (UPCR) (e.g., less than 3 g/g), normal levels of proteinuria and absence of oval fat bodies, normoolemia, normotension, normoalbuminemia (above 2.5 g/dL in children), normal lipid levels, and/or reduction or absence of facial edema. Administration of a therapeutically effective amount of a treatment described herein for the treatment of a condition associated with anti-nephrin antibodies will result in decreased levels of anti-nephrin antibodies.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Treatments that can be used in the present methods include administration of one or more of glucocorticoids (e.g., prednisone, beclomethasone, betamethasone, budesonide, cortisone, dexamethasone, hydrocortisone, triamcinolone, prednisolone, or methylprednisolone) or B-cell targeting therapies (e.g., targeted therapies that deplete B cells, e.g., anti-CD20 antibodies such as rituximab, ocrelizumab, ofatumumab, veltuzumab, ocratuzamab, ibritumomab, obinutuzumab, tositumomab, ublitiximab, TRU-015, or orublituximab; anti-CD19 antibodies such as blinatumomab, coltuximabravtansine, MOR208, MEDI-551, denintuzumabmafodotin, SAR3419 (huB4-DM4), SGN-CD19A, taplitumomabpaptox, XmAb 5871, MDX-1342, AFM11, inebilizumab, tafasitamab, or antibodies described in U.S. Pat. No. 8,691,952 (see, e.g., Naddafi and Davami, Int J Mol Cell Med. 2015 Summer; 4(3): 143-151); or anti-BAFF antibodies such as belimumab as well as inhibitors of B lymphocyte stimulation, such as belimumab or tabalumab; or Atacicept (a human recombinant fusion protein comprising the binding portion of a receptor for both BLyS (B-Lymphocyte Stimulator) and APRIL (A PRoliferation-Inducing Ligand) (see Hartung et al., Ther Adv Neurol Disord. 2010 July; 3(4): 205-216). In some embodiments, the treatments include plasmapheresis (see, e.g., Kaplan, J Clin Apher 28, 3-10 (2013)).

Treatments that reduce levels of anti-nephrin antibodies can also be used in the methods described herein, including plasmapheresis.

In some embodiments, the present methods include determining a level of anti-nephrin antibodies in a sample from a subject who has, or who is suspected of having, MCD. If the level of anti-nephrin antibodies in the sample is above a reference level, the methods can further include identifying the subject as having or at risk of developing MCD, and optionally administering a treatment as described herein, e.g., a glucocorticoid, a treatment that reduces levels of anti-nephrin antibodies such as plasmapheresis, or a treatment that reduces B cells, to the subject.

In some embodiments, the present methods include determining a level of anti-nephrin antibodies in a sample from a subject who has ESRD and is about to undergo a kidney transplant. If the level of anti-nephrin antibodies in the sample is above a reference level, the methods can further include identifying the subject as at risk of developing severe proteinuria and kidney disease after transplant, and optionally administering a treatment as described herein, e.g., a treatment that reduces levels of anti-nephrin antibodies such as plasmapheresis, or a treatment that reduces B cells, to the subject.

Kits

Also provided herein are kits for use in the present methods. The kits can include a nephrin protein probe, e.g., comprising the extracellular domain of nephrin. An exemplary sequence of the extracellular domain of nephrin (aa1-1059) is as follows:

(SEQ ID NO: 1)

```
   1 malgttlras llllgllteg laqlaipasv prgfwalpen ltvvegasve lrcgvstpgs
  61 avqwakdgll lgpdpripgf pryrlegdpa rgefhlhiea cdlsddaeye cqvgrsemgp
 121 elvsprvils ilvppkllll tpeagtmvtw vagqeyvvnc vsgdakpapd itillsgqti
 181 sdisanvneg sqqklftvea tarvtprssd nrqllvceas spaleapika sftvnvlfpp
 241 gppviewpgl deghvragqs lelpcvargg nplatlqwlk ngqpvstawg tehtqavars
 301 vlvmtvrped hgaqlsceah nsvsagtqeh gitlqvtfpp saiiilgsas qtenknvtls
 361 cvskssrprv llrwwlgwrq llpmeetvmd glhgghisms nltflarred ngltltceaf
 421 seaftketfk kslilnvkyp aqklwiegpp egqklragtr vrlvclaigg npepslmwyk
 481 dsrtvtesrl pqesrrvhlg sveksgstfs relvlvtgps dnqakftcka gqlsastqla
 541 vqfpptnvti lanasalrpg dalnltcvsv ssnppvnlsw dkegerlegv aapprrapfk
 601 gsaaarsvll qvssrdhgqr vtcrahsael retvssfyrl nvlyrpeflg eqvlvvtave
 661 qgeallpvsv sanpapeafn wtfrgyrlsp aggprhrils sgalhlwnvt raddglyqlh
 721 cqnsegtaea rlrldvhyap tiralqdpte vnvggsvdiv ctvdanpilp gmfnwerlge
 781 deedqslddm ekisrgptgr lrihhaklaq agayqcivdn gvapparrll rlvvrfapqv
 841 ehptpltkva aagdstssat lhcrargvpn ivftwtkngv pldlqdpryt ehtyhqggvh
 901 sslltianvs aaqdyalftc tatnalgsdq tniqlvsisr pdppsglkvv sltphsvgle
 961 wkpgfdgglp qrfciryeal gtpgfhyvdv vppqattftl tglqpstryr vwllasnalg
1021 dsgladkgtq lpittpglhq psgepedqlp teppsgpsg
```

In some embodiments, the nephrin protein is recombinantly produced and/or is tagged or labelled. The label can include a fluorophore or radiolabel. The tag can include glutathione S-transferase (GST), polyhistidine (e.g., (6×HIS)), c-myc, hemagglutinin, or FLAG™ tag (Kodak, New Haven, Conn.) sequences tags, and can be fused at either the N- or C-terminus of the nephrin protein. The nephrin can be in solution, or can be adsorbed to a surface, e.g., wells of a microtiter plate or on beads, e.g., magnetic or polymeric beads. The kits can include anti-human IgG antibodies to detect anti-nephrin antibodies bound to the nephrin protein probe, and/or anti-nephrin antibodies, e.g., for use as a control or to detect nephrin co-localization with IgG antibodies, e.g., in tissue samples. Optionally the anti-human IgG and/or anti-nephrin antibodies are labelled or are otherwise detectable (e.g., comprises an enzyme or substrate for colorimetric detection). Optionally the kit further includes a secondary antibody that is labelled or otherwise detectable (e.g., comprises an enzyme or substrate for colorimetric detection).

EXAMPLES

The invention is further described in the following examples, which do not limit the scope of the invention described in the claims.

Methods

The following materials and methods were used in the Example, below.

Clinical Samples (Kidney Tissue and Serum/Plasma)

Renal biopsies were independently assessed by collaborating renal pathologists across four institutions: Brigham and Women's Hospital (BWH), Massachusetts General Hospital (MGH), Boston Medical Center (BMC) and the Mayo Clinic. Serum/plasma was obtained from patients attending those institutions as either discarded samples originally collected for clinical analysis (BWH/BMC/Mayo clinic) or archival samples from the Kidney Disease Biobank (courtesy of Dr. Sushrut Waikar, Partners Healthcare, in accordance with Partners Healthcare IRB Approval for patients attending BWH or MGH who were consented for serum/plasma collection at the time of renal biopsy). Histological studies were performed on archival kidney tissue that was received for routine clinical evaluation and included diffuse podocytopathies, other nephrotic conditions, and non-neoplastic renal parenchyma from tumor nephrectomies. Medical record review, histological and serological studies were approved by the respective Institutional Review Boards (IRB) for those institutions. Genetic testing was only performed for the patient with post-transplant recurrent disease but not for the other patients enrolled outside the NEPTUNE cohort.

Similarly, sera were obtained from patients with biopsy proven minimal change disease (MCD) from the Nephrotic Syndrome Study Network (NEPTUNE) longitudinal study[23] during active disease (urine protein creatinine ratio (UPCR) >3 g/g) and where available, in remission. Complete remission was defined as UPCR<0.3 g/g and partial remission as a >50% reduction in proteinuria. Steroid-dependent nephrotic syndrome (SDNS) was defined as SSNS with 2 or more consecutive relapses during tapering or within 14 days of stopping steroids. No specific exclusion criteria were applied.

Healthy control sera were randomly selected from Partners Healthcare Biobank, specifically excluding those subjects with any renal or autoimmune disease. Sera from nephrotic patients were evaluated for anti-hPLA2R antibodies at the MGH Immunopathology laboratory using a commercial enzyme linked immunosorbent assay (ELISA) and indirect immunofluorescence test (IIFT) (Euroimmun). Samples were coded to preserve patient anonymity.

Whole Genome Sequencing of the NEPTUNE Cohort

Whole genome sequencing with a goal median depth of 30× was performed using Illumina Hi-seq. A standard pipeline, Gotcloud, was applied for sequence alignment and variant calling[27,28]. The variant analysis focused on approximately 70 genes implicated in Mendelian NS. To screen pathogenic variants in the 70 previously implicated Mendelian NS genes, we employed a pipeline similar to one that has been previously reported[29]. The pathogenicity variants were ultimately classified according to ACMG standards and guidelines[30]. Analyzed genes: ACTN4, ADCK4, ALG1, ANLN, ARHGAP24, ARHGDIA, AVIL, CD151, CD2AP, CDK20, CFH, COL4A3, COL4A4, COL4A5, COQ2, COQ6, CRB2, DGKE, DLC1, EMP2, FAT1, HNF1B, IL15RA, INF2, ITGA3, ITGB4, ITSN1, ITSN2, JAG1, KANK1, KANK2, KANK4, LAGE3, LAMB2, LMX1B, MAGI2, MTTL1, MYH9, MYO1E, MYO5B, NEIL1, NPHS1, NPHS2, NUP107, NUP205, NUP93, NXF5, OCRL, OSGEP, PAX2, PDSS2, PLCE1, PMM2, PODXL, PTPRO, SCARB2, SGPL1, SMARCAL1, TNS2, TP53RK, TPRKB, TRPC6, TTC21B, UMOD, WDR73, WT1, XPO5, ZMPSTE24.

Human Glomerular Extract

Human glomerular extract (HGE) was prepared as previously described by Beck et al[31]. Briefly, glomeruli were isolated from human kidneys deemed non-suitable for transplantation (that had been authorized for use in medical research) obtained from New England Donor Services, by graded sieving followed by isolation of glomerular proteins in RIPA buffer (Boston BioProducts). IgG was pre-cleared from tissue lysate by incubation with Protein G Plus agarose beads (Santa Cruz). Only kidneys with less than 20% global glomerulosclerosis, on routine wedge biopsy, were used for glomerular isolation.

Routine Renal Biopsy Processing

After biopsy acquisition, renal cortex was immediately allocated for light (10% neutral-buffered formalin), immunofluorescence (Zeus transport media) and electron microscopy (Karnovsky's fixative) processing. For routine clinical immunofluorescence, 4 μm cryosections were fixed in 95% ethanol for 10 minutes and incubated with FITC-conjugated polyclonal rabbit $F(ab)_2$ anti-human IgG antibody (Dako; F0315) diluted 1:20. FITC-conjugated sheep anti-human IgG1, IgG2, IgG3, IgG4 (Binding Site; AF006, AF007, AF008, AF009, respectively) diluted 1:20 were used for IgG subclass evaluation. Albumin was detected using FITC-conjugated polyclonal rabbit anti-human albumin (Dako; F0117) diluted 1:30. Sections were mounted using Dako fluorescence mounting medium (Dako; S3023) with a #1.5 coverslip. Immunofluorescence images were acquired on an Olympus BX53 microscope with an Olympus DP72 camera at 150 ms exposure.

Confocal Microscopy

For confocal microscopy, 4 μm cryosections of human kidney biopsies were fixed in 95% ethanol for 10 minutes and subsequently blocked for one hour at room temperature (RT) with phosphate buffer saline (PBS) supplemented with 0.2% fish gelatin, 2% bovine serum albumin (BSA) and 2% fetal bovine serum (FBS). All antibodies were diluted in this blocking solution and incubated for one hour at RT. Nephrin was detected using 1 μg/ml primary polyclonal sheep anti-human nephrin (R&D systems; AF4269) followed by a secondary AlexaFluor™ 568-conjugated donkey anti-sheep IgG (Invitrogen; A21099). Synaptopodin was detected using anti-synaptopodin (N-terminus) guinea pig polyclonal anti-serum (Progen; GP94-N) diluted 1:1000 followed by a secondary AlexaFluor™ 568-conjugated goat anti-guinea pig IgG (Invitrogen; A11075) antibody. Podocin and Wilms Tumor 1 (WT1) were detected using a primary polyclonal rabbit anti-human podocin (Millipore Sigma; P0372) and a primary monoclonal rabbit anti-human WT1 clone SC06-41 (Invitrogen; MA5-32215) diluted 1:500 and 1:300 respectively, followed by a secondary AlexaFluor™ 568-conjugated donkey anti-rabbit IgG (Invitrogen; A10042). IgG immune deposits were detected using a primary monoclonal mouse anti-human IgG antibody (Abcam; ab200699) diluted 1:750 followed by a secondary AlexaFluor™ 488-conjugated donkey anti-mouse IgG (Invitrogen; A21202). All secondary AlexaFluor™-conjugated antibodies were diluted 1:500. Sections were mounted using Vectashield anti-fade mounting medium (Vectashield, H-1000) with a #1.5 coverslip and images were acquired on a Leica TCS SPE microscope.

Structured Illumination Microscopy (SIM)

Structured Illumination Microscopy (SIM) imaging was performed on 4 μm fixed, frozen human kidney biopsy sections processed according to the aforementioned protocol for confocal microscopy. All images were collected using an OMX V4 Blaze (GE Healthcare) microscope equipped with three watercooled PCO.edge sCMOS cameras, 488 nm, 568 nm laser lines, and 528/48 nm, 609/37 nm emission filters (Omega Optical). Images were acquired with a 60×/1.42 Plan-Apochromat objective lens (Olympus) with a final pixel size of 80 nm. Z stacks of 4-8 μm, were acquired with a 0.125 μm z-spacing, and 15 raw images (three rotations with five phases each) were acquired per plane. Spherical aberration was minimized for each sample using immersion oil matching[24]. Super resolution images were computationally reconstructed from the raw data sets with a channel-specific, measured optical transfer function, and a Wiener filter constant of 0.001 using CUDA-accelerated 3D-SIM reconstruction code[32]. Axial and lateral chromatic misregistration was determined using a single biological calculation slide, prepared with human kidney tissue stained with a primary mouse anti-human IgG monoclonal antibody (Abcam; ab200699) followed by both secondary AlexaFluor™ 488-conjugated donkey anti-mouse IgG (Invitrogen; A21202) and AlexaFluor™ 568-conjugated goat anti-mouse IgG (Invitrogen; A11031) antibodies on the same tissue cryosection. Experimental data sets were then registered using the imwarp function in MATLAB (MathWorks) 33.

Generation of Recombinant Human Nephrin and Phospholipase $A_2$ Receptor ($PLA_2R$)

Separate plasmids encoding the extracellular subdomains of human nephrin (amino acids 1-1059), comprising the 8 Ig-like C2-type domains and a single fibronectin type III domain, and human phospholipase A2 receptor (hPLA2R), comprising the N-terminal ricin domain, fibronectin type II domain and 8 C-type lectin domains (CTLD), both with C-terminal polyhistidine (6×HIS) tags, were generated by standard cloning techniques. The correct sequences were confirmed by whole plasmid sequencing (MGH DNA core). HEK293-F cells (Thermo Fisher) were transfected with 0.5 μg plasmid per $10^6$ cells using 1.5 μg PEI (polyethylenimine). The plasmid and PEI were pre-incubated for 20 mins in Freestyle media (Thermo Fisher) at one tenth the final volume and then added dropwise to the cells. After 3-5 days, provided the cell viability was >95%, the cell culture media was harvested by centrifugation (300×g for 10 mins). Imidazole was added to a final concentration of 10 mM and the media was filter sterilized (0.2 μm) on ice. Nickel NTA resin (Qiagen) was washed 3× with 10 mM Imidazole in PBS and then incubated with the filtered media overnight at 4° C. on a roller mixer (Thermo Fisher). The Nickel NTA resin was then washed 3× with 10 mM Imidazole in PBS and the recombinant proteins were eluted with 300 mM Imidazole in PBS. The purity of the eluted fractions was confirmed by SDS-PAGE with a 4-12% Bis-Tris gel (Invitrogen), pooled together and concentrated to 1 ml using an Amnicon centrifugation filter with a 10K molecular weight cut off (Millipore). The resultant protein was run over a Sephadex™300 column and 0.5 ml fractions were collected. The purity of the eluted fractions was confirmed by SDS-PAGE on a 4-12% Bis-Tris gel (Invitrogen) and the concentration determined by measuring absorbance at 280 nm using a Nanodrop spectrophotometer (Thermo Fisher). Immunoreactivity of the purified nephrin was confirmed by Western blot analysis, under reducing conditions using a primary sheep anti-human nephrin antibody (R&D) followed by a secondary HRP-conjugated donkey anti-sheep IgG antibody (Jackson immunoresearch), and of the purified $hPLA_2R$ under non-reducing conditions using serum from a patient with known anti-$PLA_2R$ antibodies (determined by commercial ELISA and IIFT (Euroimmun)) diluted 1:1000 and a secondary HRP-conjugated donkey anti-human IgG antibody (Jackson Immunoresearch).

Enzyme Linked Immunosorbent Assay (ELISA)

Nunc MaxiSorp™ ELISA plates (Thermo Fisher) were coated with either 1 μg/ml recombinant extracellular domain of human nephrin or hPLA2R diluted in coating buffer (Biolegend) and incubated O/N at 4° C. Uncoated control wells were used to determine non-specific binding (in the absence of antigen) for each patient sample and this allowed for background subtraction. The plates were washed 3× with 300 μl PBS+ 0.05% TWEEN® 20 nonionic surfactant (PBST). Plates were blocked with 300 μl of SUPERBLOCK™ blocking buffer (Thermo Fisher) for 1 hr at RT and then incubated O/N at 4° C. with 100 μl of patient samples diluted 1:100 in SUPERBLOCK™ blocking buffer containing 0.1% TWEEN® 20 nonionic surfactant (SuperT). Samples with an initial high titer were subsequently diluted to 1:200 or 1:400. Plates were washed a further 5× with 300 μl of PBST, followed by incubation with 100 μl of biotin-conjugated goat anti-human IgG Fc, highly x-absorbed antibody (Thermo Fisher) diluted to 0.75 μg/ml in SuperT, shaking at 500 r.p.m for 1 hr at RT. Plates were washed 5× with PBST followed by incubation with 100 μl of HRP-conjugated avidin (Biolegend) diluted to 1:2000 in SuperT, shaking at 500 r.p.m for 30 min at RT. Following 5 final washes with PBST, 100 μl of tetramethyl benzidine (TMB) substrate (Biolegend) was added and the plates incubated for 10 min at RT. 100 μl of stop solution (Biolegend) was added and the absorbance at 450 nm was measured. Background subtraction was performed by subtracting the average OD of duplicate uncoated wells from the average OD of duplicate antigen coated wells for each individual patient sample[34]. Anti-nephrin antibody titers were then determined using a standard curve derived from a serial two-fold dilution series of a positive patient sample (MCD15+) in which a 1:100 dilution was arbitrarily defined as containing 1,000 units/ml.

Immunoprecipitation and Western Blot 1 volume of patient serum or plasma was mixed with 5 volumes of RIPA buffer containing HGE, or 100 ng recombinant extracellular domain of human nephrin, and incubated overnight (O/N) at 4° C. IgG-antigen complexes were precipitated with Protein G plus agarose beads (Santa Cruz) for 2 hours at 4° C. The beads were collected by centrifugation and washed 3 times with Tris buffered saline supplemented with 0.2% TWEEN®-20 nonionic surfactant (TBST) and a final wash with distilled water. Proteins were eluted from the beads and denatured under reducing conditions by heating at 95° C. for 5 mins in 1× Laemmli buffer (Biorad) containing 2.5% beta-mercaptoethanol. Samples were loaded into precast 7.5% Mini Protean Tris-glycine gels (Biorad) and electrophoresed at 100V for 90 minutes in the presence of Novex Tris-glycine-SDS running buffer (Thermo Fisher). Proteins were transferred to polyvinylidene fluoride (PVDF) membranes (EMD Millipore) using the PIERCE™ Power Blotter system (Thermo Fisher) for 10 mins at 25V, 1.3A. Membranes were blocked for one hour at RT in TBST containing 5% skimmed milk (w/v) followed by incubation O/N at 4° C. with 1 μg/ml polyclonal sheep anti-human nephrin antibody (R&D systems; AF4269) diluted in TBST with 2% skimmed milk (w/v). All other antibodies were diluted in TBST containing 5% skimmed milk and incubated for one hour at RT. Membranes were washed with TBST 3 times for 5 minutes each, followed by a secondary horseradish peroxidase (HRP)-conjugated donkey anti-sheep IgG antibody (Jackson Immunoresearch; 713-035-147) diluted 1:20,000. Human IgG heavy chain was detected using HRP-conjugated donkey anti-human IgG antibody (Jackson Immunoresearch; 709-035-149) diluted 1:10,000. Finally, membranes were washed 3 times with TBST and incubated with SUPERSIGNAL™ West PICO PLUS or FEMTO chemiluminescent substrate (Thermo Fisher) for 3 minutes and images were acquired on a Universal Hood III gel dock system (Biorad).

Clinical Case Details

Figure 5A:
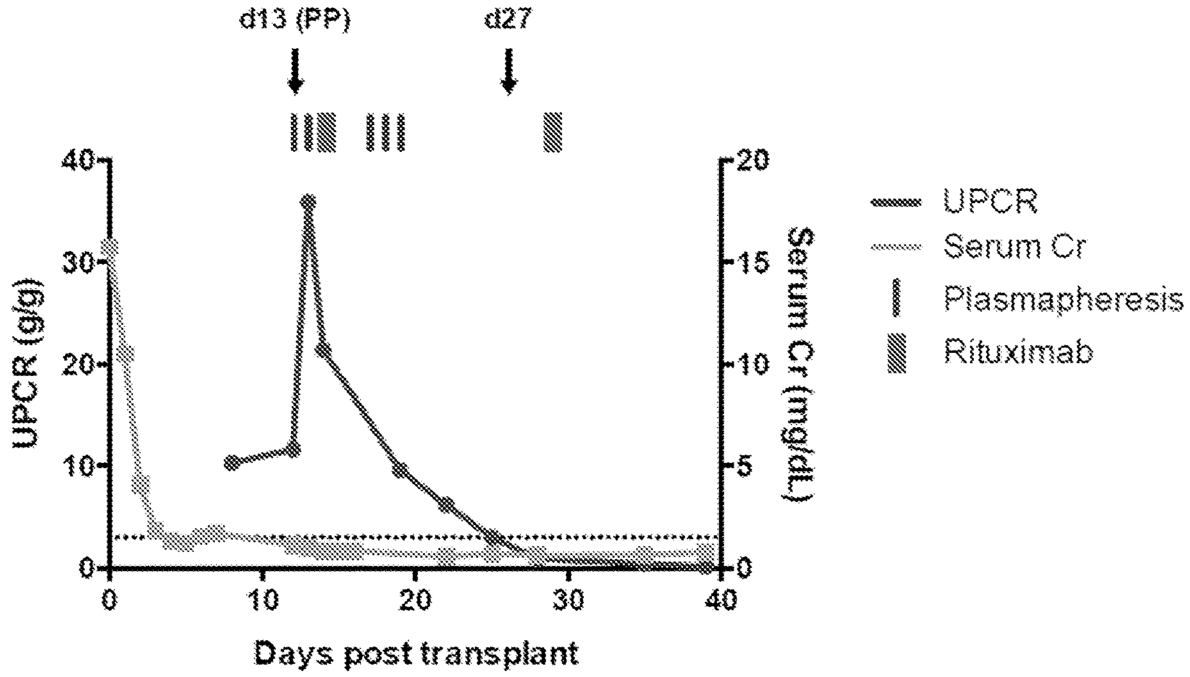
FIGS. 5A-C. High levels of pre-transplant anti-nephrin antibodies are associated with early massive post-transplant proteinuria recurrence. (A) Clinical course of a patient with childhood onset, steroid dependent MCD that progressed to ESKD with subsequent biopsies showing FSGS. The patient developed early, massive proteinuria recurrence, following a cadaveric, pediatric donor kidney transplant that rapidly responded to treatment with plasmapheresis and rituximab shown above the graph. (B) Two pre-transplant serum samples (day −617, day −528) and the initial plasmapheresate (shaded box) (d13 (PP), indicated by arrow on (A)) tested positive by ELISA for anti-nephrin antibodies (dotted line indicates threshold for positivity of 187 U/ml). Serum samples evaluated following treatment response at d27 (d27, indicated by arrow in (A)) and d365 (UCPR<0.3 g/g) were negative for anti-nephrin antibodies. (C) Similarly, the pre-transplant serum and plasmapheresate immunoprecipitated nephrin from HGE (derived from disease free human kidneys) in keeping with the ELISA findings.
Figure 5B:
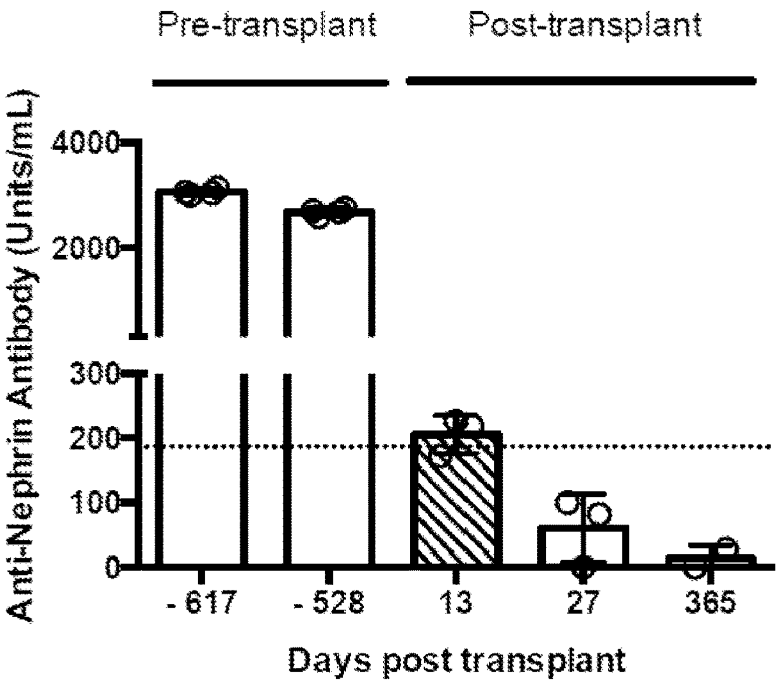
Figure 5C:
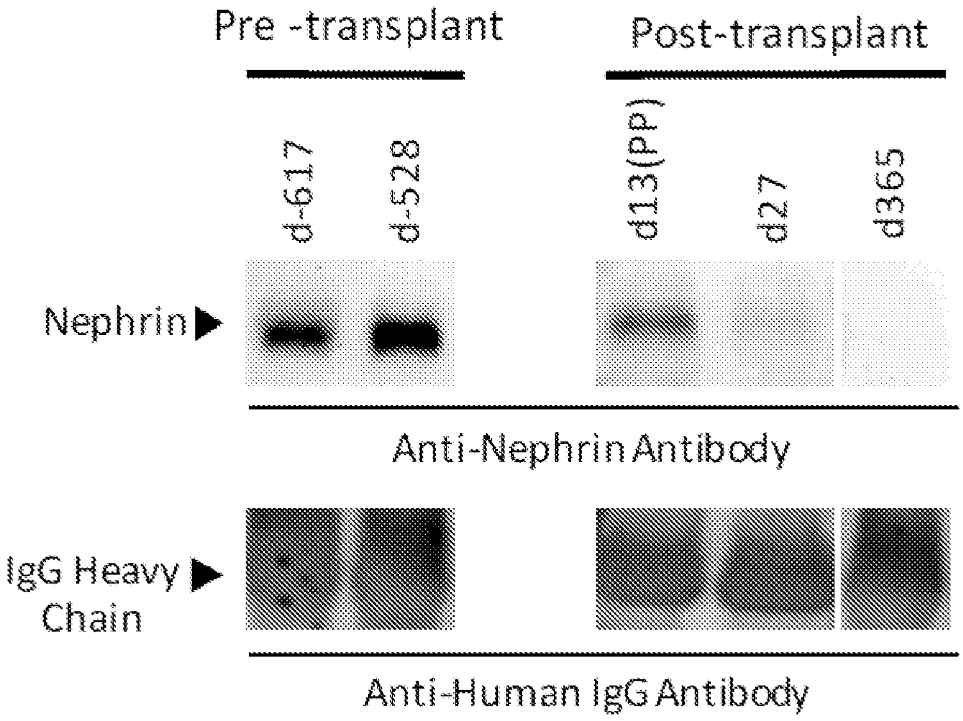
Figure 6A:
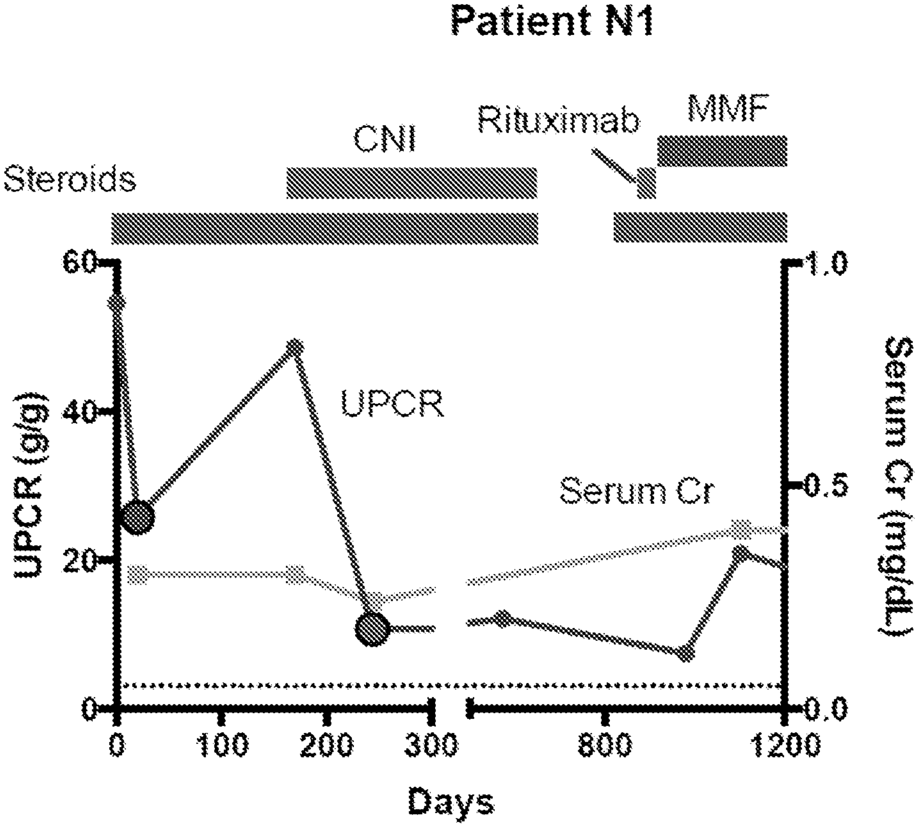
FIGS. 6A-C. Clinical and anti-nephrin antibody data for a single patient from the NEPTUNE cohort with active proteinuria and a partial response to therapy. (A) Clinical course of patient with a serum sample available during active disease (large gray circle with black border at about 10 d) and partial remission (large circle with black border at about 240 d) showing UPCR (g/g) (dotted line indicates UPCR of 3 g/g), serum creatinine (Cr) and treatment (shown above graph). (B) Significant reduction in anti-nephrin antibody titers associated with partial remission (*p=0.01) (dotted line indicates threshold for positive antibody titer of 187 U/ml based on a healthy control population). (C) The serum samples taken on day 20 (d20) and day 244 (d244) both immunoprecipitated nephrin from HGE derived from disease-free human kidneys, with the band intensity mirroring the antibody titers by ELISA. Days; days following enrollment. Partial remission was defined as a >50% reduction in UPCR between samples.
Figure 6B:
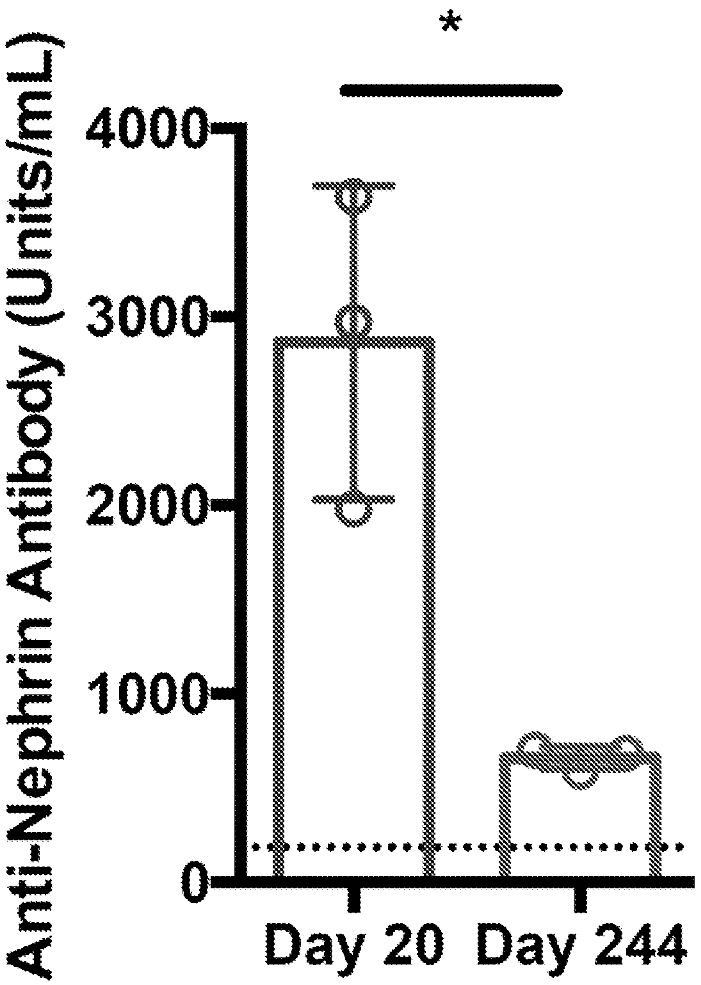
Figure 6C:
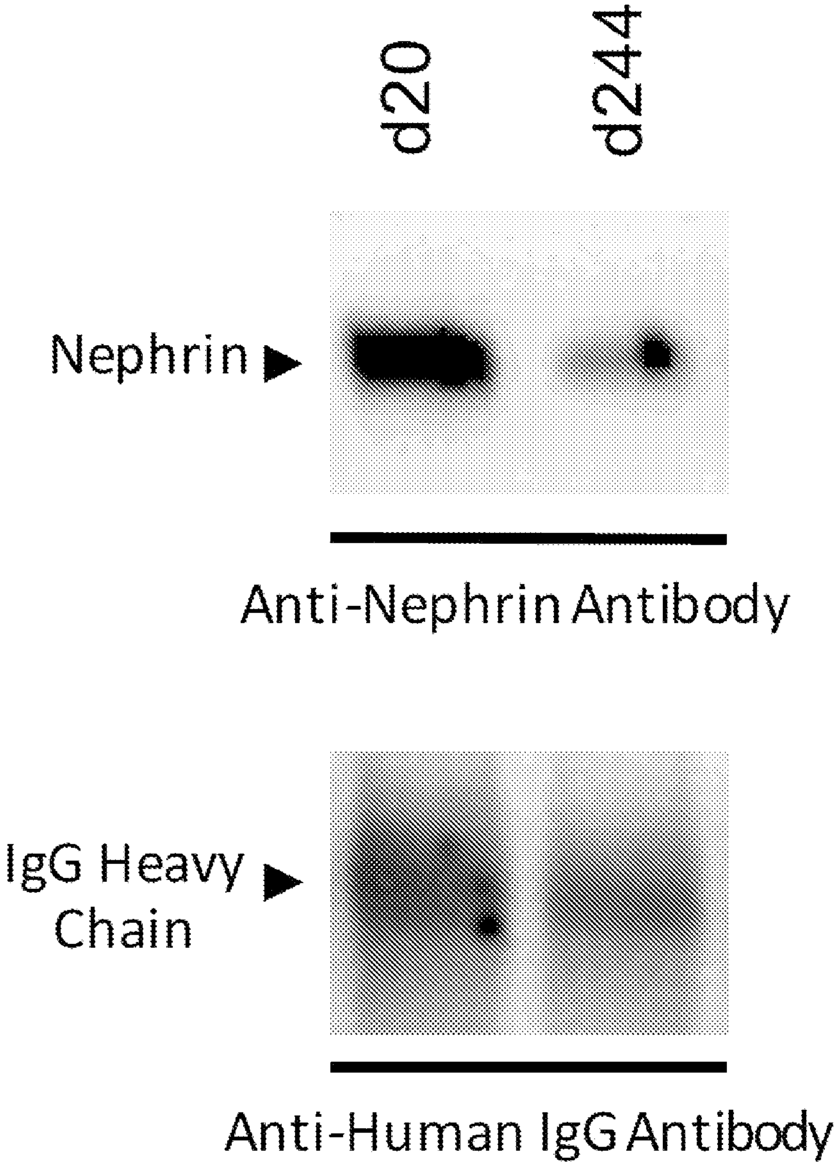

To illustrate a potential role of pre-transplant, nephrin autoantibodies in early massive post-transplant proteinuria recurrence, we present the case of a 27-year-old woman with an initial diagnosis of steroid-responsive MCD at age 2 who became steroid dependent (SDNS), and eventually progressed with subsequent biopsies showing FSGS. Importantly, clinical whole exome sequencing (Prevention Genetics) found no known NS disease causing variants. She eventually developed ESKD and initially underwent hemodialysis for 5 years and then received a pediatric deceased donor kidney (cold ischemia time 19 hours) with immediate graft function (FIG. 5A). Calculated panel reactive antibodies (cPRA) were zero and induction therapy consisted of basiliximab with maintenance therapy of mycophenolate mofetil, tacrolimus and prednisolone. In the setting of early massive post-transplant proteinuria recurrence, associated with lower limb edema, she was treated with five episodes of plasmapheresis (×5) and two doses of rituximab. Her proteinuria rapidly improved and she did not require an allograft biopsy (FIG. 5A). Two serum samples obtained 17 and 20 months prior to the transplant, together with the first plasmapheresate sample obtained during treatment for the post-transplant proteinuria recurrence, all tested positive for anti-nephrin antibodies by ELISA (FIG. 5B) and immunoprecipitated nephrin from healthy human kidney derived HGE (FIG. 5C). Serum samples evaluated following treatment response at day 27 and during complete remission at 1 year post transplant both tested negative for nephrin autoantibodies by ELISA (FIG. 5B).

Example 1. Discovery of Autoantibodies Targeting Nephrin in Minimal Change Disease Supports a Novel Autoimmune Etiology To first determine whether circulating autoantibodies against nephrin are detectable in the serum of patients with biopsy proven MCD and no known genetic basis (lacking known pathogenic variants in established Mendelian NS genes), we evaluated serum obtained from the Nephrotic Syndrome Study Network (NEPTUNE) longitudinal cohort study[23] consisting of 41 (66%) children and 21 (34%) adults (Table 2). We developed an indirect enzyme-linked immunosorbent assay (ELISA) using a recombinant, affinity purified extracellular domain of human nephrin ($hNephrinG_{1059}$) and established a threshold for anti-nephrin antibody (ab) positivity, based on the maximum titer in a healthy control population (n=30) (FIG. 1A). Evaluation of the earliest serum sample obtained during active disease (urine protein to creatinine ratio, UPCR>3 g/g) revealed that 18 (29%) of 62 patients, with an equal number of adults and children, were positive for autoantibodies against nephrin (FIG. 1A). Control sera from 53 (98%) of 54 patients who tested positive for anti-$hPLA_2R$ antibodies, by clinically validated ELISA and indirect immunofluorescence test (IIFT) assays, were negative for anti-nephrin ab (FIG. 1A).

The patients' clinical characteristics (Table 1) and the median time from enrollment to complete remission (CR) were similar between the anti-nephrin ab positive and negative groups (4.4 months vs 5.4 months respectively; p=0.7288) (FIG. S2). However, the relapse-free period was shorter for the anti-nephrin ab positive group compared with the ab negative group, although this finding did not reach conventional levels of statistical significance (median time to relapse 6.0 months vs 21.57 months respectively; p=0.0945).

Figure 1C:
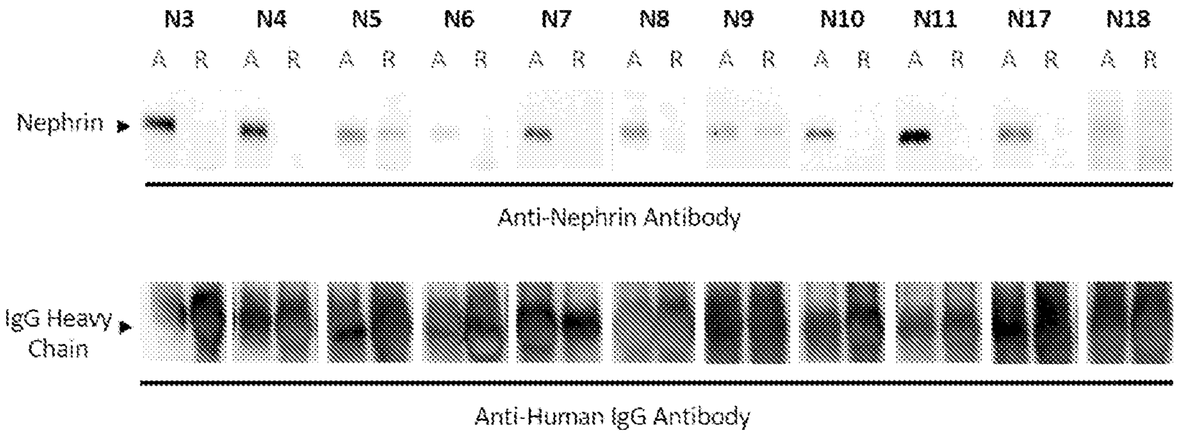
Figure 1D:
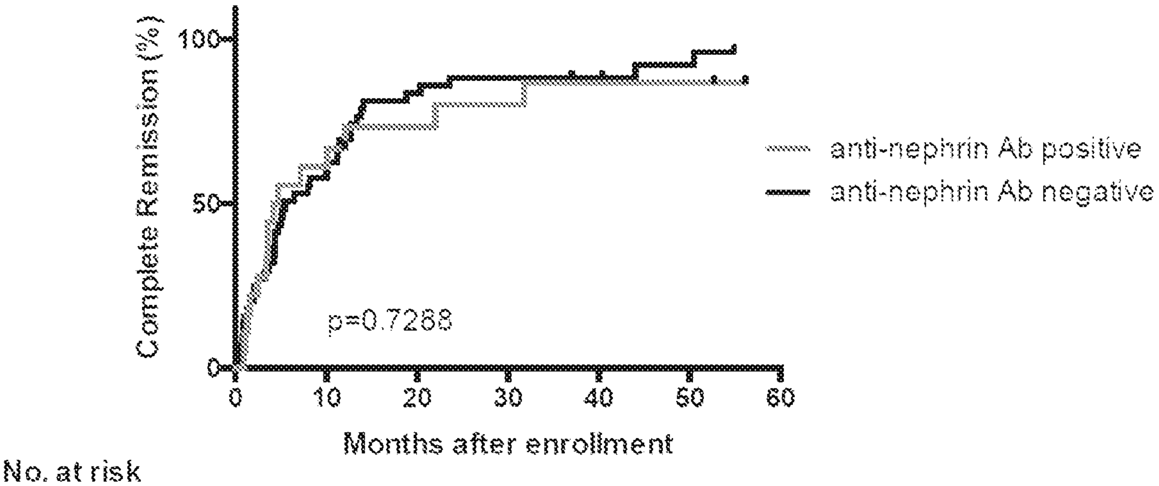
Figure 1E:
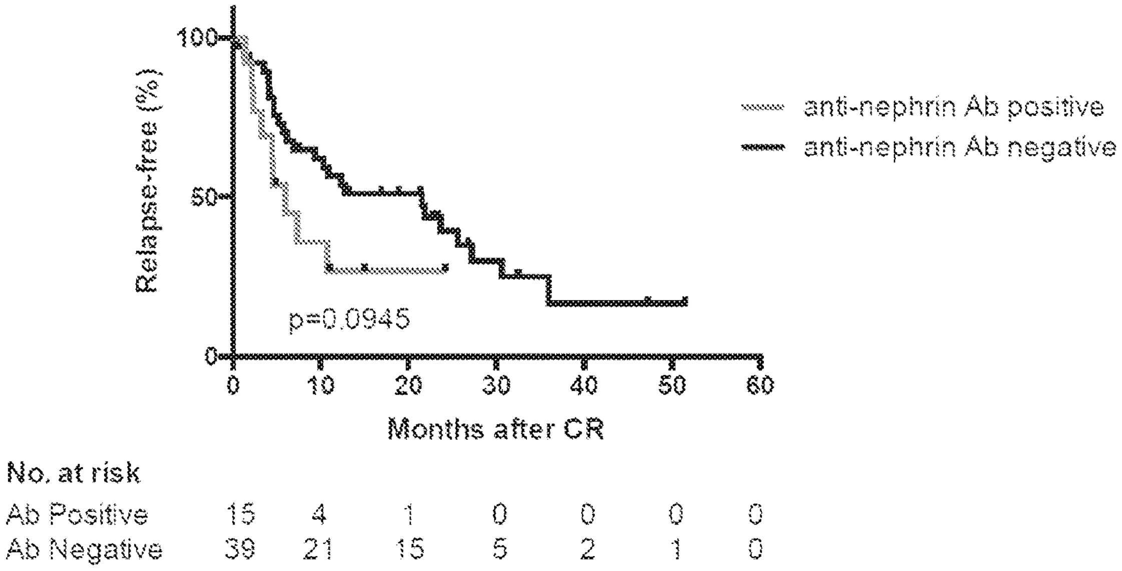

A subsequent serum sample was available during either complete (UPCR<0.3 g/g) or partial remission (>50% reduction in proteinuria) from 12 of the 18 anti-nephrin ab positive patients, in whom we observed a complete absence or a significant reduction of nephrin autoantibodies respectively (FIG. 1B, FIGS. 6A-C). In keeping with the ELISA results, only serum obtained during active disease or partial remission immunoprecipitated nephrin from healthy donor kidney derived human glomerular extract (HGE), whereas serum obtained during complete remission did not (FIG. 1C).

To further investigate a potential pathogenic role of these nephrin autoantibodies, we next sought to establish whether they are present within kidneys of patients with MCD. One limitation of the NEPTUNE cohort is that biopsy material from these patients was not available for further evaluation and so we turned to our own institution and collaborators for biopsy and serum samples.

Figure 2A:
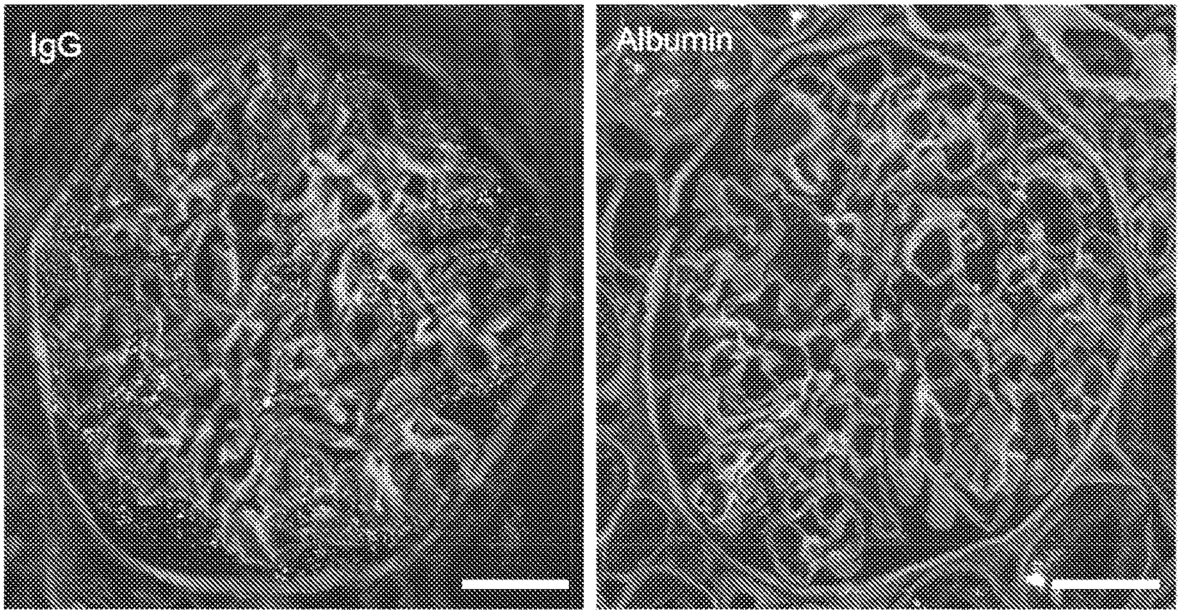
FIGS. 2A-C. Routine clinical epifluorescence microscopy, Periodic Acid Schiff (PAS) stained light microscopy and electron microscopy (EM) images of IgG-positive MCD (MCD7+). (A) The diffuse punctate staining seen with FITC-conjugated IgG antibody is not seen by albumin staining. Note the positive albumin staining in proximal tubule reabsorption droplets. (B) Staining for IgG subtypes confirms no restriction of the punctate staining, and, in this case, more immunoreactivity for IgG1 and IgG2 compared to IgG3 and IgG4 subtypes was observed. (C) Staining for Kappa and Lambda light chains shows equal intensity and an appearance mirroring the IgG staining. PAS staining shows minimal light microscopic changes and EM demonstrates diffuse podocyte foot process effacement. Scale bars IF and PAS: 20 μm. Scale bar EM: 1 μm.
Figure 2B:
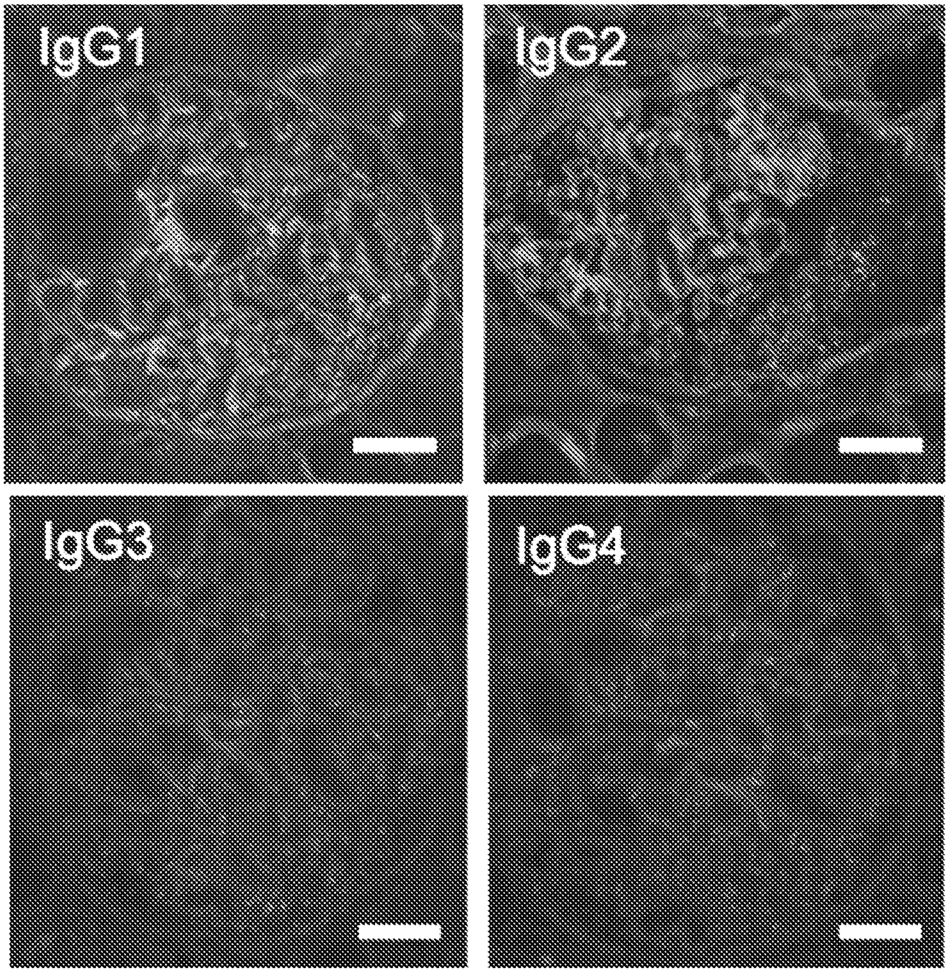
Figure 2C:
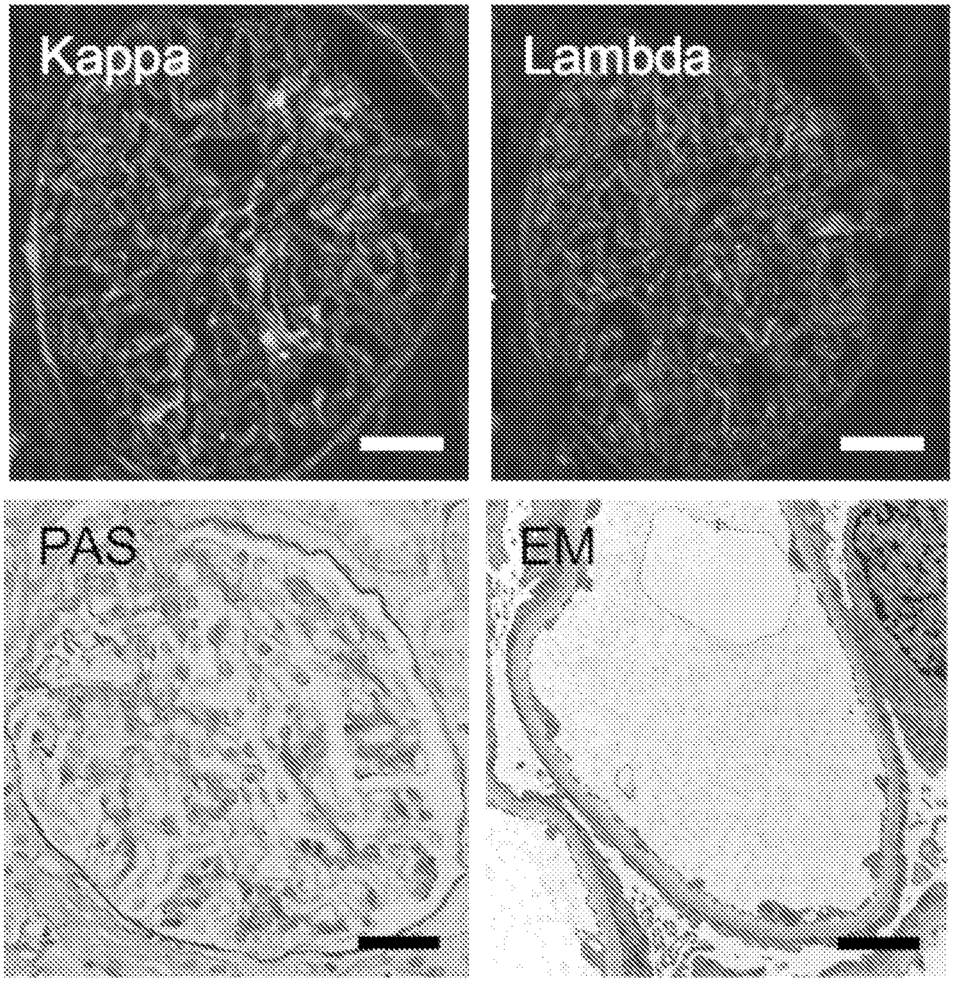
Figure 7A:
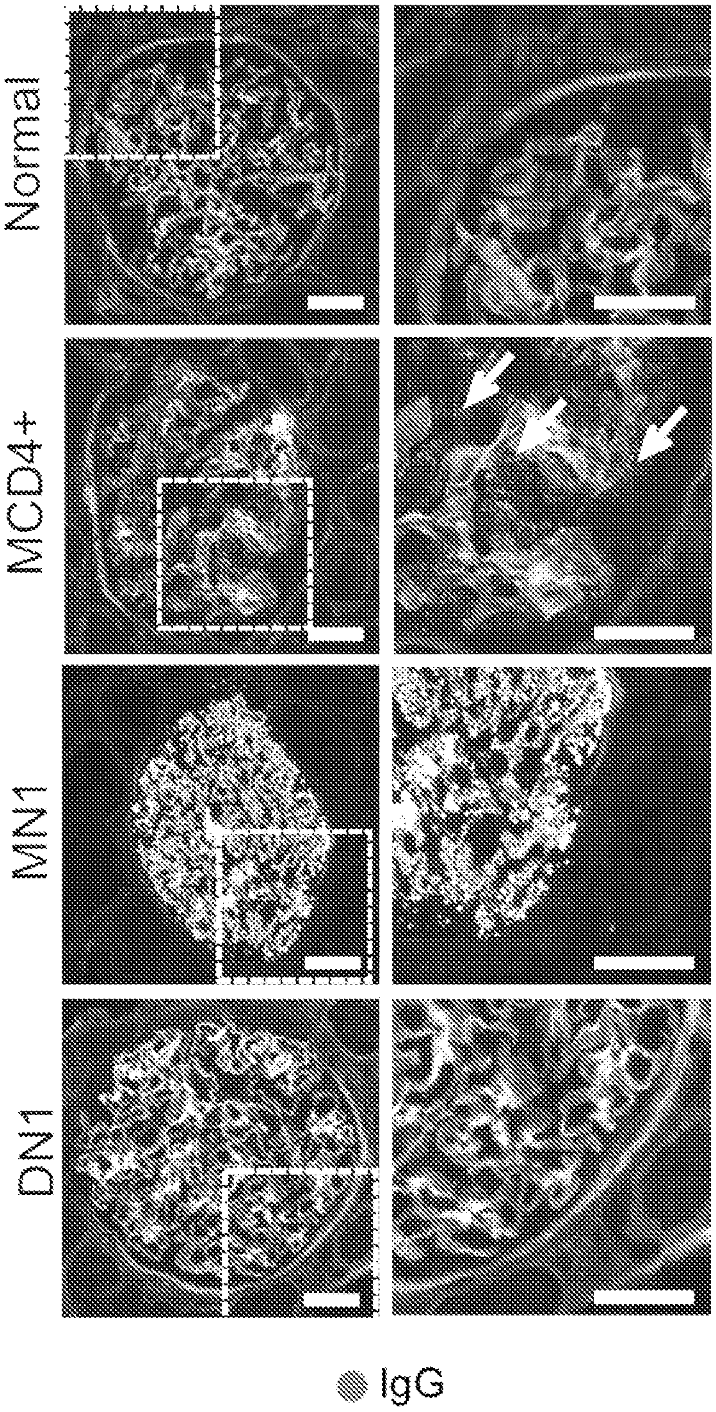
FIGS. 7A-C. Immunofluorescence microscopy images of IgG, IgG/Nephrin and IgG/Synaptopodin staining. (A) Clinical epifluorescence images of glomeruli stained for IgG using FITC-conjugated anti-human IgG $(Fab)_2$ antibodies (ab). Right panel shows larger magnification of dotted square. A normal glomerulus shows low intensity linear staining along all basement membranes. In a subset of MCD (here shown MCD4+), a delicate punctate staining for IgG is observed in the extracapillary compartment, closely associated with GBMs (white arrows). In contrast, granular IgG staining in MN (here shown MN1) is of much stronger intensity. No granular or punctate staining is observed in other proteinuric conditions, including in patients with DN (here shown DN1). (B) Confocal microscopy images of the same cases stained for IgG and nephrin using primary unconjugated mouse anti-human IgG and sheep anti-human nephrin antibodies. Right panel shows larger magnification of dotted square. While reduction of nephrin staining intensity can be seen in all proteinuric conditions, co-localization of IgG with nephrin is only observed in MCD+(white arrows). (C) Confocal microscopy images of same cases stained for IgG and synaptopodin using primary unconjugated mouse anti-human IgG and guineapig anti-human synaptopodin antibodies. Right panel shows larger magnification of dotted square. No appreciable co-localization of IgG staining with the intracellular actin-associated synaptopodin is seen in the normal kidney, MCD+, MN or DN. Scale bars: 20 μm.

For many years, we have observed a delicate punctate staining for IgG in a subset of patients with MCD (MCD+) by routine immunofluorescence staining that is distinct from the background (FIG. 7A). It is much more subtle when compared to the prominent IgG staining observed in MN (FIG. 7A), and while this feature has been previously described[14], its significance has not been fully established. We therefore hypothesized that this subtle IgG may represent autoantibodies targeting nephrin. To limit the possibility of staining artifacts, we routinely use a directly conjugated FITC anti-huma IgG $F(ab)_2$ ab that we have independently validated with a distinct unconjugated anti-human IgG ab, an anti-light chain ab and isotype specific anti-IgG abs that all show an identical staining pattern (FIGS. 2A-C). Importantly, we observed a complete lack of concurrent glomerular albumin staining, indicating that this feature is IgG selective and does not reflect non-specific protein resorption (FIGS. 2A-C).

Figure 3A:
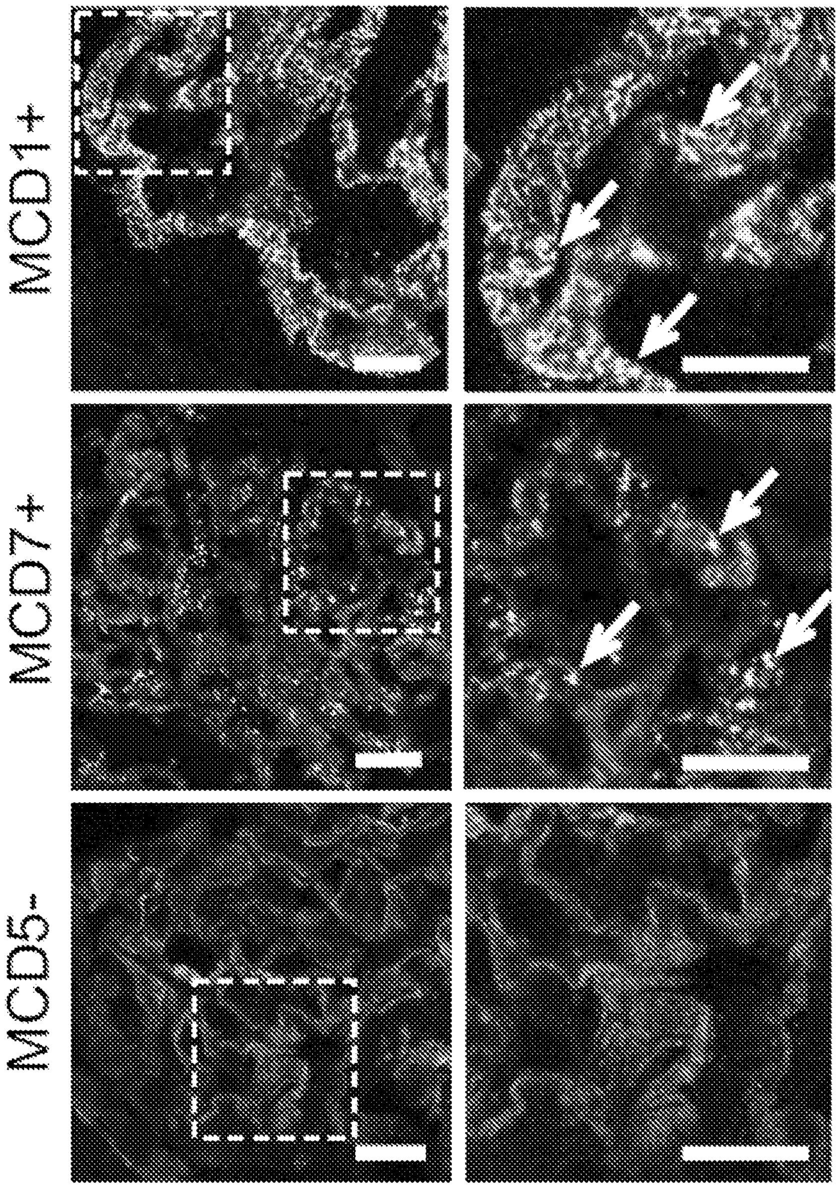
FIGS. 3A-D: Renal biopsy imaging studies in patients with biopsy proven MCD. (A) Representative confocal microscopy images of glomeruli in IgG-positive MCD (MCD1+/MCD7+) and IgG-negative MCD (MCD5−), stained for IgG and the podocyte slit-diaphragm protein nephrin (red). There is a clear overlap (yellow) between IgG and nephrin specifically with the punctate IgG and not background as seen in the MCD+ biopsies (MCD1+/MCD7+) (white arrows) but not in MCD-biopsies. The right panels show magnified images of boxed areas of MCD1+ and MCD7+ biopsies. Scale bar: 10 μm. (B) Representative confocal microscopy images of glomeruli in IgG-positive MCD (MCD1+/MCD7+) and IgG-negative MCD (MCD5−), stained for punctate IgG (indicated with white arrow) and the cytoskeletal podocyte marker synaptopodin (red). There is no appreciable overlap between IgG and Synaptopodin in any of those cases. The right panels show magnified images of boxed areas of MCD1+ and MCD7+ biopsies. Scale bar: 10 μm. (C) Super Resolution Structured Illumination Microscopy (SIM) images of 0.125 mm individual Z-slices showing en face views of the podocyte junction from a representative renal biopsy (MCD1+) in which the nephrin remains GBM-associated, forming a curvilinear pattern. The left image shows co-localization (yellow) of IgG with the slit diaphragm protein nephrin (red), in contrast to mutual exclusivity with the foot process associated synaptopodin shown in the right image, indicating intimate spatial association with nephrin along the podocyte slit diaphragm. (Full image stack shown in Figure S7). Scale bar: 1 μm. (D) SIM image of 0.125 μm individual Z-slices from a representative renal biopsy (patient MCD7+) in which nephrin is redistributed to a more granular pattern. The left image shows co-localization (yellow) of IgG with the slit diaphragm protein nephrin (red), in contrast to mutual exclusivity with the foot process associated synaptopodin shown in the right image, indicating a continued close spatial association of the IgG with the redistributed nephrin. (Full image stack shown in supplemental Figure S7). Scale bar: 1
Figure 3B:
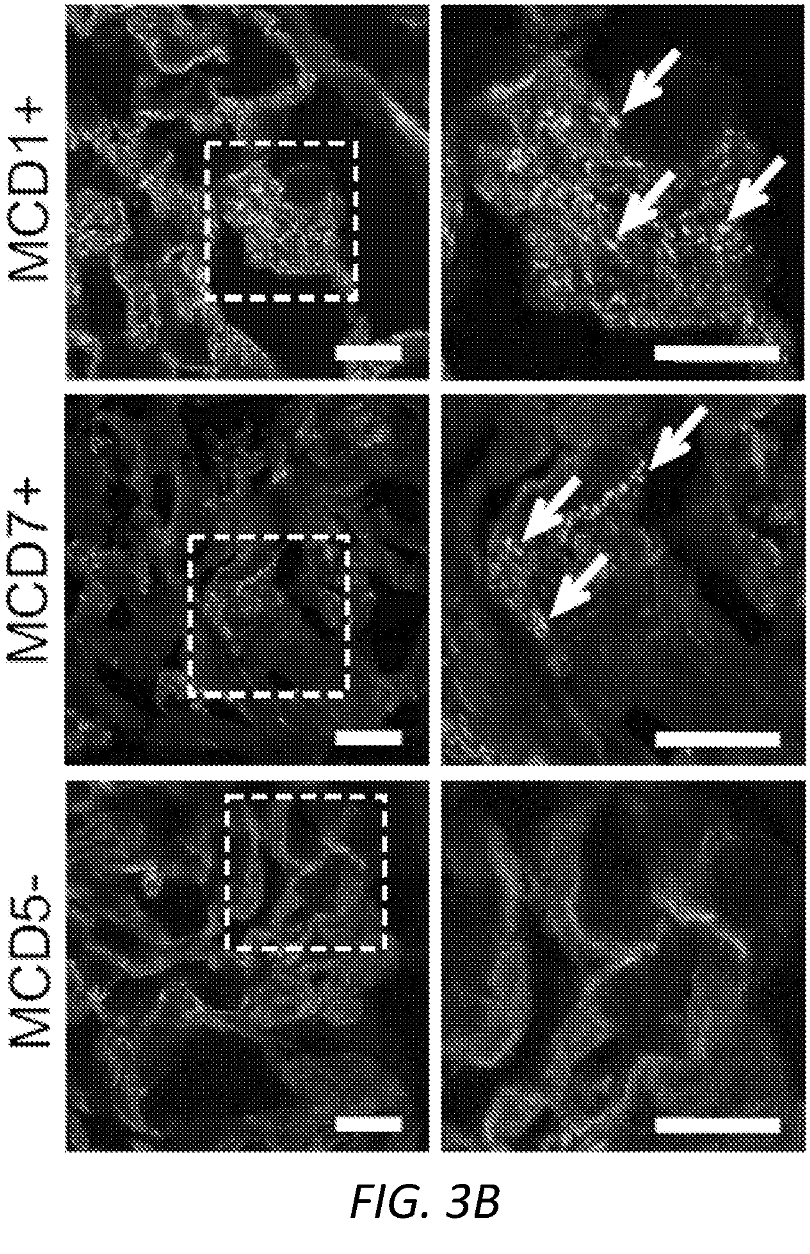
Figure 3C:
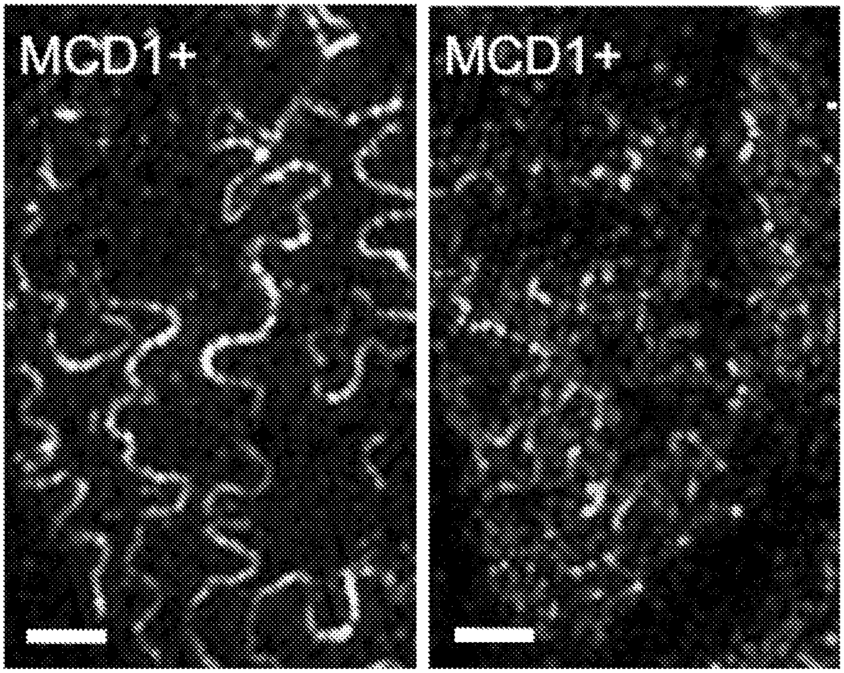
Figure 3D:
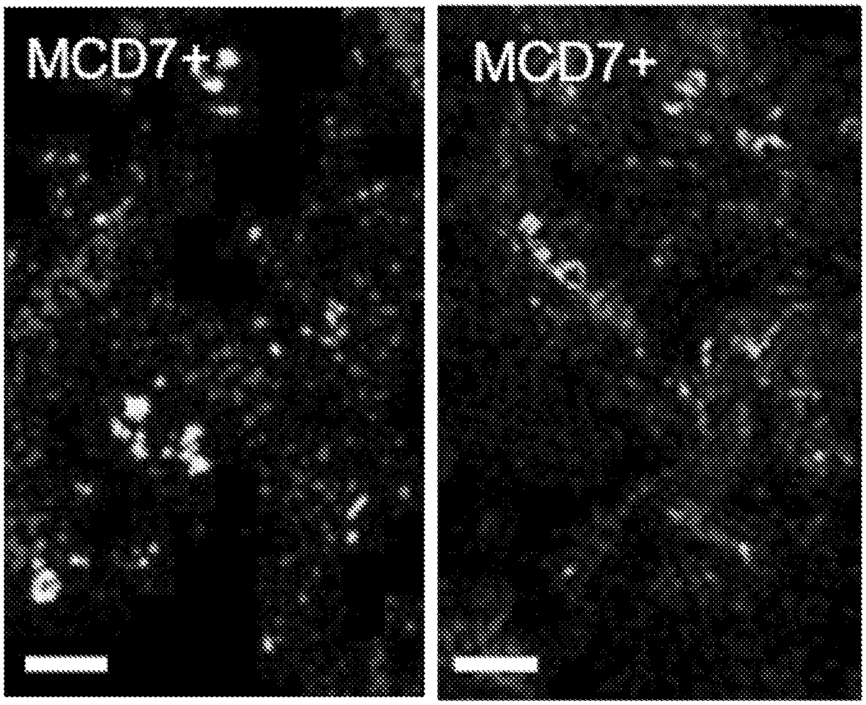
Figure 7B:
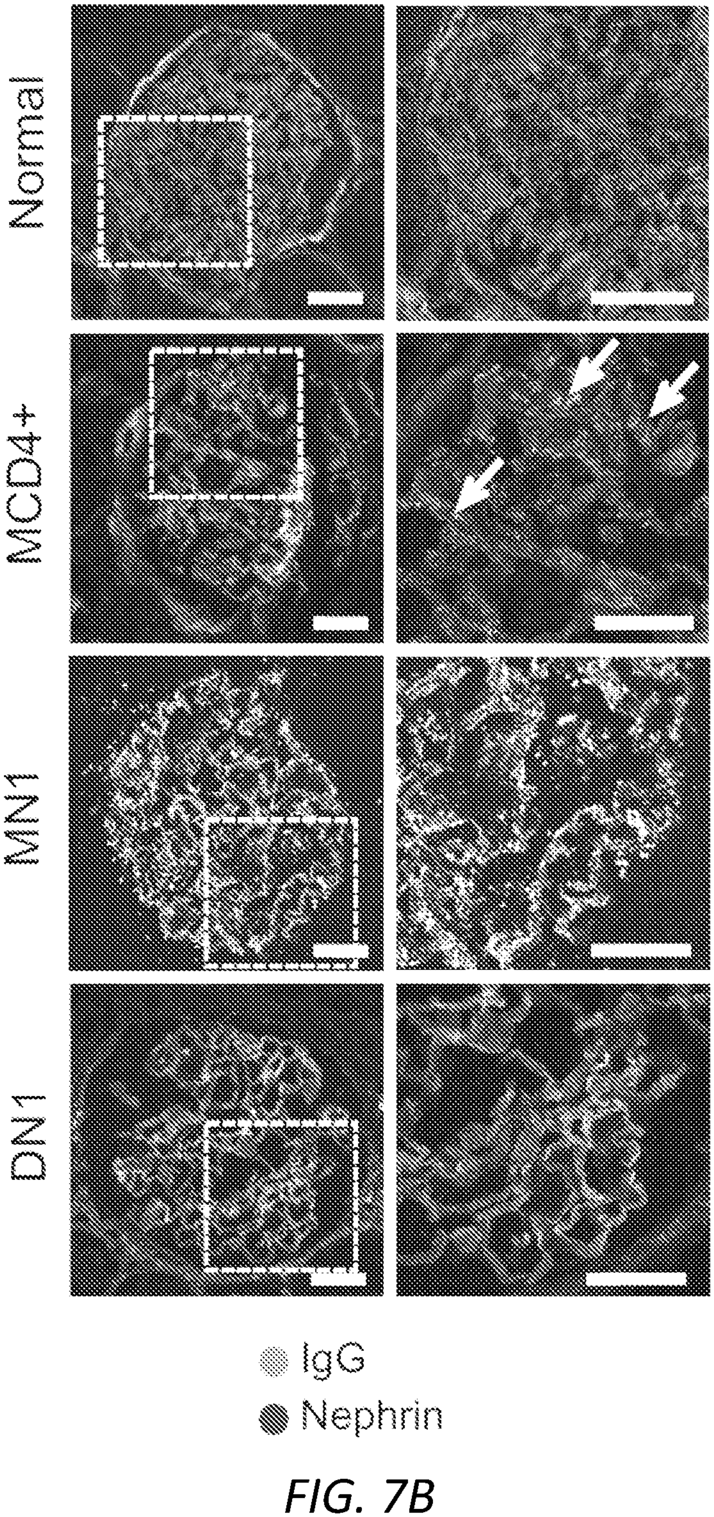
Figure 7C:
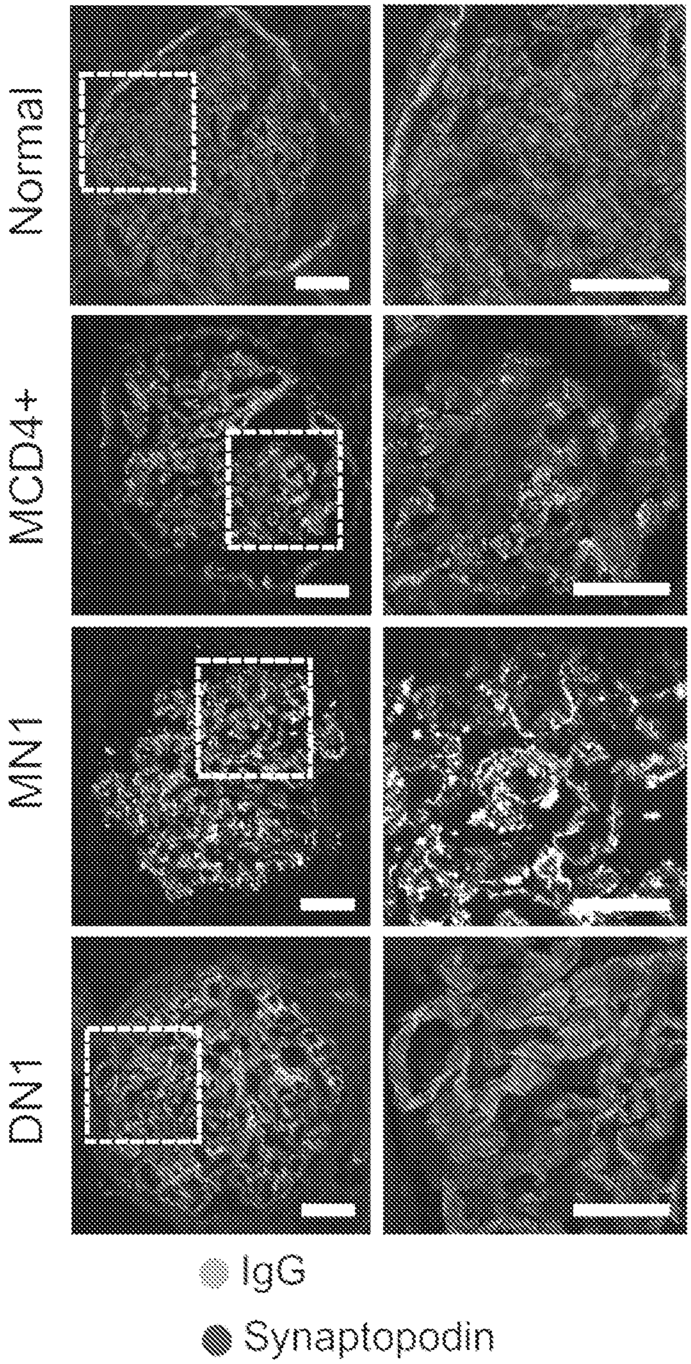

We utilized confocal microscopy to further evaluate this punctate IgG in renal biopsies that were received and processed by us over the last 3 years. We observed two predominant patterns of IgG distribution: GBM-associated fine punctate or curvilinear structures and more apically located punctate and vaguely vesicular clusters, with the latter being more common. These disparate staining patterns may reflect different stages of antibody binding and/or redistribution. In all the MCD+ biopsies evaluated, we observed specific co-localization of nephrin with the punctate IgG and not the background (FIG. 3A, FIG. 7B) which was further corroborated in the control biopsies lacking this punctate IgG (FIG. 3A, FIG. 7B). Antigen specificity was evidenced by a clear spatial association of the IgG with the SD-associated nephrin but not with the podocyte foot process associated synaptopodin by confocal microscopy (FIGS. 3A-B, FIG. 7C) and by Super-Resolution Structured Illumination Microscopy (SR-SIM) which achieves an even higher spatial resolution[24] (FIG. 3C,D). Furthermore, in those biopsies exhibiting the granular redistribution of nephrin away from the SD, as previously described in MCD[20,21], the IgG did not co-localize with the three intracellular podocyte specific proteins; synaptopodin (foot process associated), podocin (SD associated) and WT1 (nuclear).

Figure 4A:
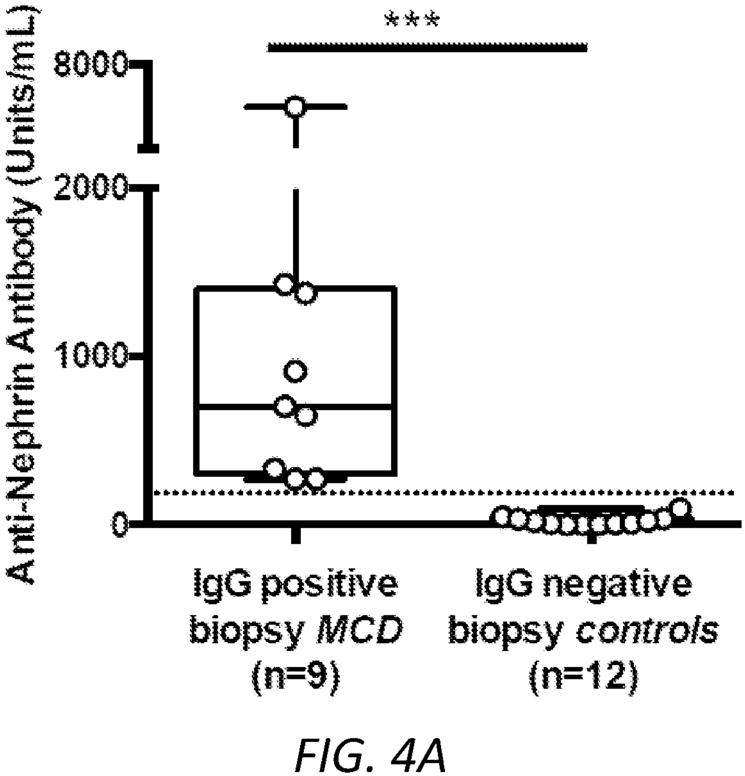
FIGS. 4A-B. Serological testing for anti-nephrin antibodies in patients with biopsy proven MCD. (A) All of the patients with MCD and IgG deposition on biopsy (n=9) were anti-nephrin antibody positive, whereas all of the control subjects lacking IgG deposition on biopsy, consisting of DN (n=2), Amyloidosis (n=1), IgG-negative FSGS (n=2), IgG-negative TL (n=1), normal (n=1), disease-free region of tumor nephrectomy (n=2) and IgG-negative MCD (n=3), were anti-nephrin antibody negative (n=12). The Mann-Whitney U test was used to compare differences between the groups *p<0.001. (B) Serum/plasma samples were obtained from patients with biopsy proven IgG-positive MCD (MCD+) during active disease (within 7 days of presentation with NS) and follow-up samples were obtained during complete (MCD4+, MCD7+) or partial (MCD8+) remission on the day of sample collection. For MCD3+, the follow-up serum sample was obtained approximately 3 weeks after entering a period of sustained complete remission. The threshold for a positive anti-nephrin antibody titer of 187 U/ml (indicated by dotted line) was based on the upper limit of a healthy control population. Anti-nephrin antibodies in serum/plasma were undetectable or significantly reduced to below the threshold for positivity, (red bar) during clinical remission compared with those during active disease (blue bar). Complete remission was defined as urinary protein creatinine ratio (UPCR)<0.3 g/g or urinary albumin creatinine ratio (UACR)<0.2 g/g. Partial remission was defined as a >50% reduction in proteinuria (UPCR) that did not fall below 0.3 g/g. Student t-test was used to compare differences between the active and remission samples. p<0.01, ***p<0.001.
Figure 4B:
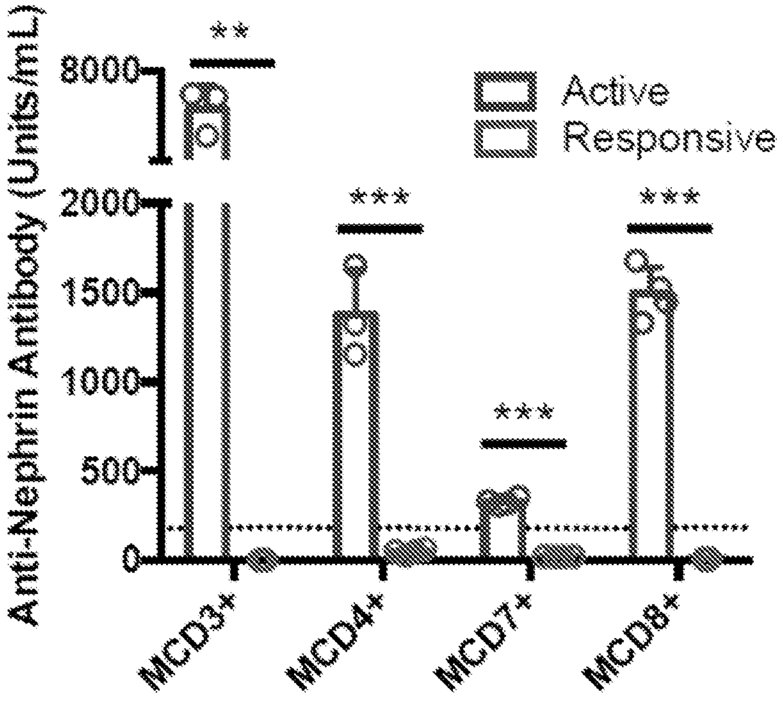
Figure 8A:
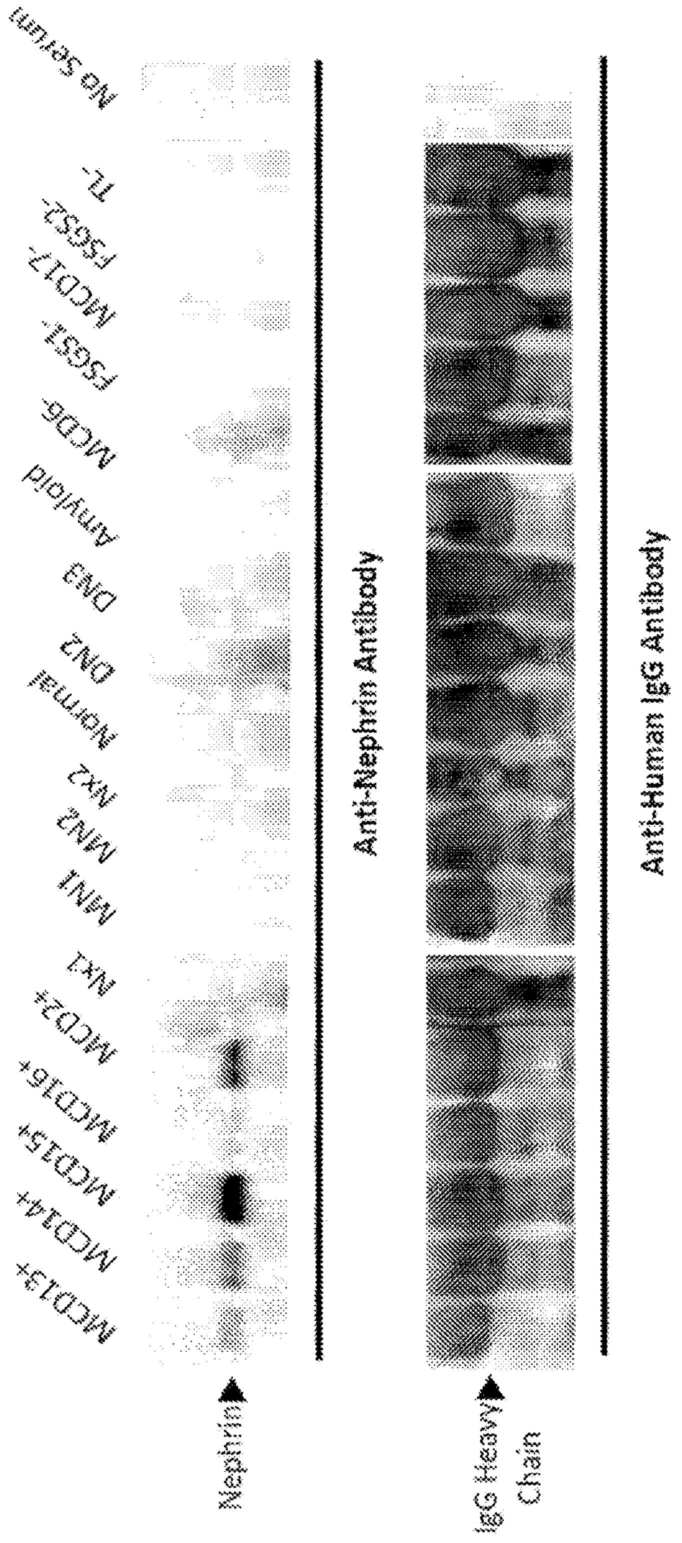
FIGS. 8A-C. Biopsy IgG+ MCD patient serum or plasma immunoprecipitates both nephrin from human glomerular extract (HGE) and affinity-purified recombinant extracellular domain of human nephrin. (A) Nephrin was immunoprecipitated from human glomerular extract (HGE), derived from healthy donor kidney, with serum from patients with biopdy IgG positive MCD (+) and not from control patients lacking IgG on renal biopsy. (B) Purified recombinant extracellular domain of human nephrin (hNephrinG1059) was immunoprecipitated by serum or plasma from patients with MCD and punctate IgG in their renal biopsies (MCD2+, 13+, 14+, 15+, 16+), but not by a control patient without IgG deposition in the biopsy (N×1, disease-free area of tumor nephrectomy). The input lane shows the starting amount of recombinant hNephrinG1059 protein used for the immunoprecipitation (not incubated with serum or Protein G beads). (C) Nephrin was precipitated from HGE in four MCD+ patients during active disease, but not following remission. Immunoprecipitates were electrophoresed under reducing conditions and subjected to Western blot analysis with a primary sheep anti-human nephrin antibody and secondary HRP-conjugated donkey anti-sheep IgG antibody (top) or a primary HRP-conjugated donkey anti-human IgG alone (bottom).
Figure 8B:
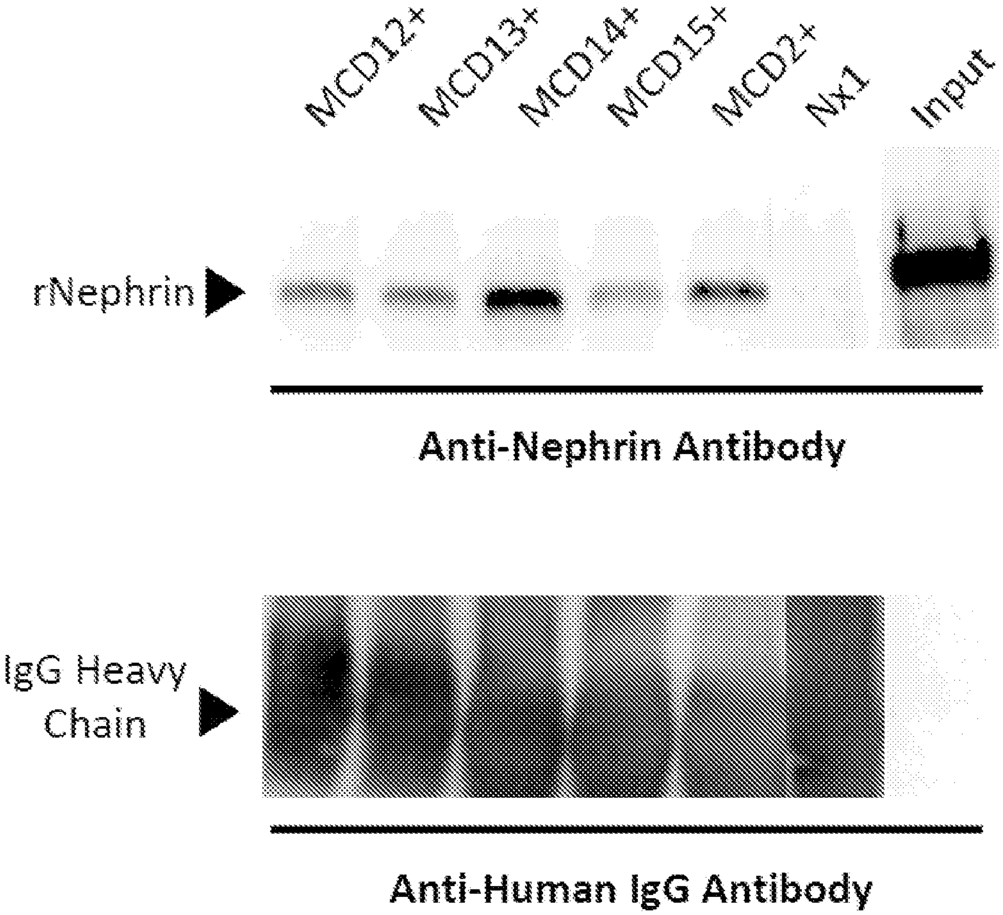
Figure 8C:
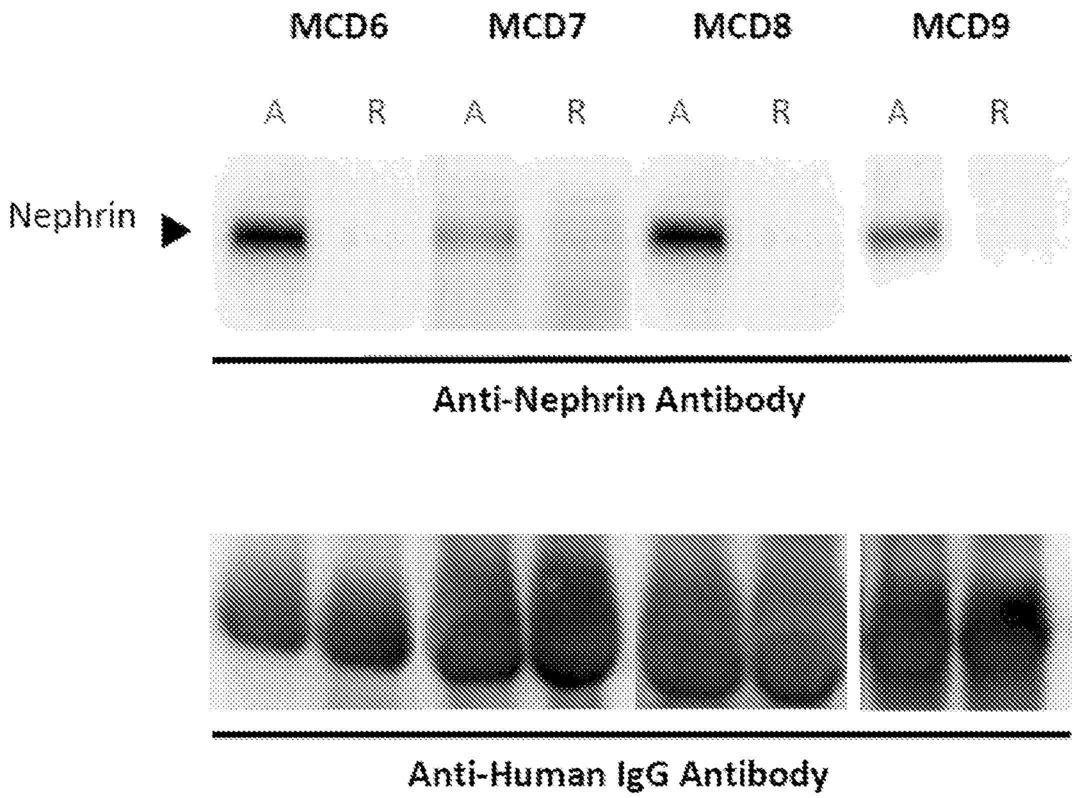

To confirm that MCD+ patients with punctate IgG on renal biopsy do indeed have circulating autoantibodies against nephrin, we evaluated serum or plasma that was available specifically during active disease for 9 of them. As expected, all 9 patients were serologically positive for anti-nephrin antibodies by ELISA, in contrast to 12 control patients lacking punctate IgG on renal biopsy, who were all serologically negative (FIG. 4A, Table 3). A follow-up serum or plasma sample was available for 4 of the 9 MCD+ patients, which showed a significant reduction in antibody titer concordant with treatment response (FIG. 4B). These findings were corroborated by IP (FIGS. 8A-C), and none of the patients in this study who were serologically positive for circulating nephrin autoantibodies cross-reacted with $PLA_2R$.

Finally, to highlight a potential role of pre-transplant nephrin autoantibodies in post-transplant disease recurrence, which generally shows morphologic features indistinguishable from MCD, we identified a 27-year-old patient with childhood onset, steroid dependent MCD and no underlying genetic basis (as determined by clinical whole exome sequencing) who progressed to ESKD requiring kidney transplantation (detailed clinical history given above). In keeping with a pathogenic role for anti-nephrin autoantibodies, she developed massive proteinuria early post-transplant, that in contrast to CNF[18,19] was associated with high pre-transplant levels of nephrin autoantibodies (FIGS. 5A-C). Considering a dilution factor of 0.67 of the initial plasmapheresate relative to pre-pheresis patient plasma[37], detection of anti-nephrin autoantibodies above the threshold in the plasmapheresate indicated presence of circulating anti-nephrin antibody in the patient at time of proteinuria recurrence (FIGS. 5A-C). Having reached sustained remission, no circulating nephrin autoantibodies were detectable in this patient a year post-transplant (FIGS. 5A-C).

TABLE 1

Comparison of the clinical and demographic data of patients from the NEPTUNE cohort grouped based on anti-nephrin antibody status.

| | Anti-nephrin Ab Positive | Anti-nephrin Ab Negative | P value |
|---|---|---|---|
| Cases - no. (% of total cases) | 18 (29) | 44 (71) | |
| Age - yr | 20 (5.5-37.5) | 14 (6.25-17.75) | 0.11 |
| Male - no. (%) | 12 (67) | 23 (52) | 0.40 |
| Female - no. (%) | 6 (33) | 21 (48) | 0.40 |
| Disease onset | | | |
| Adulthood - no. (%) | 9 (50) | 12 (27) | 0.14 |
| Childhood (<18 years) - no. (%) | 9 (50) | 32 (73) | 0.14 |
| Race | | | |
| White - no. (%) | 8 (44) | 24 (55) | 0.58 |
| Black - no. (%) | 4 (22) | 12 (27) | 0.76 |
| Asian - no. (%) | 5 (28) | 2 (4.5) | 0.02* |
| Multi - no. (%) | 1 (6) | 4 (9) | 1.00 |
| Unknown - no. (%) | 0 (0) | 2 (4.5) | 1.00 |
| Hispanic/Latino - no. (%) | 5 (28) | 9 (20) | 0.51 |
| No remission - no. (%) | 0 (0) | 2 (4.5) | 1.00 |
| Partial remission - no. (%) | 3 (17) | 2 (4.5) | 0.14 |
| Complete remission (CR) - no. (%) | 15 (83) | 40 (91) | 0.40 |
| Relapse after CR - no. (% of CR) | 9 (60) | 25 (63) | 1.00 |
| UPCR (g/g) at α-nephrin Ab assay | 9.1 (5.4-13.79) | 7.6 (5.20-10.48) | 0.34 |
| Peak Serum creatinine (mg/dL) | 0.89 (0.58-1.6) | 0.7 (0.52-1.02) | 0.17 |

The threshold for a positive anti-nephrin antibody (α-nephrin Ab) level was based on a randomly selected, healthy control population with no renal disease. Complete remission was defined as a UPCR<0.3 g/g. Partial remission was defined as a >50% reduction in proteinuria that did not fall below 0.3 g/g. The continuous variables are presented as median (interquartile range). Statistical analysis was performed using the Mann-Whitney test for continuous variables and Fisher's exact test for categorical variables (*p<0.05).

TABLE 2

Clinical information for the NEPTUNE patients and controls evaluated for nephrin autoantibodies.

| Pt. | Age | Sex | Race/ Ethnicity | UPCR (g/g) | Peak sCr (mg/dL) | α-Nephrin Ab (U/ml) | Follow up (months) | Remission | Relapse | Treatment |
|---|---|---|---|---|---|---|---|---|---|---|
| N1 | 4 | Male | White* | 25.70 | 0.5 | 2864 ± 832 | 53 | PRTL | N/A | P/CNI/RIT/MMF |
| N2 | 54 | Male | Black | 7.04 | 4.53 | 1271 ± 101 | 23 | CMPLT | Yes | P/CNI/MMF |
| N3 | 17 | Male | White | 8.68 | 0.9 | 963 ± 72 | 10 | CMPLT | No | P/CNI/RIT |
| N4 | 14 | Female | White | 12.06 | 5.45 | 745 ± 99 | 43 | CMPLT | No | P/MMF |
| N5 | 39 | Male | Asian | 19.00 | 1.29 | 736 ± 26 | 29 | CMPLT | Yes | P |
| N6 | 36 | Male | Asian | 27.49 | 1.24 | 512 ± 48 | 38 | CMPLT | Yes | P |
| N7 | 24 | Female | Black | 5.78 | 1.25 | 442 ± 62 | 31 | CMPLT | No | P/MMF |
| N8 | 51 | Female | White* | 19.93 | 2.52 | 423 ± 53 | 1 | CMPLT | No | P |
| N9 | 3 | Male | Black | 10.58 | 0.41 | 392 ± 62 | 28 | CMPLT | Yes | P/CNI |
| N10 | 22 | Male | White* | 3.43 | 0.88 | 381 ± 38 | 18 | CMPLT | No | P |
| N11 | 59 | Female | White* | 11.22 | 2.6 | 320 ± 67 | 31 | CMPLT | Yes | P/RIT |
| N12 | 2 | Male | Asian | 4.28 | 0.83 | 305 ± 115 | 56 | PRTL | N/A | P/CNI/MMF |
| N13 | 6 | Male | Asian | 9.60[#] | 0.34 | 293 ± 57 | 14 | CMPLT | Yes | P/CNI/RIT |
| N14 | 37 | Female | White | 7.77 | 0.8 | 273 ± 135 | 6 | CMPLT | Yes | P/MMF |
| N15 | 18 | Male | Asian | 9.57 | 0.84 | 253 ± 62 | 60 | CMPLT | Yes | P/CNI |
| N16 | 4 | Male | Multi | 3.49 | 0.3 | 235 ± 19 | 12 | PRTL | N/A | P/CNI/MMF |
| N17 | 16 | Male | Black | 7.85 | 0.93 | 193 ± 22 | 38 | CMPLT | Yes | P/MMF |
| N18 | 30 | Female | White* | 3.54 | 0.6 | 191 ± 71 | 19 | CMPLT | No | P/MMF |
| N19 | 7 | Male | White | 4.80 | 0.64 | 172 ± 18 | 33 | CMPLT | No | P/CNI/MMF |
| N20 | 48 | Female | White | 8.42 | 0.91 | 172 ± 32 | 3 | CMPLT | Yes | P/MMF |
| N21 | 17 | Male | Black | 8.41 | 0.7 | 165 ± 35 | 80 | CMPLT | Yes | P/CNI |
| N22 | 24 | Male | Black | 6.17 | 3.16 | 156 ± 30 | 21 | CMPLT | No | P/CNI |
| N23 | 12 | Female | Black | 10.38 | 10 | 137 ± 15 | 57 | CMPLT | Yes | P/CNI/MMF |
| N24 | 15 | Female | Black | 6.66 | 1.02 | 134 ± 69 | 18 | CMPLT | Yes | P |
| N25 | 55 | Male | White | 3.28 | 1.10 | 129 ± 76 | 55 | CMPLT | No | CTX/RIT/FLU |

TABLE 2-continued

Clinical information for the NEPTUNE patients and controls evaluated for nephrin autoantibodies.

| | | | | | | | | | | |
|---|---|---|---|---|---|---|---|---|---|---|
| N26 | 3 | Female | Multi | 4.71 | 0.52 | 129 ± 48 | 53 | CMPLT | Yes | P/CNI |
| N27 | 15 | Male | White | 7.34 | 0.86 | 117 ± 18 | 30 | CMPLT | Yes | P/CNI/RIT |
| N28 | 4 | Female | White | 7.58 | 0.51 | 116 ± 36 | 60 | CMPLT | No | P/CTX/CNI |
| N29 | 29 | Male | White | 13.84 | 0.7 | 98 ± 80 | 47 | CMPLT | No | P |
| N30 | 4 | Male | Black | 16.24 | 0.40 | 86 ± 40 | 48 | CMPLT | Yes | P/CNI |
| N31 | 15 | Male | Asian | 10.03 | 0.88 | 85 ± 45 | 25 | CMPLT | Yes | P/CNI |
| N32 | 36 | Female | White* | 3.00 | 0.71 | 82 ± 18 | 20 | CMPLT | No | P |
| N33 | 1 | Male | White* | 20.93 | 0.32 | 80 ± 11 | 20 | CMPLT | Yes | P/CNI/RIT |
| N34 | 18 | Male | White | 5.25 | 0.8 | 78 ± 12 | 30 | CMPLT | Yes | P/MMF/RIT |
| N35 | 17 | Female | Black | 5.18 | 0.7 | 74 ± 54 | 13 | CMPLT | No | P/CNI |
| N36 | 6 | Female | Unknown * | 10.51 | 0.5 | 72 ± 85 | 54 | CMPLT | Yes | P/CTX |
| N37 | 1 | Female | Black | 40.38 | 0.33 | 71 ± 110 | 28 | CMPLT | No | P/CNI |
| N38 | 13 | Female | Black | 4.71 | 1.1 | 70 ± 12 | 57 | CMPLT | No | P/MMF |
| N39 | 11 | Male | Multi | 5.54 | 1.82 | 59 ± 40 | 53 | CMPLT | Yes | P/CNI |
| N40 | 17 | Male | White | 7.66 | 0.91 | 55 ± 5 | 25 | CMPLT | No | P |
| N41 | 15 | Female | White | 12.53 | 0.57 | 52 ± 51 | 23 | CMPLT | No | P |
| N42 | 57 | Female | Black | 3.46 | 1.77 | 38 ± 30 | 13 | CMPLT | Yes | P/CNI |
| N43 | 16 | Male | White* | 3.52 | 0.59 | 35 ± 12 | 46 | CMPLT | No | P/CNI/MMF |
| N44 | 9 | Female | Asian | 5.18 | 0.47 | 33 ± 13 | 37 | PRTL | N/A | P/CNI/MMF |
| N45 | 16 | Female | Unknown * | 3.07 | 1.2 | 31 ± 31 | 47 | CMPLT | No | P |
| N46 | 14 | Male | White | 3.01 | 0.9 | 29 ± 58 | 60 | CMPLT | Yes | P |
| N47 | 39 | Male | White* | 6.94 | 3.62 | 25 ± 30 | 55 | CMPLT | No | P |

Healthy Controls

| Patient | Age | Sex | Race | α-Nephrin Ab (U/ml) |
|---|---|---|---|---|
| CNT1 | 69 | Male | White | 187 ± 45 |
| CNT2 | 32 | Female | White | 174 ± 84 |
| CNT3 | 23 | Male | White | 100 ± 60 |
| CNT4 | 65 | Female | White | 57 ± 35 |
| CNT5 | 56 | Female | White | 49 ± 11 |
| CNT6 | 17 | Male | White | 43 ± 21 |
| CNT7 | 67 | Male | White | 41 ± 28 |
| CNT8 | 52 | Male | White | 41 ± 34 |
| CNT9 | 33 | Male | White | 39 ± 28 |
| CNT10 | 62 | Female | White | 36 ± 52 |
| CNT11 | 44 | Female | White | 33 ± 35 |
| CNT12 | 82 | Female | White | 27 ± 26 |
| CNT13 | 81 | Male | White | 23 ± 34 |
| CNT14 | 60 | Male | White | 19 ± 14 |
| CNT15 | 40 | Male | White | 18 ± 19 |
| CNT16 | 58 | Male | White | 16 ± 13 |
| CNT17 | 20 | Male | White | 12 ± 15 |
| CNT18 | 22 | Male | White | 12 ± 11 |
| CNT19 | 21 | Male | White | 8 ± 8 |
| CNT20 | 61 | Female | White | 6 ± 8 |
| CNT21 | 48 | Male | White | 6 ± 8 |
| CNT22 | 11 | Female | White | 6 ± 11 |
| CNT23 | 45 | Male | White | 4 ± 9 |
| CNT24 | 56 | Female | White | 3 ± 7 |
| CNT25 | 41 | Male | White | 0 ± 0 |
| CNT26 | 64 | Male | White | 0 ± 0 |
| CNT27 | 49 | Male | White | 0 ± 0 |
| CNT28 | 8 | Male | White | 0 ± 0 |
| CNT29 | 30 | Male | White | 0 ± 0 |
| CNT30 | 22 | Male | White | 0 ± 0 |

$hPLA_2R$+ cohort

| Patient | Age | Gender | α-Nephrin Ab (U/ml) |
|---|---|---|---|
| $PLA_2R1$ | 75 | Female | 196 ± 89 |
| $PLA_2R2$ | 70 | Female | 184 ± 119 |
| $PLA_2R3$ | 72 | Male | 162 ± 141 |
| $PLA_2R4$ | 63 | Female | 160 ± 71 |
| $PLA_2R5$ | 75 | Female | 132 ± 101 |
| $PLA_2R6$ | 70 | Female | 128 ± 83 |
| $PLA_2R7$ | 70 | Male | 101 ± 80 |
| $PLA_2R8$ | 76 | Male | 80 ± 22 |
| $PLA_2R9$ | 37 | Male | 61 ± 13 |
| $PLA_2R10$ | 70 | Male | 53 ± 61 |
| $PLA_2R11$ | 85 | Male | 52 ± 28 |
| $PLA_2R12$ | 37 | Male | 45 ± 16 |

TABLE 2-continued

Clinical information for the NEPTUNE patients and controls evaluated for nephrin autoantibodies.

| | | | |
|---|---|---|---|
| $PLA_2R13$ | 71 | Male | 42 ± 14 |
| $PLA_2R14$ | 77 | Female | 37 ± 57 |
| $PLA_2R15$ | 59 | Male | 36 ± 30 |
| $PLA_2R16$ | 55 | Female | 30 ± 45 |
| $PLA_2R17$ | 33 | Male | 27 ± 13 |
| $PLA_2R18$ | 55 | Male | 25 ± 44 |
| $PLA_2R19$ | 49 | Male | 21 ± 8 |
| $PLA_2R20$ | 60 | Male | 20 ± 17 |
| $PLA_2R21$ | 58 | Male | 20 ± 30 |
| $PLA_2R22$ | 52 | Male | 17 ± 14 |
| $PLA_2R23$ | 38 | Female | 10 ± 7 |
| $PLA_2R24$ | 40 | Female | 10 ± 17 |
| $PLA_2R25$ | 37 | Male | 10 ± 9 |
| $PLA_2R26$ | 59 | Male | 10 ± 17 |
| $PLA_2R27$ | 72 | Male | 9 ± 16 |
| $PLA_2R28$ | 45 | Female | 6 ± 8 |
| $PLA_2R29$ | 70 | Male | 5 ± 9 |
| $PLA_2R30$ | 57 | Female | 5 ± 8 |
| $PLA_2R31$ | 44 | Male | 4 ± 7 |
| $PLA_2R32$ | 58 | Male | 3 ± 6 |
| $PLA_2R33$ | 60 | Male | 2 ± 4 |
| $PLA_2R34$ | 86 | Female | 2 ± 4 |
| $PLA_2R35$ | 77 | Male | 2 ± 3 |
| $PLA_2R36$ | 69 | Male | 1 ± 2 |
| $PLA_2R37$ | 64 | Male | 0 ± 0 |
| $PLA_2R38$ | 64 | Male | 0 ± 0 |
| $PLA_2R39$ | 56 | Female | 0 ± 0 |
| $PLA_2R40$ | 41 | Female | 0 ± 0 |
| $PLA_2R41$ | 61 | Female | 0 ± 0 |
| $PLA_2R42$ | 61 | Female | 0 ± 0 |
| $PLA_2R43$ | 61 | Male | 0 ± 0 |
| $PLA_2R44$ | 56 | Female | 0 ± 0 |
| $PLA_2R45$ | 45 | Male | 0 ± 0 |
| $PLA_2R46$ | 75 | Male | 0 ± 0 |
| $PLA_2R47$ | 84 | Female | 0 ± 0 |

Table 2 provides relevant clinical information for the patients or controls. All patients in the NEPTUNE cohort had biopsy proven minimal change disease (MCD); however, the renal biopsy IgG deposition status was not reported and neither immunofluorescence images nor biopsy material were available for further assessment. Proteinuria values (Urine Protein Creatinine ratio (UPCR)) are from the same day (or within one day) that the serum sample was collected for anti-nephrin antibody (α-Nephrin Ab) testing during active disease. #For patient N13, the UPCR was calculated to be 323 g/g on the day of serum collection and so the value for the next available UPCR (assessed 20 days later) is given. Peak sCr (serum creatinine) was the highest serum creatinine reached during the follow-up period. Partial remission was defined as >50% reduction in the UPCR and complete remission (CR) as UPCR<0.3 g/g. A patient was deemed to have relapsed with a UPCR>3 g/g after first reaching CR. In those patients not reaching CR, the relapse status is not applicable (N/A). Serum was obtained from a randomly selected healthy control cohort from Partners Healthcare Biobank. The threshold for a positive anti-nephrin antibody titer was based on the maximum value for the healthy cohort of 187 U/ml. Antibody titer is given as the mean±S.D. of replicate samples (n≥3) for each patient. Serum from patients who tested positive for anti-human $PLA_2R$ antibodies ($hPLA_2R+$) by two clinically validated assays, ELISA and IIFT (Euroimmun), were obtained from MGH Immunopathology Laboratory. Designations: P, prednisolone; CNI, calcineurin inhibitor; MMF, mycophenolate mofetil; CTX, cyclophosphamide; RIT, rituximab; FLU, flucytosine; PRTL, partial; CMPLT, complete; * indicates Hispanic or Latino ethnicity.

TABLE 3

BWH/MGH/BMC/Mayo Clinic cohort clinical characteristics.

| Patient | Diagnosis | Age | Sex | Race/ Ethnicity | Proteinuria | Serum Cr (mg/dL) | α-Nephrin Ab (U/ml) | Punctate IgG on biopsy |
|---|---|---|---|---|---|---|---|---|
| MCD1 (+) | MCD | 61 | Female | White | 28 | 2.2 | No serum | Yes (IgG1) |
| MCD2 (+) | MCD | 26 | Male | White * | 22.4 | 1.93 | 705 ± 103 | Yes (IgG1) |
| MCD3 (+) | MCD | 65 | Male | White | 7.32 | 2.81 | 5450 ± 1558 | Yes (IgG4) |
| MCD4 (+) | MCD | 28 | Male | Asian | 20 | 1.95 | 1375 ± 253 | Yes (IgG1) |
| MCD5 (−) | MCD | 71 | Female | White | 4.95 | 0.99 | No serum | No |
| MCD6 (−) | MCD | 52 | Male | White | 2.7 | 4.4 | 10 ± 12 | No |
| MCD7 (+) | MCD | 61 | Female | White | 12.95 | 1.4 | 330 ± 18 | Yes (IgG1) |
| MCD8 (+) | MCD | 61 | Male | White | 10.21 | 2.3 | 1427 ± 145 | Yes (IgG4) |
| MCD9 (+) | MCD | 42 | Female | Black | 18 | 2.45 | No serum | Yes (IgG1) |
| MCD10 (+) | MCD | 47 | Male | White | 8.33 | 1.2 | No serum | Yes (ND) |

TABLE 3-continued

BWH/MGH/BMC/Mayo Clinic cohort clinical characteristics.

| Patient | Diagnosis | Age | Sex | Race/ Ethnicity | Proteinuria | Serum Cr (mg/dL) | α-Nephrin Ab (U/ml) | Punctate IgG on biopsy |
|---|---|---|---|---|---|---|---|---|
| MCD11 (+) | MCD | 10 | Female | White | 3+ | 0.5 | No serum | Yes (IgG4) |
| MCD12 (+) | MCD | 30 | Male | Unknown | 5.8 | 0.95 | No serum | Yes (Ig4) |
| MCD13 (+) | MCD | 48 | Male | White | 15 | 2.4 | 649 ± 30 | Yes (ND) |
| MCD14 (+) | MCD | 22 | Female | White | 8.71 | 1.3 | 270 ± 50 | Yes (IgG4) |
| MCD15 (+) | MCD | 68 | Male | White | 7.2 | 2.55 | 911 ± 83 | Yes (IgG4) |
| MCD16 (+) | MCD | 81 | Male | White | 2 | 1.3 | 271 ± 39 | Yes (ND) |
| MCD17 (−) | MCD | 35 | Female | White | $2^{\#}$ | 0.95 | 36 ± 11 | No |
| MCD18 (−) | MCD | 81 | Male | White | 2.14 | 3.22 | 21 ± 3 | No |
| FSGS1+ | Primary FSGS | 37 | Female | Black | 4+ | 3.22 | No serum | Yes (ND) |
| FSGS2− | Primary FSGS | 38 | Female | White | 4.19 | 0.51 | 0 ± 0 | No |
| FSGS3− | Primary FSGS | 53 | Male | White | 8 | 3.5 | 8 ± 6 | No |
| TL1+ | Podocytopathy with TL | 31 | Male | White * | 4+ | 1.2 | No serum | Yes (IgG1) |
| TL2− | Podocytopathy with TL | 39 | Male | White | 10 | 1.02 | 94 ± 100 | No |
| Amyloid | Amyloidosis | 44 | Male | White | 12 | 3.01 | 7 ± 7 | No |
| MN1 | $PLA_2R$+ MN | 68 | Male | White | 7.6 | 0.87 | 24 ± 33 | ND |
| MN2 | $PLA_2R$− MN | 40 | Male | White | 0.83 | 0.87 | 16 ± 15 | ND |
| DN1 | Diabetic Nephropathy | 42 | Male | White | 7.41 | 4.6 | 0 ± 0 | No |
| DN2 | Diabetic Nephropathy | 49 | Male | Black | 10 | 2.8 | 0 ± 0 | No |
| DN3 | Diabetic Nephropathy | 67 | Male | Unknown | 3.5 | 0.8 | No serum | No |
| Nx1 | Nephrectomy for RCC | 79 | Male | White | 0.07 | 1.46 | 47 ± 32 | No |
| Nx2 | Nephrectomy for RCC | 61 | Male | White | negative | 1.51 | 19 ± 33 | No |
| Normal | Normal | 24 | Female | White | 0.2 | 0.74 | 32 ± 37 | No |

The BWH/MGH/BMC/Mayo Clinic cohort consists of patients whose renal biopsy was evaluated for IgG by immunofluorescence staining (IF) and a concurrent serum sample, where available, was evaluated for anti-nephrin antibodies. For the control patients that had a tumor nephrectomy for RCC (N×1, N×2) an area of non-neoplastic renal parenchyma was evaluated by IF. Proteinuria values are given as either UPCR (g/g) or urine dipstick (negative, 3+, 4+) unless otherwise stated (#For patient MCD17−, proteinuria is given as urine albumin creatinine ratio (UACR) (g/g)). Serum Creatinine (Serum Cr) and proteinuria values are those closest to the time of serum sampling for patients evaluated for anti-nephrin antibodies and closest to the biopsy for those who were not. The predominant IgG subclass is given in parenthesis where known (ND indicates that the IgG subclass was not determined due to lack of additional biopsy material). FSGS, focal segmental glomerulosclerosis; TL, tip lesion; MN, membranous nephropathy; RCC, renal cell cancer; MCD, Minimal change disease. * indicates Hispanic or Latino ethnicity.

REFERENCES

1. Vivarelli, M., Massella, L., Ruggiero, B. & Emma, F. Minimal Change Disease. Clin J Am Soc Nephrol 12, 332-345 (2017).
2. Grahammer, F., Schell, C. & Huber, T. B. The podocyte slit diaphragm—from a thin grey line to a complex signalling hub. Nat Rev Nephrol 9, 587-598 (2013).
3. Khoshnoodi, J., et al. Nephrin promotes cell-cell adhesion through homophilic interactions. Am J Pathol 163, 2337-2346 (2003).
4. Kestila, M., et al. Positionally cloned gene for a novel glomerular protein—nephrin—is mutated in congenital nephrotic syndrome. Mol Cell 1, 575-582 (1998).
5. Liu, L., et al. Defective nephrin trafficking caused by missense mutations in the NPHS1 gene: insight into the mechanisms of congenital nephrotic syndrome. Hum Mol Genet 10, 2637-2644 (2001).
6. Elie, V., Fakhoury, M., Deschenes, G. & Jacqz-Aigrain, E. Physiopathology of idiopathic nephrotic syndrome: lessons from glucocorticoids and epigenetic perspectives. Pediatr Nephrol 27, 1249-1256 (2012).
7. Coward, R. J., et al. Nephrotic plasma alters slit diaphragm-dependent signaling and translocates nephrin, Podocin, and CD2 associated protein in cultured human podocytes. J Am Soc Nephrol 16, 629-637 (2005).
8. Ravani, P., Bertelli, E., Gill, S. & Ghiggeri, G. M. Clinical trials in minimal change disease. Nephrol Dial Transplant 32, i7-i13 (2017).
9. Ravani, P., Bonanni, A., Rossi, R., Caridi, G. & Ghiggeri, G. M. Anti-CD20 Antibodies for Idiopathic Nephrotic Syndrome in Children. Clin J Am Soc Nephrol 11, 710-720 (2016).
10. Basu, B., et al. Efficacy of Rituximab vs Tacrolimus in Pediatric Corticosteroid-Dependent Nephrotic Syndrome: A Randomized Clinical Trial. JAMA Pediatr 172, 757-764 (2018).
11. Basu, B. Ofatumumab for rituximab-resistant nephrotic syndrome. N Engl J Med 370, 1268-1270 (2014).
12. Fenoglio, R., et al. Rituximab as a front-line therapy for adult-onset minimal change disease with nephrotic syndrome. Oncotarget 9, 28799-28804 (2018).
13. Madanchi, N., Bitzan, M. & Takano, T. Rituximab in Minimal Change Disease: Mechanisms of Action and Hypotheses for Future Studies. Can J Kidney Health Dis 4, 2054358117698667 (2017).
14. D'Agati, V. D. Minimal Change Disease. in Atlas of Nontumor Pathology. Non-neoplastic Kidney Kidney Diseases., Vol. Fascicle 4 109 (American Registry of Pathology, Washington, DC, 2005).

15. Orikasa, M., Matsui, K., Oite, T. & Shimizu, F. Massive proteinuria induced in rats by a single intravenous injection of a monoclonal antibody. J Immunol 141, 807-814 (1988).
16. Topham, P. S., et al. Nephritogenic mAb 5-1-6 is directed at the extracellular domain of rat nephrin. J Clin Invest 104, 1559-1566 (1999).
17. Takeuchi, K., et al. New Anti-Nephrin Antibody Mediated Podocyte Injury Model Using a C57BL/6 Mouse Strain. Nephron 138, 71-87 (2018).
18. Holmberg, C. & Jalanko, H. Congenital nephrotic syndrome and recurrence of proteinuria after renal transplantation. Pediatr Nephrol 29, 2309-2317 (2014).
19. Kuusniemi, A. M., et al. Plasma exchange and retransplantation in recurrent nephrosis of patients with congenital nephrotic syndrome of the Finnish type (NPHS1). Transplantation 83, 1316-1323 (2007).
20. Doublier, S., et al. Nephrin redistribution on podocytes is a potential mechanism for proteinuria in patients with primary acquired nephrotic syndrome. Am J Pathol 158, 1723-1731 (2001).
21. Wernerson, A., et al. Altered ultrastructural distribution of nephrin in minimal change nephrotic syndrome. Nephrol Dial Transplant 18, 70-76 (2003).
22. Hammers, C. M. & Stanley, J. R. Mechanisms of Disease: Pemphigus and Bullous Pemphigoid. Annu Rev Pathol 11, 175-197 (2016).
23. Gadegbeku, C. A., et al. Design of the Nephrotic Syndrome Study Network (NEPTUNE) to evaluate primary glomerular nephropathy by a multidisciplinary approach. Kidney Int 83, 749-756 (2013).
24. Gustafsson, M. G. Surpassing the lateral resolution limit by a factor of two using structured illumination microscopy. J Microsc 198, 82-87 (2000).
25. Nguyen, V. T., et al. Pemphigus vulgaris IgG and methylprednisolone exhibit reciprocal effects on keratinocytes. J Biol Chem 279, 2135-2146 (2004).
26. Xing, C. Y., et al. Direct effects of dexamethasone on human podocytes. Kidney Int 70, 1038-1045 (2006).
27. Jun, G., Wing, M. K., Abecasis, G. R. & Kang, H. M. An efficient and scalable analysis framework for variant extraction and refinement from population-scale DNA sequence data. Genome Res 25, 918-925 (2015).
28. Gillies, C. E., et al. An eQTL Landscape of Kidney Tissue in Human Nephrotic Syndrome. Am J Hum Genet 103, 232-244 (2018).
29. Sampson, M. G., et al. Using Population Genetics to Interrogate the Monogenic Nephrotic Syndrome Diagnosis in a Case Cohort. J Am Soc Nephrol 27, 1970-1983 (2016).
30. Richards, S., et al. Standards and guidelines for the interpretation of sequence variants: a joint consensus recommendation of the American College of Medical Genetics and Genomics and the Association for Molecular Pathology. Genet Med 17, 405-424 (2015).
31. Beck, L. H., Jr., et al. M-type phospholipase A2 receptor as target antigen in idiopathic membranous nephropathy. N Engl J Med 361, 11-21 (2009).
32. Hiraoka, Y., Sedat, J. W. & Agard, D. A. Determination of three-dimensional imaging properties of a light microscope system. Partial confocal behavior in epifluorescence microscopy. Biophys J 57, 325-333 (1990).
33. Matsuda, A., Schermelleh, L., Hirano, Y., Haraguchi, T. & Hiraoka, Y. Accurate and fiducial-marker-free correction for three-dimensional chromatic shift in biological fluorescence microscopy. Sci Rep 8, 7583 (2018).
34. Waritani, T., Chang, J., McKinney, B. & Terato, K. An ELISA protocol to improve the accuracy and reliability of serological antibody assays. MethodsX 4, 153-165 (2017).
35. Nagahama, K., et al. Possible role of autoantibodies against nephrin in an experimental model of chronic graft-versus-host disease. Clin Exp Immunol. 2005 August; 141(2): 215-222.
36. Chaudhuri, A., et al. Rituximab treatment for recurrence of nephrotic syndrome in a pediatric patient after renal transplantation for congenital nephrotic syndrome of Finnish type. Pediatr Transplant 16, E183-187 (2012).
36. Hansrivijit, P., Cheungpasitporn, W., Thongprayoon, C. & Ghahramani, N. Rituximab therapy for focal segmental glomerulosclerosis and minimal change disease in adults: a systematic review and meta-analysis. BMC Nephrol 21, 134 (2020).
37. Kaplan, A. A. Therapeutic plasma exchange: a technical and operational review. J Clin Apher 28, 3-10 (2013).

| Extracellular fragment of Nephrin $_{G1059}$ |
|---|
| DNA sequence |

(SEQ ID NO: 2)

ATGGCCCTGGGGACGACGCTCAGGGCTTCTCTCCTGCTCCTGGGGCTGCTGACTGAAGGCCTGGC

GCATTGGCGATTCCTGCCTCCGTTCCCCGGGGCTTCTGGGCCCTGCCTGAAAACCTGACGGTGGT

GGAGGGGCCTCAGTGGAGCTGCGTTGTGGGGTCAGCACCCCTGGCAGTGCGGTGCAATGGGCCAA

AGATGGGCTGCTCCTGGGCCCCGACCCCAGGATCCCAGGCTTCCCGAGGTACCGCCTGGAAGGGG

ACCCTGCTAGAGGGAATTCCACCTGCACATCGAGGCCTGTGACCTCAGCGATGACGCGGAGTATG

AGTGCCAGGTCGGCCGCTCTGAGATGGGGCCCGAGCTCGTGTCTCCCAGAGTGATCCTCTCCATC

CTGGTTCCTCCCAAGCTGCTCCTGCTGACCCCAGAGGCAGGCACCATGGTCACCTGGGTAGCTGG

GCAGGAGTACGTGGTCAACTGTGTGTCTGGGGACGCGAAGCCAGCACCTGACATCACCATTCTCC

TGAGTGGACAGACAATATCTGACATCTCTGCAAACGTGAACGAGGGCTCCCAGCAGAAACTCTTC

ACTGTGGAGGCCACAGCCAGGGTGACACCCCGGAGCTCAGATAATAGGCAGTTGCTGGTCTGTGA

GGCGTCTAGCCCAGCACTGGAGGCCCCCATCAAGGCCTCATTCACCGTGAATGTTCTGTTCCCTC

-continued

| Extracellular fragment of Nephrin $_{G1059}$ |
|---|

CAGGACCCCCTGTCATCGAGTGGCCAGGCCTGGATGAGGGGCACGTGCGGGCAGGACAGAGCTTG

GAGCTGCCGTGCGTGGCCCGAGGGGGTAATCCCTTAGCCACACTGCAGTGGCTGAAGAATGGCCA

GCCGGTGTCCACAGCGTGGGGCACAGAGCACACCCAGGCGGTGGCCCGCAGTGTGCTGGTGATGA

CCGTGAGGCCAGAAGACCATGGAGCGCAGCTCAGCTGCGAGGCCCACAACAGCGTGTCTGCAGGG

ACCCAGGAGCACGGCATCACACTGCAGGTCACCTTTCCCCCTAGTGCCATTATTATCTTGGGATC

TGCATCCCAGACTGAGAACAAGAACGTGACACTCTCCTGTGTCAGCAAGTCCAGTCGCCCGCGGG

TTCTGCTACGATGGTGGCTGGGCTGGCGGCAGCTGCTGCCCATGGAGGAGACAGTCATGGATGGA

CTGCATGGCGGTCACATCTCCATGTCCAACCTGACATTCCTGGCGCGGCGGGAGGACAACGGTCT

GACCCTCACATGTGAGGCCTTCAGTGAAGCCTTCACCAAGGAGACCTTCAAGAAGTCGCTCATCC

TGAACGTAAAATATCCCGCCCAGAAACTGTGGATTGAGGGTCCCCCAGAGGGCCAGAAGCTCCGG

GCTGGGACCCGGGTGAGGCTGGTGTGTTTGGCTATCGGGGGCAACCCAGAGCCCTCCCTCATGTG

GTACAAGGACTCGCGCACCGTGACCGAGTCGCGGCTGCCGCAGGAGTCGCGGCGCGTGCATCTCG

GCAGCGTGGAGAAATCTGGGAGCACCTTCTCCCGAGAGCTGGTGCTGGTCACAGGGCCGTCGGAC

AACCAGGCCAAGTTCACGTGCAAGGCTGGACAGCTCAGCGCGTCCACGCAGCTGGCGGTGCAGTT

TCCCCCAACTAACGTGACGATCCTGGCCAACGCATCCGCACTGCGCCCGGGAGACGCCTTAAACT

TGACATGCGTCAGCGTCAGCAGCAATCCGCCGGTCAACTTGTCCTGGGACAAGGAAGGGGAGAGG

CTGGAGGGCGTGGCCGCCCCACCCCGGAGAGCCCCATTCAAAGGCTCCGCCGCCGCCAGGAGCGT

CCTTCTGCAAGTGTCATCCCGCGATCATGGCCAGCGCGTGACCTGCCGCGCCCACAGCGCCGAGC

TCCGCGAAACCGTGAGCTCCTTCTATCGCCTCAACGTACTGTACCGTCCAGAGTTCCTGGGGGAG

CAGGTGCTGGTGGTGACCGCGGTGGAGCAGGGCGAGGCGTTGCTGCCCGTGTCCGTGTCCGCTAA

CCCCGCCCCCGAGGCCTTCAACTGGACCTTCCGCGGCTATCGCCTCAGTCCAGCGGGGGGCCCCC

GGCATCGCATCCTGTCCAGCGGGGCTCTGCATCTGTGGAATGTGACCCGCGCGGACGACGGCCTC

TATCAGCTGCACTGCCAGAACTCTGAGGGCACCGCGGAAGCGCGGCTGCGGCTGGACGTGCACTA

TGCTCCCACCATCCGTGCCCTCCAGGACCCCACTGAGGTGAACGTCGGGGGTTCTGTGGACATAG

TCTGCACTGTCGATGCCAATCCCATCCTCCCGGGCATGTTCAACTGGGAGAGACTGGGAGAAGAT

GAGGAGGACCAGAGCCTGGATGACATGGAGAAGATATCCAGGGGACCAACGGGGCGCCTGCGGAT

TCACCATGCCAAACTGGCCCAGGCTGGCGCTTACCAGTGCATTGTGGACAATGGGGTGGCGCCTC

CAGCACGACGGCTGCTCCGTCTTGTTGTCAGATTTGCCCCCCAGGTGGAGCACCCCACTCCCCTA

ACTAAGGTGGCTGCAGCTGGAGACAGCACCAGTTCTGCCACCCTCCACTGCCGTGCCCGAGGTGT

CCCCAACATCGTTTTCACTTGGACAAAAAACGGGGTCCCTCTGGATCTCCAAGATCCCAGGTACA

CGGAGCACACATACCACCAAGGTGGTGTCCACAGCAGCCTCCTGACCATTGCCAACGTGTCTGCC

GCCCAGGATTACGCCCTCTTCACATGTACAGCCACCAACGCCCTTGGCTCGGACCAAACCAACAT

TCAACTTGTCAGCATCAGCCGCCCTGACCCTCCATCAGGATTAAAGGTTGTGAGTCTGACCCCAC

ACTCCGTGGGGCTGGAGTGGAAGCCTGGCTTTGATGGGGGCCTGCCACAGAGGTTCTGCATCAGG

TATGAGGCCCTGGGGACTCCAGGGTTCCACTATGTGGATGTCGTACCACCCCAGGCCACCACCTT

CACGCTGACTGGTCTACAGCCTTCTACAAGATACAGGGTCTGGCTGCTGGCCAGTAATGCCTTGG

GGGACAGTGGACTGGCTGACAAAGGGACCCAGCTTCCCATCACTACCCCAGGTCTCCACCAGCCT

TCTGGAGAACCTGAAGACCAGCTGCCCACAGAGCCACCTTCAGGACCCTCGGGGGGTCCCACCA

-continued

| Extracellular fragment of Nephrin $_{G1059}$ |
|---|
| CCATCACCACCATTAG |
| Translated protein sequence |
| (The bold sequence is a Glycine-serine-6X histidine that was added to the end of the protein to allow for affinity purification) (SEQ ID NO: 3) |
| MALGTTLRASLLLLGLLTEGLAQLAIPASVPRGFWALPENLTVVEGASVELRCGVSTPGSAVQWA |
| KDGLLLGPDPRIPGFPRYRLEGDPARGEFHLHIEACDLSDDAEYECQVGRSEMGPELVSPRVILS |
| ILVPPKLLLLTPEAGTMVTWVAGQEYVVNCVSGDAKPAPDITILLSGQTISDISANVNEGSQQKL |
| FTVEATARVTPRSSDNRQLLVCEASSPALEAPIKASFTVNVLFPPGPPVIEWPGLDEGHVRAGQS |
| LELPCVARGGNPLATLQWLKNGQPVSTAWGTEHTQAVARSVLVMTVRPEDHGAQLSCEAHNSVSA |
| GTQEHGITLQVTFPPSAIIILGSASQTENKNVTLSCVSKSSRPRVLLRWWLGWRQLLPMEETVMD |
| GLHGGHISMSNLTFLARREDNGLTLTCEAFSEAFTKETFKKSLILNVKYPAQKLWIEGPPEGQKL |
| RAGTRVRLVCLAIGGNPEPSLMWYKDSRTVTESRLPQESRRVHLGSVEKSGSTFSRELVLVTGPS |
| DNQAKFTCKAGQLSASTQLAVQFPPTNVTILANASALRPGDALNLTCVSVSSNPPVNLSWDKEGE |
| RLEGVAAPPRRAPFKGSAAARSVLLQVSSRDHGQRVTCRAHSAELRETVSSFYRLNVLYRPEFLG |
| EQVLVVTAVEQGEALLPVSVSANPAPEAFNWTFRGYRLSPAGGPRHRILSSGALHLWNVTRADDG |
| LYQLHCQNSEGTAEARLRLDVHYAPTIRALQDPTEVNVGGSVDIVCTVDANPILPGMENWERLGE |
| DEEDQSLDDMEKISRGPTGRLRIHHAKLAQAGAYQCIVDNGVAPPARRLLRLVVRFAPQVEHPTP |
| LTKVAAAGDSTSSATLHCRARGVPNIVFTWTKNGVPLDLQDPRYTEHTYHQGGVHSSLLTIANVS |
| AAQDYALFTCTATNALGSDQTNIQLVSISRPDPPSGLKVVSLTPHSVGLEWKPGFDGGLPQRFCI |
| RYEALGTPGFHYVDVVPPQATTFTLTGLQPSTRYRVWLLASNALGDSGLADKGTQLPITTPGLHQ |
| PSGEPEDQLPTEPPSGPSG**GSHHHHHH** |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a human subject who has minimal change disease (MCD) or an acute acquired nephrotic syndrome or focal segmental glomerulosclerosis (FSGS), the method comprising:

providing a sample from a human subject who has, or who is suspected of having, MCD or an acute acquired nephrotic syndrome or FSGS, the sample being selected from renal biopsy tissue, whole blood, serum or plasma;

providing in the sample a human nephrin protein or extracellular domain thereof, the extracellular domain thereof consisting of SEQ ID NO:1, wherein the human nephrin protein or extracellular domain thereof is at least one of recombinantly produced, tagged and labeled;

detecting a level of anti-nephrin antibodies in the sample that are bound to said human nephrin protein or extracellular domain thereof;

comparing the level of anti-nephrin antibodies in the sample to a reference level; and identifying a subject who has a level of anti-nephrin antibodies in the sample above the reference level as having or at risk of developing MCD or an acute acquired nephrotic syndrome or FSGS.

2. The method of claim 1, further comprising administering a treatment for MCD or for an acute acquired nephrotic syndrome or for FSGS to the subject.

3. A method for treating minimal change disease (MCD) or an acute acquired nephrotic syndrome or focal segmental glomerulosclerosis (FSGS) in a subject, the method comprising:

providing a sample from a human subject who has, or who is suspected of having, MCD or an acute acquired nephrotic syndrome or FSGS, the sample being selected from renal biopsy tissue, whole blood, serum or plasma;

detecting a level of anti-nephrin antibodies in the sample;

comparing the level of anti-nephrin antibodies in the sample to a reference level;

identifying a subject who has a level of anti-nephrin antibodies in the sample above the reference level as having or at risk of developing MCD or an acute acquired nephrotic syndrome or FSGS; and administering a treatment for MCD or an acute acquired nephrotic syndrome or FSGS to the subject, comprising administration of one or more of a glucocorticoid, a treatment that reduces levels of anti-nephrin antibodies, or a treatment that targets B cells, to the subject.

4. The method of claim 2, wherein the treatment for MCD or an acute acquired nephrotic syndrome or FSGS comprises administration of one or more of a glucocorticoid, a treatment that reduces levels of anti-nephrin antibodies, or a treatment that targets B cells, to the subject.

5. The method of claim 4, wherein the glucocorticoid is prednisone, beclomethasone, betamethasone, budesonide, cortisone, dexamethasone, hydrocortisone, triamcinolone, prednisolone, or methylprednisolone.

6. The method of claim 4, wherein the treatment that targets B-cells is a targeted therapy that depletes B cells or is an inhibitor of B lymphocyte stimulation.

7. The method of claim 6, wherein the targeted therapy that depletes B cells is an anti-CD20 antibody; an anti-CD19 antibody; or an anti-BAFF antibody.

8. The method of claim 6, wherein the inhibitor of B lymphocyte stimulation is belimumab, tabalumab, or atacicept.

9. The method of claim 4, wherein the treatment that reduces levels of anti-nephrin antibodies is plasmapheresis.

10. The method of claim 4, further comprising:

obtaining a subsequent sample from the subject, the subsequent sample being selected from renal biopsy tissue, whole blood, serum or plasma;

detecting a subsequent level of anti-nephrin antibodies in the subsequent sample;

comparing the subsequent level of anti-nephrin antibodies to a reference level; and (i) if the level of anti-nephrin antibodies in the subsequent sample is above the reference level, then continuing to administer the treatment to the subject or administering a different treatment for MCD or an acute acquired nephrotic syndrome or FSGS to the subject, or (ii) if the level of anti-nephrin antibodies in the subsequent sample is below the reference level, then discontinuing the treatment.

11. A method comprising:

providing a sample from a human subject who has, or who is suspected of having, MCD or an acute acquired nephrotic syndrome or FSGS, the sample being selected from renal biopsy tissue, whole blood, serum or plasma;

providing in the sample a human nephrin protein or extracellular domain thereof, the extracellular domain consisting of SEQ ID NO: 1, wherein the human nephrin protein or extracellular domain thereof is at least one of recombinantly produced, tagged and labeled; and detecting a level of anti-nephrin antibodies in the sample that are bound to said human nephrin protein or extracellular domain thereof.

12. The method of claim 11, further comprising comparing the level of anti-nephrin antibodies in the sample to a reference level; and providing the level and the reference level to a healthcare provider and/or the subject.

13. A method for determining eligibility of a human subject who has end stage renal disease (ESRD) for a kidney transplant, the method comprising:

providing a sample from the subject, the sample being selected from renal biopsy tissue, whole blood, serum or plasma;

contacting the sample with a human nephrin protein or extracellular domain thereof, the extracellular domain consisting of SEQ ID NO:1, wherein the human nephrin protein or extracellular domain thereof is at least one of recombinantly produced, tagged and labeled;

detecting a level of anti-nephrin antibodies in the sample, wherein the anti-nephrin antibodies bind specifically to SEQ ID NO:1;

comparing the level of anti-nephrin antibodies in the sample to a reference level; and identifying a subject who has a level of anti-nephrin antibodies in the sample above the reference level as ineligible for transplant.

14. The method of claim 13, further comprising administering a treatment that comprises administration of one or more of a glucocorticoid, a treatment that reduces levels of anti-nephrin antibodies, or a treatment that targets B cells, to the subject;

obtaining a subsequent sample from the subject, the subsequent sample being selected from renal biopsy tissue, whole blood, serum or plasma;

detecting a subsequent level of anti-nephrin antibodies in the subsequent sample;

comparing the subsequent level of anti-nephrin antibodies to a reference level; and (i) if the level of anti-nephrin antibodies in the subsequent sample is above the reference level, then continuing to administer the treatment to the subject or administering a different treatment to the subject, or (ii) if the level of anti-nephrin antibodies in the subsequent sample is below the reference level, then identifying the subject as eligible for transplant.

15. The method of claim 1, wherein said detecting a level of anti-nephrin antibodies in the sample comprises performing Western blot; enzyme linked immunosorbent assay (ELISA); radio-immunoassay (RIA); immunohistochemistry (IHC); immune-precipitation assay; or fluorescent activated cell sorting (FACS).

16. A method comprising:

providing a sample from a human subject who has, or who is suspected of having, MCD or an acute acquired nephrotic syndrome or FSGS, the sample being selected from renal biopsy tissue, whole blood, serum or plasma;

contacting the sample with a human nephrin protein or extracellular domain thereof, the extracellular domain consisting of SEQ ID NO:1, wherein the human nephrin protein or extracellular domain thereof is at least one of recombinantly produced, tagged and labeled; and detecting a level of anti-nephrin antibodies in the sample, wherein the anti-nephrin antibodies bind specifically to SEQ ID NO: 1.

17. The method of claim 16, further comprising administering a treatment that comprises administration of one or more of a glucocorticoid, a treatment that reduces levels of anti-nephrin antibodies, or a treatment that targets B cells, to the subject.

* * * * *

SEQUENCE LISTING

```
<160> NUMBER OF SEQ ID NOS: 3

<210> SEQ ID NO 1
<211> LENGTH: 1059
<212> TYPE: PRT
<213> ORGANISM: Artificial Sequence
<220> FEATURE:
<223> OTHER INFORMATION: extracellular domain of nephrin (aa1-1059)

<400> SEQUENCE: 1

Met Ala Leu Gly Thr Thr Leu Arg Ala Ser Leu Leu Leu Leu Gly Leu
1               5                   10                  15

Leu Thr Glu Gly Leu Ala Gln Leu Ala Ile Pro Ala Ser Val Pro Arg
            20                  25                  30

Gly Phe Trp Ala Leu Pro Glu Asn Leu Thr Val Val Glu Gly Ala Ser
        35                  40                  45
```

```
Val Glu Leu Arg Cys Gly Val Ser Thr Pro Gly Ser Ala Val Gln Trp
    50                  55                  60

Ala Lys Asp Gly Leu Leu Leu Gly Pro Asp Pro Arg Ile Pro Gly Phe
65                  70                  75                  80

Pro Arg Tyr Arg Leu Glu Gly Asp Pro Ala Arg Gly Glu Phe His Leu
                85                  90                  95

His Ile Glu Ala Cys Asp Leu Ser Asp Asp Ala Glu Tyr Glu Cys Gln
            100                 105                 110

Val Gly Arg Ser Glu Met Gly Pro Glu Leu Val Ser Pro Arg Val Ile
        115                 120                 125

Leu Ser Ile Leu Val Pro Pro Lys Leu Leu Leu Leu Thr Pro Glu Ala
    130                 135                 140

Gly Thr Met Val Thr Trp Val Ala Gly Gln Glu Tyr Val Val Asn Cys
145                 150                 155                 160

Val Ser Gly Asp Ala Lys Pro Ala Pro Asp Ile Thr Ile Leu Leu Ser
                165                 170                 175

Gly Gln Thr Ile Ser Asp Ile Ser Ala Asn Val Asn Glu Gly Ser Gln
            180                 185                 190

Gln Lys Leu Phe Thr Val Glu Ala Thr Ala Arg Val Thr Pro Arg Ser
        195                 200                 205

Ser Asp Asn Arg Gln Leu Leu Val Cys Glu Ala Ser Ser Pro Ala Leu
    210                 215                 220

Glu Ala Pro Ile Lys Ala Ser Phe Thr Val Asn Val Leu Phe Pro Pro
225                 230                 235                 240

Gly Pro Pro Val Ile Glu Trp Pro Gly Leu Asp Glu Gly His Val Arg
                245                 250                 255

Ala Gly Gln Ser Leu Glu Leu Pro Cys Val Ala Arg Gly Gly Asn Pro
            260                 265                 270

Leu Ala Thr Leu Gln Trp Leu Lys Asn Gly Gln Pro Val Ser Thr Ala
        275                 280                 285

Trp Gly Thr Glu His Thr Gln Ala Val Ala Arg Ser Val Leu Val Met
    290                 295                 300

Thr Val Arg Pro Glu Asp His Gly Ala Gln Leu Ser Cys Glu Ala His
305                 310                 315                 320

Asn Ser Val Ser Ala Gly Thr Gln Glu His Gly Ile Thr Leu Gln Val
                325                 330                 335

Thr Phe Pro Pro Ser Ala Ile Ile Ile Leu Gly Ser Ala Ser Gln Thr
            340                 345                 350

Glu Asn Lys Asn Val Thr Leu Ser Cys Val Ser Lys Ser Ser Arg Pro
        355                 360                 365

Arg Val Leu Leu Arg Trp Trp Leu Gly Trp Arg Gln Leu Leu Pro Met
    370                 375                 380

Glu Glu Thr Val Met Asp Gly Leu His Gly Gly His Ile Ser Met Ser
385                 390                 395                 400

Asn Leu Thr Phe Leu Ala Arg Arg Glu Asp Asn Gly Leu Thr Leu Thr
                405                 410                 415

Cys Glu Ala Phe Ser Glu Ala Phe Thr Lys Glu Thr Phe Lys Lys Ser
            420                 425                 430

Leu Ile Leu Asn Val Lys Tyr Pro Ala Gln Lys Leu Trp Ile Glu Gly
        435                 440                 445

Pro Pro Glu Gly Gln Lys Leu Arg Ala Gly Thr Arg Val Arg Leu Val
    450                 455                 460
```

```
Cys Leu Ala Ile Gly Gly Asn Pro Glu Pro Ser Leu Met Trp Tyr Lys
465                 470                 475                 480

Asp Ser Arg Thr Val Thr Glu Ser Arg Leu Pro Gln Glu Ser Arg Arg
                485                 490                 495

Val His Leu Gly Ser Val Glu Lys Ser Gly Ser Thr Phe Ser Arg Glu
            500                 505                 510

Leu Val Leu Val Thr Gly Pro Ser Asp Asn Gln Ala Lys Phe Thr Cys
        515                 520                 525

Lys Ala Gly Gln Leu Ser Ala Ser Thr Gln Leu Ala Val Gln Phe Pro
    530                 535                 540

Pro Thr Asn Val Thr Ile Leu Ala Asn Ala Ser Ala Leu Arg Pro Gly
545                 550                 555                 560

Asp Ala Leu Asn Leu Thr Cys Val Ser Val Ser Ser Asn Pro Pro Val
                565                 570                 575

Asn Leu Ser Trp Asp Lys Glu Gly Glu Arg Leu Glu Gly Val Ala Ala
            580                 585                 590

Pro Pro Arg Arg Ala Pro Phe Lys Gly Ser Ala Ala Ala Arg Ser Val
        595                 600                 605

Leu Leu Gln Val Ser Ser Arg Asp His Gly Gln Arg Val Thr Cys Arg
    610                 615                 620

Ala His Ser Ala Glu Leu Arg Glu Thr Val Ser Ser Phe Tyr Arg Leu
625                 630                 635                 640

Asn Val Leu Tyr Arg Pro Glu Phe Leu Gly Glu Gln Val Leu Val Val
                645                 650                 655

Thr Ala Val Glu Gln Gly Glu Ala Leu Leu Pro Val Ser Val Ser Ala
            660                 665                 670

Asn Pro Ala Pro Glu Ala Phe Asn Trp Thr Phe Arg Gly Tyr Arg Leu
        675                 680                 685

Ser Pro Ala Gly Gly Pro Arg His Arg Ile Leu Ser Ser Gly Ala Leu
    690                 695                 700

His Leu Trp Asn Val Thr Arg Ala Asp Asp Gly Leu Tyr Gln Leu His
705                 710                 715                 720

Cys Gln Asn Ser Glu Gly Thr Ala Glu Ala Arg Leu Arg Leu Asp Val
                725                 730                 735

His Tyr Ala Pro Thr Ile Arg Ala Leu Gln Asp Pro Thr Glu Val Asn
            740                 745                 750

Val Gly Gly Ser Val Asp Ile Val Cys Thr Val Asp Ala Asn Pro Ile
        755                 760                 765

Leu Pro Gly Met Phe Asn Trp Glu Arg Leu Gly Glu Asp Glu Glu Asp
    770                 775                 780

Gln Ser Leu Asp Asp Met Glu Lys Ile Ser Arg Gly Pro Thr Gly Arg
785                 790                 795                 800

Leu Arg Ile His His Ala Lys Leu Ala Gln Ala Gly Ala Tyr Gln Cys
                805                 810                 815

Ile Val Asp Asn Gly Val Ala Pro Pro Ala Arg Arg Leu Leu Arg Leu
            820                 825                 830

Val Val Arg Phe Ala Pro Gln Val Glu His Pro Thr Pro Leu Thr Lys
        835                 840                 845

Val Ala Ala Ala Gly Asp Ser Thr Ser Ser Ala Thr Leu His Cys Arg
    850                 855                 860

Ala Arg Gly Val Pro Asn Ile Val Phe Thr Trp Thr Lys Asn Gly Val
865                 870                 875                 880

Pro Leu Asp Leu Gln Asp Pro Arg Tyr Thr Glu His Thr Tyr His Gln
```

-continued 885 890 895

Gly Gly Val His Ser Ser Leu Leu Thr Ile Ala Asn Val Ser Ala Ala
900 905 910

Gln Asp Tyr Ala Leu Phe Thr Cys Thr Ala Thr Asn Ala Leu Gly Ser
915 920 925

Asp Gln Thr Asn Ile Gln Leu Val Ser Ile Ser Arg Pro Asp Pro Pro
930 935 940

Ser Gly Leu Lys Val Val Ser Leu Thr Pro His Ser Val Gly Leu Glu
945 950 955 960

Trp Lys Pro Gly Phe Asp Gly Gly Leu Pro Gln Arg Phe Cys Ile Arg
965 970 975

Tyr Glu Ala Leu Gly Thr Pro Gly Phe His Tyr Val Asp Val Val Pro
980 985 990

Pro Gln Ala Thr Thr Phe Thr Leu Thr Gly Leu Gln Pro Ser Thr Arg
995 1000 1005

Tyr Arg Val Trp Leu Leu Ala Ser Asn Ala Leu Gly Asp Ser Gly
1010 1015 1020

Leu Ala Asp Lys Gly Thr Gln Leu Pro Ile Thr Thr Pro Gly Leu
1025 1030 1035

His Gln Pro Ser Gly Glu Pro Glu Asp Gln Leu Pro Thr Glu Pro
1040 1045 1050

Pro Ser Gly Pro Ser Gly
1055

<210> SEQ ID NO 2
<211> LENGTH: 3201
<212> TYPE: DNA
<213> ORGANISM: Artificial Sequence
<220> FEATURE:
<223> OTHER INFORMATION: sequence encoding extracellular domain of nephrin (aa1-1059)

<400> SEQUENCE: 2
atggccctgg ggacgacgct cagggcttct ctcctgctcc tggggctgct gactgaaggc 60
ctggcgcatt ggcgattcct gcctccgttc cccggggctt ctgggccctg cctgaaaacc 120
tgacggtggt ggaggggcct cagtggagct gcgttgtggg gtcagcaccc ctggcagtgc 180
ggtgcaatgg gccaaagatg ggctgctcct gggccccgac cccaggatcc caggcttccc 240
gaggtaccgc ctggaagggg accctgctag agggaattcc acctgcacat cgaggcctgt 300
gacctcagcg atgacgcgga gtatgagtgc caggtcggcc gctctgagat ggggcccgag 360
ctcgtgtctc ccagagtgat cctctccatc ctggttcctc ccaagctgct cctgctgacc 420
ccagaggcag gcaccatggt cacctgggta gctgggcagg agtacgtggt caactgtgtg 480
tctggggacg cgaagccagc acctgacatc accattctcc tgagtggaca gacaatatct 540
gacatctctg caaacgtgaa cgagggctcc cagcagaaac tcttcactgt ggaggccaca 600
gccagggtga caccccggag ctcagataat aggcagttgc tggtctgtga ggcgtctagc 660
ccagcactgg aggcccccat caaggcctca ttcaccgtga atgttctgtt ccctccagga 720
ccccctgtca tcgagtggcc aggcctggat gaggggcacg tgcgggcagg acagagcttg 780
gagctgccgt gcgtggcccg agggggtaat cccttagcca cactgcagtg gctgaagaat 840
ggccagccgg tgtccacagc gtggggcaca gagcacaccc aggcggtggc ccgcagtgtg 900
ctggtgatga ccgtgaggcc agaagaccat ggagcgcagc tcagctgcga ggcccacaac 960
agcgtgtctg cagggaccca ggagcacggc atcacactgc aggtcacctt tccccctagt 1020

```
gccattatta tcttgggatc tgcatcccag actgagaaca agaacgtgac actctcctgt   1080
gtcagcaagt ccagtcgccc gcgggttctg ctacgatggt ggctgggctg gcggcagctg   1140
ctgcccatgg aggagacagt catggatgga ctgcatggcg gtcacatctc catgtccaac   1200
ctgacattcc tggcgcggcg ggaggacaac ggtctgaccc tcacatgtga ggccttcagt   1260
gaagccttca ccaaggagac cttcaagaag tcgctcatcc tgaacgtaaa atatcccgcc   1320
cagaaactgt ggattgaggg tcccccagag ggccagaagc tccgggctgg gacccgggtg   1380
aggctggtgt gtttggctat cgggggcaac ccagagccct ccctcatgtg gtacaaggac   1440
tcgcgcaccg tgaccgagtc gcggctgccg caggagtcgc ggcgcgtgca tctcggcagc   1500
gtggagaaat ctgggagcac cttctcccga gagctggtgc tggtcacagg gccgtcggac   1560
aaccaggcca agttcacgtg caaggctgga cagctcagcg cgtccacgca gctggcggtg   1620
cagtttcccc caactaacgt gacgatcctg gccaacgcat ccgcactgcg cccgggagac   1680
gccttaaact tgacatgcgt cagcgtcagc agcaatccgc cggtcaactt gtcctgggac   1740
aaggaagggg agaggctgga gggcgtggcc gccccacccc ggagagcccc attcaaaggc   1800
tccgccgccg ccaggagcgt ccttctgcaa gtgtcatccc gcgatcatgg ccagcgcgtg   1860
acctgccgcg cccacagcgc cgagctccgc gaaaccgtga gctccttcta tcgcctcaac   1920
gtactgtacc gtccagagtt cctgggggag caggtgctgg tggtgaccgc ggtggagcag   1980
ggcgaggcgt tgctgcccgt gtccgtgtcc gctaaccccg cccccgaggc cttcaactgg   2040
accttccgcg gctatcgcct cagtccagcg ggcggccccc ggcatcgcat cctgtccagc   2100
ggggctctgc atctgtggaa tgtgacccgc gcggacgacg gcctctatca gctgcactgc   2160
cagaactctg agggcaccgc ggaagcgcgg ctgcggctgg acgtgcacta tgctcccacc   2220
atccgtgccc tccaggaccc cactgaggtg aacgtcgggg gttctgtgga catagtctgc   2280
actgtcgatg ccaatcccat cctcccgggc atgttcaact gggagagact gggagaagat   2340
gaggaggacc agagcctgga tgacatggag aagatatcca ggggaccaac ggggcgcctg   2400
cggattcacc atgccaaact ggcccaggct ggcgcttacc agtgcattgt ggacaatggg   2460
gtggcgcctc cagcacgacg gctgctccgt cttgttgtca gatttgcccc ccaggtggag   2520
caccccactc ccctaactaa ggtggctgca gctggagaca gcaccagttc tgccaccctc   2580
cactgccgtg cccgaggtgt ccccaacatc gttttcactt ggacaaaaaa cggggtccct   2640
ctggatctcc aagatcccag gtacacggag cacacatacc accaaggtgg tgtccacagc   2700
agcctcctga ccattgccaa cgtgtctgcc gcccaggatt acgccctctt cacatgtaca   2760
gccaccaacg cccttggctc ggaccaaacc aacattcaac ttgtcagcat cagccgccct   2820
gaccctccat caggattaaa ggttgtgagt ctgaccccac actccgtggg gctggagtgg   2880
aagcctggct ttgatggggg cctgccacag aggttctgca tcaggtatga ggccctgggg   2940
actccagggt tccactatgt ggatgtcgta ccaccccagg ccaccacctt cacgctgact   3000
ggtctacagc cttctacaag atacagggtc tggctgctgg ccagtaatgc cttgggggac   3060
agtggactgg ctgacaaagg gacccagctt cccatcacta ccccaggtct ccaccagcct   3120
tctggagaac ctgaagacca gctgcccaca gagccacctt caggaccctc ggggggggtcc  3180
caccaccatc accaccatta g                                              3201
```

<210> SEQ ID NO 3
<211> LENGTH: 1067
<212> TYPE: PRT

```
<213> ORGANISM: Artificial Sequence
<220> FEATURE:
<223> OTHER INFORMATION: extracellular domain of nephrin (aa1-1059) with
      6HIS tag

<400> SEQUENCE: 3

Met Ala Leu Gly Thr Thr Leu Arg Ala Ser Leu Leu Leu Leu Gly Leu
1               5                   10                  15

Leu Thr Glu Gly Leu Ala Gln Leu Ala Ile Pro Ala Ser Val Pro Arg
            20                  25                  30

Gly Phe Trp Ala Leu Pro Glu Asn Leu Thr Val Val Glu Gly Ala Ser
        35                  40                  45

Val Glu Leu Arg Cys Gly Val Ser Thr Pro Gly Ser Ala Val Gln Trp
    50                  55                  60

Ala Lys Asp Gly Leu Leu Leu Gly Pro Asp Pro Arg Ile Pro Gly Phe
65                  70                  75                  80

Pro Arg Tyr Arg Leu Glu Gly Asp Pro Ala Arg Gly Glu Phe His Leu
                85                  90                  95

His Ile Glu Ala Cys Asp Leu Ser Asp Asp Ala Glu Tyr Glu Cys Gln
            100                 105                 110

Val Gly Arg Ser Glu Met Gly Pro Glu Leu Val Ser Pro Arg Val Ile
        115                 120                 125

Leu Ser Ile Leu Val Pro Pro Lys Leu Leu Leu Leu Thr Pro Glu Ala
    130                 135                 140

Gly Thr Met Val Thr Trp Val Ala Gly Gln Glu Tyr Val Val Asn Cys
145                 150                 155                 160

Val Ser Gly Asp Ala Lys Pro Ala Pro Asp Ile Thr Ile Leu Leu Ser
                165                 170                 175

Gly Gln Thr Ile Ser Asp Ile Ser Ala Asn Val Asn Glu Gly Ser Gln
            180                 185                 190

Gln Lys Leu Phe Thr Val Glu Ala Thr Ala Arg Val Thr Pro Arg Ser
        195                 200                 205

Ser Asp Asn Arg Gln Leu Leu Val Cys Glu Ala Ser Ser Pro Ala Leu
    210                 215                 220

Glu Ala Pro Ile Lys Ala Ser Phe Thr Val Asn Val Leu Phe Pro Pro
225                 230                 235                 240

Gly Pro Pro Val Ile Glu Trp Pro Gly Leu Asp Glu Gly His Val Arg
                245                 250                 255

Ala Gly Gln Ser Leu Glu Leu Pro Cys Val Ala Arg Gly Gly Asn Pro
            260                 265                 270

Leu Ala Thr Leu Gln Trp Leu Lys Asn Gly Gln Pro Val Ser Thr Ala
        275                 280                 285

Trp Gly Thr Glu His Thr Gln Ala Val Ala Arg Ser Val Leu Val Met
    290                 295                 300

Thr Val Arg Pro Glu Asp His Gly Ala Gln Leu Ser Cys Glu Ala His
305                 310                 315                 320

Asn Ser Val Ser Ala Gly Thr Gln Glu His Gly Ile Thr Leu Gln Val
                325                 330                 335

Thr Phe Pro Pro Ser Ala Ile Ile Ile Leu Gly Ser Ala Ser Gln Thr
            340                 345                 350

Glu Asn Lys Asn Val Thr Leu Ser Cys Val Ser Lys Ser Ser Arg Pro
        355                 360                 365

Arg Val Leu Leu Arg Trp Trp Leu Gly Trp Arg Gln Leu Leu Pro Met
    370                 375                 380
```

```
Glu Glu Thr Val Met Asp Gly Leu His Gly Gly His Ile Ser Met Ser
385                 390                 395                 400

Asn Leu Thr Phe Leu Ala Arg Arg Glu Asp Asn Gly Leu Thr Leu Thr
                405                 410                 415

Cys Glu Ala Phe Ser Glu Ala Phe Thr Lys Glu Thr Phe Lys Lys Ser
            420                 425                 430

Leu Ile Leu Asn Val Lys Tyr Pro Ala Gln Lys Leu Trp Ile Glu Gly
        435                 440                 445

Pro Pro Glu Gly Gln Lys Leu Arg Ala Gly Thr Arg Val Arg Leu Val
    450                 455                 460

Cys Leu Ala Ile Gly Gly Asn Pro Glu Pro Ser Leu Met Trp Tyr Lys
465                 470                 475                 480

Asp Ser Arg Thr Val Thr Glu Ser Arg Leu Pro Gln Glu Ser Arg Arg
                485                 490                 495

Val His Leu Gly Ser Val Glu Lys Ser Gly Ser Thr Phe Ser Arg Glu
            500                 505                 510

Leu Val Leu Val Thr Gly Pro Ser Asp Asn Gln Ala Lys Phe Thr Cys
        515                 520                 525

Lys Ala Gly Gln Leu Ser Ala Ser Thr Gln Leu Ala Val Gln Phe Pro
    530                 535                 540

Pro Thr Asn Val Thr Ile Leu Ala Asn Ala Ser Ala Leu Arg Pro Gly
545                 550                 555                 560

Asp Ala Leu Asn Leu Thr Cys Val Ser Val Ser Ser Asn Pro Pro Val
                565                 570                 575

Asn Leu Ser Trp Asp Lys Glu Gly Glu Arg Leu Glu Gly Val Ala Ala
            580                 585                 590

Pro Pro Arg Arg Ala Pro Phe Lys Gly Ser Ala Ala Ala Arg Ser Val
        595                 600                 605

Leu Leu Gln Val Ser Ser Arg Asp His Gly Gln Arg Val Thr Cys Arg
    610                 615                 620

Ala His Ser Ala Glu Leu Arg Glu Thr Val Ser Ser Phe Tyr Arg Leu
625                 630                 635                 640

Asn Val Leu Tyr Arg Pro Glu Phe Leu Gly Glu Gln Val Leu Val Val
                645                 650                 655

Thr Ala Val Glu Gln Gly Glu Ala Leu Leu Pro Val Ser Val Ser Ala
            660                 665                 670

Asn Pro Ala Pro Glu Ala Phe Asn Trp Thr Phe Arg Gly Tyr Arg Leu
        675                 680                 685

Ser Pro Ala Gly Gly Pro Arg His Arg Ile Leu Ser Ser Gly Ala Leu
    690                 695                 700

His Leu Trp Asn Val Thr Arg Ala Asp Asp Gly Leu Tyr Gln Leu His
705                 710                 715                 720

Cys Gln Asn Ser Glu Gly Thr Ala Glu Ala Arg Leu Arg Leu Asp Val
                725                 730                 735

His Tyr Ala Pro Thr Ile Arg Ala Leu Gln Asp Pro Thr Glu Val Asn
            740                 745                 750

Val Gly Gly Ser Val Asp Ile Val Cys Thr Val Asp Ala Asn Pro Ile
        755                 760                 765

Leu Pro Gly Met Phe Asn Trp Glu Arg Leu Gly Glu Asp Glu Glu Asp
    770                 775                 780

Gln Ser Leu Asp Asp Met Glu Lys Ile Ser Arg Gly Pro Thr Gly Arg
785                 790                 795                 800

Leu Arg Ile His His Ala Lys Leu Ala Gln Ala Gly Ala Tyr Gln Cys
```

-continued

```
                805                 810                 815

Ile Val Asp Asn Gly Val Ala Pro Pro Ala Arg Arg Leu Leu Arg Leu
            820                 825                 830

Val Val Arg Phe Ala Pro Gln Val Glu His Pro Thr Pro Leu Thr Lys
        835                 840                 845

Val Ala Ala Ala Gly Asp Ser Thr Ser Ser Ala Thr Leu His Cys Arg
    850                 855                 860

Ala Arg Gly Val Pro Asn Ile Val Phe Thr Trp Thr Lys Asn Gly Val
865                 870                 875                 880

Pro Leu Asp Leu Gln Asp Pro Arg Tyr Thr Glu His Thr Tyr His Gln
                885                 890                 895

Gly Gly Val His Ser Ser Leu Leu Thr Ile Ala Asn Val Ser Ala Ala
            900                 905                 910

Gln Asp Tyr Ala Leu Phe Thr Cys Thr Ala Thr Asn Ala Leu Gly Ser
        915                 920                 925

Asp Gln Thr Asn Ile Gln Leu Val Ser Ile Ser Arg Pro Asp Pro Pro
    930                 935                 940

Ser Gly Leu Lys Val Val Ser Leu Thr Pro His Ser Val Gly Leu Glu
945                 950                 955                 960

Trp Lys Pro Gly Phe Asp Gly Gly Leu Pro Gln Arg Phe Cys Ile Arg
                965                 970                 975

Tyr Glu Ala Leu Gly Thr Pro Gly Phe His Tyr Val Asp Val Val Pro
            980                 985                 990

Pro Gln Ala Thr Thr Phe Thr Leu  Thr Gly Leu Gln Pro  Ser Thr Arg
        995                 1000                1005

Tyr Arg  Val Trp Leu Leu Ala  Ser Asn Ala Leu Gly  Asp Ser Gly
    1010                 1015                 1020

Leu Ala  Asp Lys Gly Thr Gln  Leu Pro Ile Thr Thr  Pro Gly Leu
    1025                 1030                 1035

His Gln  Pro Ser Gly Glu Pro  Glu Asp Gln Leu Pro  Thr Glu Pro
    1040                 1045                 1050

Pro Ser  Gly Pro Ser Gly Gly  Ser His His His His  His His
    1055                 1060                 1065
```